US 9,572,861 B2

(12) United States Patent
Sasisekharan et al.

(10) Patent No.: US 9,572,861 B2
(45) Date of Patent: **\*Feb. 21, 2017**

(54) ENGINEERED POLYPEPTIDE AGENTS FOR TARGETED BROAD SPECTRUM INFLUENZA NEUTRALIZATION

(71) Applicant: Massachusetts Institute of Technology, Cambridge, MA (US)

(72) Inventors: Ram Sasisekharan, Lexington, MA (US); Karthik Viswanathan, Waltham, MA (US); Venkataramanan Soundararajan, Windham, NH (US); S. Raguram, Hillsborough, NJ (US); Viswanathan Sasisekharan, Cambridge, MA (US); Vidya Subramanian, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/094,522

(22) Filed: Apr. 8, 2016

(65) Prior Publication Data

US 2016/0317612 A1    Nov. 3, 2016

Related U.S. Application Data

(63) Continuation of application No. 14/163,882, filed on Jan. 24, 2014, now Pat. No. 9,334,309, which is a continuation of application No. 13/015,455, filed on Jan. 27, 2011, now Pat. No. 8,637,456.

(60) Provisional application No. 61/298,776, filed on Jan. 27, 2010.

(51) Int. Cl.
| | | |
|---|---|---|
| *C07K 14/00* | (2006.01) | |
| *C07K 14/005* | (2006.01) | |
| *G01N 33/569* | (2006.01) | |
| *A61K 38/00* | (2006.01) | |
| *A61K 38/16* | (2006.01) | |
| *C12N 7/00* | (2006.01) | |
| *A61K 9/00* | (2006.01) | |

(52) U.S. Cl.
CPC .......... *A61K 38/162* (2013.01); *A61K 9/0053* (2013.01); *A61K 9/0073* (2013.01); *C12N 7/00* (2013.01); *C12N 2760/16122* (2013.01); *C12N 2760/16133* (2013.01)

(58) Field of Classification Search
CPC .... A61K 38/00; A61K 38/162; A61K 9/0073; A61K 9/0053; C07K 14/001; C07K 14/005; C12N 2760/16122; C12N 7/00; C12N 2760/16133; G01N 2333/11; G01N 33/56983
See application file for complete search history.

(56) References Cited

U.S. PATENT DOCUMENTS

2003/0077606 A1* 4/2003 Rosen .................. C07K 14/47
435/6.16

* cited by examiner

*Primary Examiner* — Hasan Ahmed
*Assistant Examiner* — Erinne Dabkowski
(74) *Attorney, Agent, or Firm* — Choate, Hall & Stewart LLP; Brenda Herschbach Jarrell; Cassandra Gianna Luca

(57) ABSTRACT

The present invention provides novel agents for broad spectrum influenza neutralization. The present invention provides agents for inhibiting influenza infection by bind to the influenza virus and/or hemagglutinin (HA) polypeptides and/or HA receptors, and reagents and methods relating thereto. The present invention provides a system for analyzing interactions between infolds and the interaction partners that bind to them.

11 Claims, 22 Drawing Sheets

FIG. 1

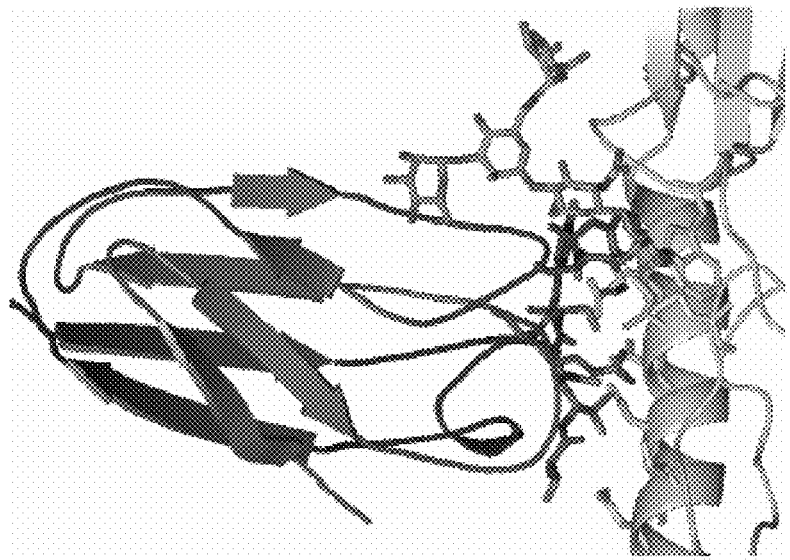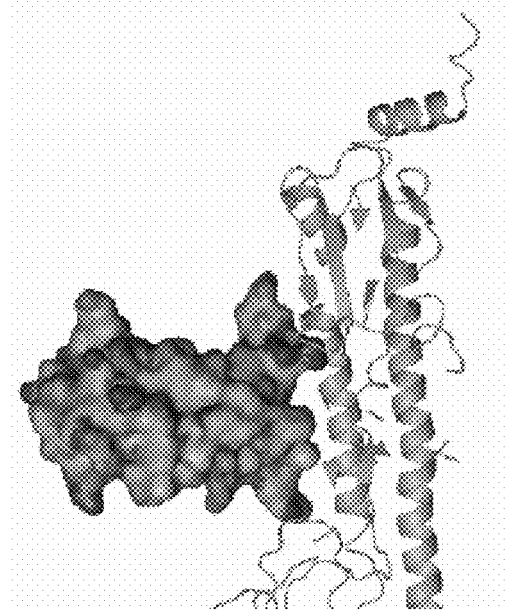
FIG. 6

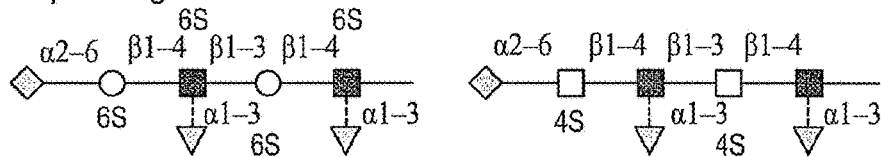
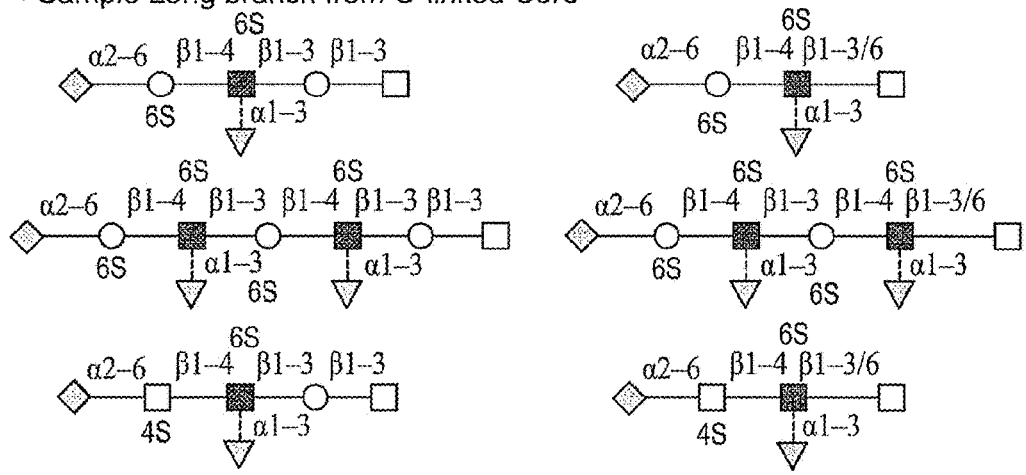
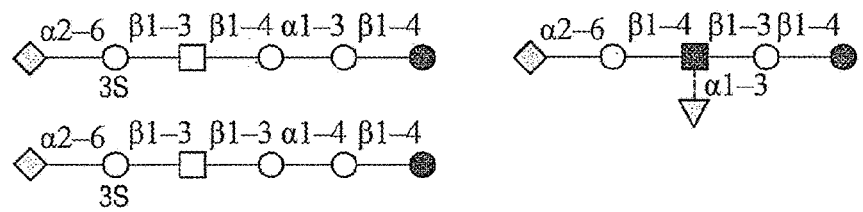
FIG. 12

| Residue | Amino acids suggested for substitution (≥2% of reads) | Other Permitted Substitutions (<2% of reads) |
|---|---|---|
| Trp HA2 – 21 | Tyr, Ile, Met, Phe, His, Cys, Pro | Gly, Val, Arg, Ser, Thr, Trp, Leu, Ala |
| Ile HA2 – 45 | Ile, Met, Phe, Leu, Val, Trp, Cys | Tyr, Pro, Ala, Thr |
| Asp<br>Asn<br>Ala HA2 – 19 | Arg, Lys, His, Ser, Thr, Asn<br>Asn, Asp, Gln, Glu, Ser, Thr, Lys<br>Ile, Val, Ala, Gly | Tyr, Gly, Gln, Glu, Asp, Pro, Ala<br>His,

SEQUENCE LISTING

```
<160> NUMBER OF SEQ ID NOS: 41

<210> SEQ ID NO 1
<211> LENGTH: 95
<212> TYPE: PRT
<213> ORGANISM: Artificial Sequence
<220> FEATURE:
<223> OTHER INFORMATION: Synthetic Infold Peptide

<400> SEQUENCE: 1

Met Glu His Pro Val Ala Thr Leu Ser Thr Val Glu Arg Arg Ala Ile
1               5                   10                  15

Asn Leu Thr Trp Thr Lys Pro Phe Asp Gly Asn Ser Pro Leu Ile Arg
            20                  25                  30

Tyr Ile Leu Glu Met Ser Glu Asn Asn Ala Pro Trp Thr Val Leu Leu
        35                  40                  45

Ala Ser Val Asp Pro Lys Ala Thr Ser Val Thr Val Lys Gly Leu Val
    50                  55                  60

Pro Ala Arg Ser Tyr Gln Phe Arg Leu Cys Ala Val Asn Asp Val Gly
65                  70                  75                  80

Lys Gly Gln Phe Ser Lys Asp Thr Glu Arg Val Ser Leu Pro Glu
                85                  90                  95

<210> SEQ ID NO 2
<211> LENGTH: 111
<212> TYPE: PRT
<213> ORGANISM: Artificial Sequence
<220> FEATURE:
<223> OTHER INFORMATION: Synthetic Infold Peptide

<400> SEQUENCE: 2

Met Pro Ser Val Ser Asp Val Pro Arg Asp Leu Glu Val Val Ala Ala
1               5                   10                  15

Thr Pro Thr Ser Leu Leu Ile Ser Trp Asp Ala Pro Trp Thr Met Ser
            20                  25                  30

Ser Arg Tyr Tyr Arg Ile Thr Tyr Gly Glu Thr Gly Gly Asn Ser Pro
        35                  40                  45

Val Gln Glu Phe Thr Val Pro Gly Phe Met Gly Gly Lys Ser Thr Ala
    50                  55                  60
```

```
Thr Ile Ser Gly Leu Lys Pro Gly Val Asp Tyr Thr Ile Thr Val Tyr
 65                  70                  75                  80

Ala Val Tyr Gly Arg Gly Asp Ser Pro Ala Ser Ser Lys Pro Ile Ser
                 85                  90                  95

Ile Asn Tyr Arg Thr Glu Ile Asp Lys Pro Ser Gln Gly Gly Ser
            100                 105                 110

<210> SEQ ID NO 3
<211> LENGTH: 95
<212> TYPE: PRT
<213> ORGANISM: Artificial Sequence
<220> FEATURE:
<223> OTHER INFORMATION: Synthetic Infold Petide

<400> SEQUENCE: 3

Met Glu His Pro Val Ala Thr Leu Ser Thr Val Glu Arg Arg Ala Ile
  1               5                  10                  15

Gln Leu Thr Trp Asp Ala Pro Val Thr Ser Ser Arg Arg Tyr Ile
                 20                  25                  30

Leu Glu Met Ser Glu Asn Asn Ala Pro Trp Thr Val Leu Leu Thr Val
             35                  40                  45

Pro Gly Phe Met Gly Gly Lys Thr Ser Val Thr Val Lys Gly Leu Val
 50                  55                  60

Pro Ala Arg Ser Tyr Gln Phe Arg Leu Cys Ala Val Asn Tyr Val Gly
 65                  70                  75                  80

Lys Gly Gln Phe Ser Lys Asp Thr Glu Arg Val Ser Leu Pro Glu
                 85                  90                  95

<210> SEQ ID NO 4
<211> LENGTH: 106
<212> TYPE: PRT
<213> ORGANISM: Artificial Sequence
<220> FEATURE:
<223> OTHER INFORMATION: Synthetic Infold Peptide

<400> SEQUENCE: 4

Met Val Pro Arg Asp Leu Glu Val Val Ala Ala Thr Pro Thr Ser Leu
  1               5                  10                  15

Leu Ile Ser Trp Asp Ala Pro Val Thr Thr Ser Ser Arg Tyr Tyr Arg
                 20                  25                  30

Ile Thr Tyr Gly Glu Thr Gly Gly Asn Ser Pro Val Gln Glu Phe Thr
             35                  40                  45

Val Pro Gly Phe Met Gly Gly Lys Ser Thr Ala Thr Ile Arg Gly Leu
 50                  55                  60

Lys Pro Gly Val Asp Tyr Thr Ile Thr Val Tyr Ala Val Tyr Gly Arg
 65                  70                  75                  80

Gly Asp Ser Pro Ala Ser Ser Lys Pro Ile Ser Ile Asn Tyr Arg Thr
                 85                  90                  95

Glu Ile Asp Lys Pro Ser Gln Gly Gly Ser
            100                 105

<210> SEQ ID NO 5
<211> LENGTH: 104
<212> TYPE: PRT
<213> ORGANISM: Artificial Sequence
<220> FEATURE:
<223> OTHER INFORMATION: Synthetic Infold Peptide

<400> SEQUENCE: 5

Met Gly Ser Leu Glu Val Val Ala Ala Ser Gly Ala Asp Ser Leu Leu
```

```
    1               5                  10                 15
Ile Ser Trp Asp Ala Pro Phe Thr Ile Tyr Ser Arg Tyr Tyr Arg Ile
                20                 25                 30
Thr Tyr His Val Glu Lys Asn Gly Ser Lys Tyr Gly Pro Asp Gly Leu
                35                 40                 45
Pro Tyr Leu Gln Glu Phe Thr Val Pro Gly Phe Met Gly Gly Lys Ser
                50                 55                 60
Thr Ala Thr Ile Arg Asn Val Thr Glu Asp Asp Tyr Thr Ile Thr Val
 65                 70                 75                 80
Tyr Ala Val Tyr Gly Arg Gly Asp Ser Pro Ala Ser Ser Lys Pro Ile
                    85                 90                 95
Ser Ile Asn Tyr Arg Thr Asp Val
                   100
```

<210> SEQ ID NO 6
<211> LENGTH: 93
<212> TYPE: PRT
<213> ORGANISM: Artificial Sequence
<220> FEATURE:
<223> OTHER INFORMATION: Synthetic Infold Peptide

<400> SEQUENCE: 6

```
Met Ser Pro Ser Ile Asp Gln Val Glu Pro Tyr Ser Ser Thr Ala Gln
 1               5                  10                 15
Val Gln Phe Lys Arg Pro Ser Arg Thr Val Pro Ile Tyr His Tyr Lys
                20                 25                 30
Ala Glu Trp Arg Ala Val Gly Glu Val Trp His Ser Lys Trp Tyr
                35                 40                 45
Pro Phe Arg Ile Gly Gly Lys Gly Ile Val Thr Ile Val Gly Leu Lys
                50                 55                 60
Pro Glu Thr Thr Tyr Ala Val Arg Leu Ala Ala Phe Thr Ser Gly
 65                 70                 75                 80
Gly Arg Ser Ser Ala Ala Ser Glu Phe Lys Thr Gln Pro
                    85                 90
```

<210> SEQ ID NO 7
<211> LENGTH: 83
<212> TYPE: PRT
<213> ORGANISM: Artificial Sequence
<220> FEATURE:
<223> OTHER INFORMATION: Synthetic Infold Peptide

<400> SEQUENCE: 7

```
Met Ala Gly Ser Pro Ala Asn Ala Ser Thr Ser Gly Gly Asp Val Glu
 1               5                  10                 15
Phe Thr Cys Arg Val Phe Thr Asp Tyr Pro His Ile Gln Trp Ile Leu
                20                 25                 30
His Val Glu Tyr Leu Lys Val Leu Thr Ala Ala Tyr Lys Lys Arg Lys
                35                 40                 45
Glu Thr Leu Tyr Ile Arg Asn Val Thr Glu Asp Ala Gly Glu Tyr Thr
 50                 55                 60
Cys Leu Ala Gly Asn Asn Glu Gly Ile Ser Phe His Ser Ala Trp Leu
 65                 70                 75                 80
Thr Val Leu
```

<210> SEQ ID NO 8
<211> LENGTH: 88
<212> TYPE: PRT

<213> ORGANISM: Artificial Sequence
<220> FEATURE:
<223> OTHER INFORMATION: Synthetic Infold Peptide

<400> SEQUENCE: 8

```
Met Gly Ser Pro Leu Ala Pro Ser Ser Lys Ser Thr Ser Gly Gly Thr
1               5                   10                  15
Ala Ala Leu Gly Cys Leu Val Lys Asp Pro Phe Thr Ile Ser Phe Val
            20                  25                  30
Thr Val Ser Trp Asn Ser Gly Ala Leu Thr Ser Gly Val His Thr Pro
        35                  40                  45
Gly Tyr Lys Lys Ser Ser Val Val Thr Val Pro Ser Ser Ser Leu Gly
50                  55                  60
Thr Gln Thr Tyr Ile Cys Asn Val Asn His Tyr Gly Lys Pro Ser Asn
65                  70                  75                  80
Thr Lys Val Asp Lys Arg Val Glu
                85
```

<210> SEQ ID NO 9
<211> LENGTH: 132
<212> TYPE: PRT
<213> ORGANISM: Artificial Sequence
<220> FEATURE:
<223> OTHER INFORMATION: Synthetic Infold Peptide

<400> SEQUENCE: 9

```
Met Val Tyr Glu Leu Gln Val Gln Lys Ser Val Thr Val Gln Glu Gly
1               5                   10                  15
Leu Cys Val Leu Val Pro Cys Ser Phe Ser Ser Glu Val Thr Phe Ser
            20                  25                  30
Ser Phe Tyr Val Tyr Trp Phe Arg Asp Gly Gly His Gly Tyr Tyr Ala
        35                  40                  45
Glu Val Val Ala Thr Ile Ser Pro Met Phe Gly Thr Pro Asn Tyr Ala
50                  55                  60
Pro Glu Thr Gln Gly Arg Phe Arg Leu Leu Gly Asp Val Gln Lys Lys
65                  70                  75                  80
Asn Cys Ser Leu Ser Ile Gly Asp Ala Arg Met Glu Asp Thr Gly Ser
            85                  90                  95
Tyr Phe Phe Arg Val Glu Arg Gly Tyr Ile Cys Ser Gly Gly Thr Cys
        100                 105                 110
Arg Asp Val Lys Tyr Ser Tyr Gln Gln Asn Lys Leu Asn Leu Glu Val
    115                 120                 125
Thr Ala Leu Ile
    130
```

<210> SEQ ID NO 10
<211> LENGTH: 111
<212> TYPE: PRT
<213> ORGANISM: Artificial Sequence
<220> FEATURE:
<223> OTHER INFORMATION: Synthetic Infold Peptide

<400> SEQUENCE: 10

```
Met Val Tyr Glu Leu Gln Val Gln Lys Ser Val Thr Val Gln Glu Gly
1               5                   10                  15
Leu Cys Val Leu Val Pro Cys Ser Phe Ser Ser Glu Val Thr Phe Ser
            20                  25                  30
Ser Phe Tyr Val Tyr Trp Phe Arg Asp Gly Gly His Gly Tyr Tyr Ala
        35                  40                  45
```

-continued

Glu Val Phe Tyr Thr Thr Ser Pro Gly Phe Met Gly Gly Lys Asn Cys
 50                  55                  60

Ser Leu Ser Ile Gly Asp Ala Arg Met Glu Asp Thr Gly Ser Tyr Phe
 65                  70                  75                  80

Phe Arg Val Glu Arg Gly Tyr Ile Cys Ser Gly Gly Thr Cys Arg Asp
                 85                  90                  95

Val Lys Tyr Ser Tyr Gln Gln Asn Lys Leu Asn Leu Glu Val Thr
             100                 105                 110

<210> SEQ ID NO 11
<211> LENGTH: 245
<212> TYPE: PRT
<213> ORGANISM: Artificial Sequence
<220> FEATURE:
<223> OTHER INFORMATION: Synthetic Infold Peptide

<400> SEQUENCE: 11

Met Glu Val Gln Leu Val Glu Ser Gly Gly Gly Leu Val Lys Ala Gly
  1               5                  10                  15

Gly Ser Leu Ile Leu Ser Cys Gly Val Ser Asn Val Thr Ile Ser Ser
                 20                  25                  30

His Thr Met Asn Trp Val Arg Val Pro Gly Gly Gly Leu Glu Trp
             35                  40                  45

Val Ala Ser Ile Ser Thr Met Phe Thr Tyr Arg Asp Tyr Ala Asp Ala
 50                  55                  60

Val Lys Gly Arg Phe Thr Val Ser Arg Asp Asp Leu Glu Asp Phe Val
 65                  70                  75                  80

Tyr Leu Gln Met His Lys Met Arg Val Glu Asp Thr Ala Ile Tyr Tyr
                 85                  90                  95

Cys Ala Arg Ser Pro Ser Tyr Ile Cys Ser Gly Gly Thr Cys Val Phe
                100                 105                 110

Asp Ala Trp Gly Pro Gly Thr Val Val Thr Val Ser Ser Gly Gly Gly
            115                 120                 125

Ser Gly Gly Gly Ser Gly Gly Gly Ile Gln Pro Gly Met Thr Gln
            130                 135                 140

Ser Pro Ser Thr Leu Ser Ala Ser Val Gly Asp Thr Ile Thr Ile Thr
145                 150                 155                 160

Cys Arg Ala Ser Gln Ser Ile Glu Thr Trp Leu Ala Trp Tyr Gln Gln
                165                 170                 175

Lys Pro Gly Lys Ala Pro Lys Leu Leu Ile Tyr Lys Ala Ser Thr Leu
            180                 185                 190

Lys Thr Gly Val Pro Ser Arg Phe Ser Gly Ser Gly Ser Gly Thr Glu
            195                 200                 205

Phe Thr Leu Thr Ile Ser Gly Leu Gln Phe Asp Asp Phe Ala Thr Tyr
            210                 215                 220

His Cys Gln His Tyr Ala Gly Tyr Ser Ala Thr Phe Gly Gln Gly Thr
225                 230                 235                 240

Arg Val Glu Ile Lys
                245

<210> SEQ ID NO 12
<211> LENGTH: 244
<212> TYPE: PRT
<213> ORGANISM: Artificial Sequence
<220> FEATURE:
<223> OTHER INFORMATION: Synthetic Infold Peptide -continued

```
<400> SEQUENCE: 12

Met Glu Val Gln Leu Val Glu Ser Gly Gly Gly Leu Val Lys Ala Gly
1               5                   10                  15

Gly Ser Leu Ile Leu Ser Cys Gly Val Ser Asn Val Thr Ile Ser Ser
                20                  25                  30

His Thr Met Asn Trp Val Arg Val Pro Gly Gly Gly Leu Glu Trp
                35                  40                  45

Val Ala Ser Ile Ser Thr Met Phe Thr Tyr Arg Asp Tyr Ala Asp Ala
    50                  55                  60

Val Lys Gly Arg Phe Thr Val Ser Arg Asp Asp Leu Glu Asp Phe Val
65                  70                  75                  80

Tyr Leu Gln Met His Lys Met Arg Val Glu Asp Thr Ala Ile Tyr Tyr
                85                  90                  95

Cys Ala Arg Lys Gly Ser Asp Arg Leu Ser Asp Asn Asp Pro Phe Asp
            100                 105                 110

Ala Trp Gly Pro Gly Thr Val Val Thr Val Ser Ser Gly Gly Gly Ser
            115                 120                 125

Gly Gly Gly Ser Gly Gly Gly Ile Gln Pro Gly Met Thr Gln Ser
        130                 135                 140

Pro Ser Thr Leu Ser Ala Ser Val Gly Asp Thr Ile Thr Ile Thr Cys
145                 150                 155                 160

Arg Ala Ser Gln Ser Ile Glu Thr Trp Leu Ala Trp Tyr Gln Gln Lys
                165                 170                 175

Pro Gly Lys Ala Pro Lys Leu Leu Ile Tyr Lys Ala Ser Thr Leu Lys
            180                 185                 190

Thr Gly Val Pro Ser Arg Phe Ser Gly Ser Gly Ser Gly Thr Glu Phe
        195                 200                 205

Thr Leu Thr Ile Ser Gly Leu Gln Phe Asp Asp Phe Ala Thr Tyr His
    210                 215                 220

Cys Gln His Tyr Ala Gly Tyr Ser Ala Thr Phe Gly Gln Gly Thr Arg
225                 230                 235                 240

Val Glu Ile Lys

<210> SEQ ID NO 13
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 13

Met Val Gln Leu Val Glu Ala Gly Gly Gly Leu Val Lys Ala Gly Gly
1               5                   10                  15

Ser Leu Asp Leu Arg Cys Gly Val Ser Asn Val Thr Ile Ser Ser His
                20                  25                  30

Thr Met Asn Trp Lys Arg Arg Val Pro Gly Gly Gly Thr Glu Ser Val
            35                  40                  45

Ala Ser Ile Ser Thr Met Phe Thr Tyr Thr Ala Tyr Ala Asp Ala Val
    50                  55                  60

Lys Gly Arg Phe Thr Val Ser Arg Ala Asp Leu Glu Asp Ser Val Ser
65                  70                  75                  80

Leu Gln Met His Lys Met Arg Val Glu Asp Thr Ala Ile Tyr Tyr Cys
                85                  90                  95

Ala Arg Lys Gly Ser Asp Arg Leu Ser Asp Asn Asp Pro Phe Asp Ala
            100                 105                 110
```

-continued

```
Trp Gly Pro Gly Thr Val Val Thr Val Ser Pro
        115                 120

<210> SEQ ID NO 14
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 14

Met Val Gln Leu Val Glu Ser Gly Gly Gly Leu Val Gly Ser Thr Ser
1               5                   10                  15

Ser Leu Ile Leu Ser Cys Gly Val Ser Asn Phe Tyr Ile His Ser His
            20                  25                  30

Thr Met Asn Trp Val Arg Arg Ala Pro Ser Ala Gly Leu Glu Trp Val
        35                  40                  45

Ala Ser Ile Ser Thr Phe Val Tyr Tyr Arg Asp Tyr Ala Gln Ser Val
50                  55                  60

Ala Ser Ala Phe Thr Val Ser Arg Asp Thr Arg Gln Glu Phe Val Tyr
65                  70                  75                  80

Leu Gln Met Ala Ser Met Val Ala Gln Val Ser Ala Ile Tyr Tyr Cys
                85                  90                  95

Ala Arg Lys Gly Ser Ala Val Leu Ser Asp Asn Asp Pro Phe Asp Ala
            100                 105                 110

Trp Gly Pro Gly Thr Val Val Thr Val Ser Pro
        115                 120

<210> SEQ ID NO 15
<211> LENGTH: 124
<212> TYPE: PRT
<213> ORGANISM: Artificial Sequence
<220> FEATURE:
<223> OTHER INFORMATION: Synthetic Infold Peptide

<400> SEQUENCE: 15

Met Gln Val Gln Leu Val Gln Ser Gly Ala Glu Val Lys Lys Pro Gly
1               5                   10                  15

Ser Ser Val Lys Val Ser Cys Thr Ser Ser Glu Val Thr Phe Ser Ser
            20                  25                  30

Phe Thr Ile Ser Trp Val Arg Gln Ala Pro Gly Gln Gly Leu Glu Trp
        35                  40                  45

Leu Gly Gly Ile Ser Thr Met Phe Gly Thr Pro Asn Tyr Ala Gln Lys
    50                  55                  60

Phe Gln Gly Arg Val Thr Ile Thr Ala Asp Gln Ser Thr Arg Thr Ala
65                  70                  75                  80

Tyr Met Asp Leu Arg Ser Leu Arg Ser Glu Asp Thr Ala Val Tyr Tyr
                85                  90                  95

Cys Ala Arg Lys Gly Ser Asp Arg Leu Ser Asp Asn Asp Pro Phe Asp
            100                 105                 110

His Trp Gly Gln Gly Thr Leu Val Thr Val Ser Ser
        115                 120

<210> SEQ ID NO 16
<211> LENGTH: 111
<212> TYPE: PRT
<213> ORGANISM: Artificial Sequence
<220> FEATURE:
<223> OTHER INFORMATION: Synthetic Infold Peptide
```

-continued

<400> SEQUENCE: 16

```
Met Pro Ser Val Ser Asp Val Pro Arg Asp Leu Glu Val Val Ala Ala
1               5                   10                  15

Thr Pro Thr Ser Leu Leu Ile Ser Trp Ala Thr Thr Gly Lys Ala Ser
            20                  25                  30

Ser Leu Tyr Tyr Arg Ile Thr Tyr Gly Glu Thr Gly Gly Asn Ser Pro
        35                  40                  45

Val Gln Glu Phe Thr Val Pro Ala Phe Met Gly Gly Trp Val Lys Ala
    50                  55                  60

Thr Ile Arg Gly Leu Lys Pro Gly Val Asp Tyr Thr Ile Thr Val Tyr
65              70                  75                  80

Ala Val Tyr His Tyr Gly Gly Ser Asp Asp Thr Leu Ser Pro Ile Ser
                85                  90                  95

Ile Asn Tyr Arg Thr Glu Ile Asp Lys Pro Ser Gln Gly Gly Ser
            100                 105                 110
```

<210> SEQ ID NO 17
<211> LENGTH: 93
<212> TYPE: PRT
<213> ORGANISM: Artificial Sequence
<220> FEATURE:
<223> OTHER INFORMATION: Synthetic Infold Peptide

<400> SEQUENCE: 17

```
Met Arg Asp Leu Glu Val Val Ala Ala Thr Pro Thr Ser Leu Leu Ile
1               5                   10                  15

Ser Trp Asp Ala Pro Val Thr Thr Ser Ser Arg Tyr Tyr Ile Ile Glu
            20                  25                  30

Met Ser Glu Thr Asn Ala Pro Trp Thr Val Leu Phe Thr Val Pro Gly
        35                  40                  45

Phe Met Gly Gly Lys Ser Thr Ala Thr Ile Ser Gly Leu Lys Pro Gly
    50                  55                  60

Val Asp Tyr Thr Phe Arg Val Cys Ala Val Asn Tyr Val Gly Lys Gly
65              70                  75                  80

Gln Phe Ser Lys Asp Thr Glu Asn Val Arg Leu Glu Ile
                85                  90
```

<210> SEQ ID NO 18
<211> LENGTH: 116
<212> TYPE: PRT
<213> ORGANISM: Artificial Sequence
<220> FEATURE:
<223> OTHER INFORMATION: Synthetic Infold Peptide

<400> SEQUENCE: 18

```
Met Arg Asp Leu Glu Val Val Ala Ala Thr Pro Thr Ser Leu Leu Ile
1               5                   10                  15

Ser Trp Asp Ala Pro Val Thr Val Ser Tyr Arg Ile Thr Tyr
            20                  25                  30

Gly Glu Thr Gly Gly Asn Ser Pro Val Gln Glu Phe Thr Val Ser Thr
        35                  40                  45

Met Gly Gly Thr Pro Asn Tyr Ala Gln Lys Phe Gln Gly Arg Val Thr
    50                  55                  60

Ile Thr Ala Gly Thr Trp Gly Lys Ser Thr Ala Thr Ile Ser Gly Leu
65              70                  75                  80

Lys Pro Gly Val Asp Tyr Thr Ile Thr Val Tyr Arg Lys Gly Ser Asp
                85                  90                  95
```

```
Arg Leu Ser Asp Asn Asp Pro Ser Ser Lys Pro Ile Ser Ile Asn Tyr
            100                 105                 110
Arg Thr Glu Ile
        115

<210> SEQ ID NO 19
<211> LENGTH: 118
<212> TYPE: PRT
<213> ORGANISM: Artificial Sequence
<220> FEATURE:
<223> OTHER INFORMATION: Synthetic Infold Peptide

<400> SEQUENCE: 19

Met Arg Asp Leu Glu Val Val Ala Ala Thr Pro Thr Ser Leu Leu Ile
1               5                   10                  15

Ser Trp Asp Ala Pro Val Thr Thr Val Ser Thr Tyr Tyr Ile Ile Glu
            20                  25                  30

Met Ser Glu Thr Asn Ala Pro Trp Thr Val Glu Phe Thr Val Ser Thr
        35                  40                  45

Met Gly Gly Thr Pro Asn Tyr Ala Gln Lys Phe Gln Gly Arg Val Thr
    50                  55                  60

Ile Thr Ala Gly Thr Trp Gly Lys Ser Thr Ala Ile Ser Gly Leu
65                  70                  75                  80

Lys Pro Gly Val Asp Tyr Thr Phe Arg Val Cys Ala Val Arg Lys Gly
                85                  90                  95

Ser Asp Arg Leu Ser Asp Asn Asp Pro Ser Ser Lys Pro Ile Ser Ile
            100                 105                 110

Asn Tyr Arg Thr Glu Ile
        115

<210> SEQ ID NO 20
<211> LENGTH: 98
<212> TYPE: PRT
<213> ORGANISM: Artificial Sequence
<220> FEATURE:
<223> OTHER INFORMATION: Synthetic Infold Peptide

<400> SEQUENCE: 20

Met Pro Pro Ala Val Gln His Leu Thr Ala Glu Val Thr Ala Asp Ser
1               5                   10                  15

Gly Glu Tyr Gln Val Leu Ala Arg Trp Arg Tyr Pro Lys Asp Arg Lys
            20                  25                  30

Tyr Gln Ser Phe Leu Gly Arg Leu Thr Val Thr Ala Asp Asp Gly Ser
        35                  40                  45

Glu Arg Leu Val Ser Thr Ala Arg Thr Arg Glu Thr Thr Tyr Arg Phe
    50                  55                  60

Thr Gln Leu Ala Leu Gly Asn Tyr Arg Leu Thr Val Arg Ala Val Asn
65                  70                  75                  80

Ala Trp Arg Gln Gln Gly Asp Pro Ala Ser Val Ser Phe Arg Ile Ala
                85                  90                  95

Ala Pro

<210> SEQ ID NO 21
<211> LENGTH: 98
<212> TYPE: PRT
<213> ORGANISM: Artificial Sequence
<220> FEATURE:
<223> OTHER INFORMATION: Synthetic Infold Peptide
```

```
<400> SEQUENCE: 21

Met Gly Pro Gln Gly Phe Pro Trp Arg Leu His Val Thr Gly Leu Thr
1               5                   10                  15

Thr Ser Thr Thr Glu Leu Ala Trp Asp Pro Pro Lys Tyr Ser Glu His
            20                  25                  30

Asn Ile Phe Ile Arg Ser Tyr Thr Val Val Phe Arg Asp Ile Asn Ser
        35                  40                  45

Gln Gln Glu Leu Gln Asn Ile Thr Asp Gly Arg Gly Glu Phe Thr Leu
    50                  55                  60

Thr Gly Leu Lys Pro Asp Thr Thr Tyr Asp Ile Lys Val Arg Ala Trp
65                  70                  75                  80

Thr Tyr Thr Arg Ser Gly Pro Leu Ser Pro Ser Ile Gln Ser Arg Thr
                85                  90                  95

Met Pro

<210> SEQ ID NO 22
<211> LENGTH: 196
<212> TYPE: PRT
<213> ORGANISM: Artificial Sequence
<220> FEATURE:
<223> OTHER INFORMATION: Synthetic Infold Peptide

<400> SEQUENCE: 22

Met Glu His Pro Val Ala Thr Leu Ser Thr Val Glu Arg Arg Ala Ile
1               5                   10                  15

Gln Leu Thr Trp Asp Ala Pro Val Thr Thr Ser Ser Arg Arg Tyr Ile
            20                  25                  30

Leu Glu Met Ser Glu Asn Asn Ala Pro Trp Thr Val Leu Leu Thr Val
        35                  40                  45

Pro Gly Phe Met Gly Gly Lys Thr Ser Val Thr Val Lys Gly Leu Val
    50                  55                  60

Pro Ala Arg Ser Tyr Gln Phe Arg Leu Ser Ala Val Asn Tyr Val Gly
65                  70                  75                  80

Lys Gly Gln Tyr Ser Lys Asp Thr Glu Arg Val Ser Leu Pro Glu Glu
                85                  90                  95

Pro Pro Thr Ala Pro Pro Gln Asn Val Ile Ala Ser Gly Arg Thr Asn
            100                 105                 110

Gln Ser Ile Met Ile Gln Trp Gln Pro Pro Glu Ser His Gln Asn
        115                 120                 125

Gly Ile Leu Lys Gly Tyr Ile Ile Arg Tyr Asn Asn Ala Gly Asn Pro
    130                 135                 140

Val Gly Tyr Gln Phe Lys Asn Ile Thr Asp Ala Asp Val Asn Asn Leu
145                 150                 155                 160

Leu Leu Glu Asp Leu Thr Ser Gly Thr Asn Tyr Glu Ile Glu Val Ala
                165                 170                 175

Ala Tyr Asn Ser Ala Gly Leu Gly Val Tyr Ser Ser Lys Val Thr Glu
            180                 185                 190

Trp Thr Leu Gln
        195

<210> SEQ ID NO 23
<211> LENGTH: 220
<212> TYPE: PRT
<213> ORGANISM: Artificial Sequence
<220> FEATURE:
<223> OTHER INFORMATION: Synthetic Infold Peptide
```

<400> SEQUENCE: 23

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Met Asp Thr
            20                  25                  30

Tyr Ile His Trp Val Arg Gln Ala Pro Gly Lys Gly Leu Glu Trp Val
        35                  40                  45

Ala Arg Ile Phe Pro Leu Phe Gly Tyr Thr Arg Tyr Ala Asp Ser Val
    50                  55                  60

Lys Gly Arg Phe Thr Ile Ser Ala Arg Leu Trp Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Arg Lys Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Val Glu Pro
    210                 215                 220
```

<210> SEQ ID NO 24
<211> LENGTH: 214
<212> TYPE: PRT
<213> ORGANISM: Artificial Sequence
<220> FEATURE:
<223> OTHER INFORMATION: Synthetic Infold Peptide

<400> SEQUENCE: 24

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
                130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 25
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ser Ser Glu Val Thr Phe Ser Ser Phe
                20                  25                  30

Ala Ile Ser Trp Val Arg Gln Ala Pro Gly Lys Gly Leu Glu Trp Val
                35                  40                  45

Ala Gly Ile Ser Pro Met Phe Gly Thr Pro Asn Tyr Ala Asp Ser Val
    50                  55                  60

Lys Gly Arg Phe Thr Ile Ser Ala Asp Gln Ser Thr Arg Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Pro Ser Tyr Ile Cys Ser Gly Gly Thr Cys Val Phe Asp
                100                 105                 110

His Trp Gly Gln Gly Thr Leu Val Thr Val Ser
        115                 120

<210> SEQ ID NO 26
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ser Ser Glu Met Thr Met Gly Gly Ser
                20                  25                  30

Ala Ile Ser Trp Val Arg Gln Ala Pro Gly Lys Gly Leu Glu Trp Val
                35                  40                  45

Ala Gly Ile Ser Pro Met Phe Gly Thr Pro Asn Tyr Ala Asp Ser Val
    50                  55                  60

Lys Gly Arg Phe Thr Ile Ser Ala Asp Gln Ser Thr Arg Thr Ala Tyr
65                  70                  75                  80

Leu Gln Met Asn Ser Leu Arg Ala Glu Asp Thr Ala Val Tyr Tyr Cys
                85                  90                  95
```

Ala Arg Ser Pro Ser Tyr Ile Cys Ser Gly Gly Thr Cys Val Phe Asp
            100                 105                 110

His Trp Gly Gln Gly Thr Leu Val Thr Val Ser
            115                 120

<210> SEQ ID NO 27
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ser Ser Glu Met Thr Met Gly Gly Ser
            20                  25                  30

Ala Ile Ser Trp Val Arg Gln Ala Pro Gly Lys Gly Leu Glu Trp Val
        35                  40                  45

Ala Gly Ile Ser Pro Met Phe Gly Thr Pro Asn Tyr Ala Asp Ser Val
    50                  55                  60

Lys Gly Arg Phe Thr Ile Ser Ala Asp Gly Ser Ser Gly Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Leu Val Thr Val Ser
            115                 120

<210> SEQ ID NO 28
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ser Ser Glu Val Thr Phe Ser Ser Phe
            20                  25                  30

Ala Ile Ser Trp Val Arg Gln Ala Pro Gly Lys Gly Leu Glu Trp Val
        35                  40                  45

Ala Gly Ile Ser Pro Met Met Gly His Pro Asn Tyr Ala Asp Ser Val
    50                  55                  60

Lys Gly Arg Phe Thr Ile Ser Ala Asp Gln Ser Thr Arg Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Pro Ser Tyr Ile Cys Met Gln Met Thr Cys Val Phe Asp
            100                 105                 110

His Trp Gly Gln Gly Thr Leu Val Thr Val Ser
            115                 120

<210> SEQ ID NO 29
<211> LENGTH: 123
<212> TYPE: PRT
<213> ORGANISM: Artificial Sequence

```
<220> FEATURE:
<223> OTHER INFORMATION: Synthetic Infold Peptide

<400> SEQUENCE: 29

Glu Val Lys Leu Val Glu Ser Gly Gly Gly Leu Val Gln Pro Gly Gly
1               5                   10                  15

Ser Leu Arg Leu Ser Cys Ala Ser Ser Glu Val Thr Phe Ser Ser Phe
            20                  25                  30

Ala Leu Thr Trp Val Arg Gln Pro Pro Gly Lys Ala Met Glu Trp Val
        35                  40                  45

Ala Gly Ile Ser Pro Met Phe Gly Thr Pro Asn Tyr Ser Asp Ser Val
    50                  55                  60

Lys Gly Arg Phe Thr Ile Ser Ala Asp Gln Ser Thr Arg Thr Ala Tyr
65                  70                  75                  80

Leu Gln Met Asn Thr Leu Arg Ala Glu Asp Ser Ala Met Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Thr Val Thr Val Ser
        115                 120

<210> SEQ ID NO 30
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 30

Glu Val Lys Leu Val Glu Ser Gly Gly Gly Leu Val Gln Pro Gly Gly
1               5                   10                  15

Ser Leu Arg Leu Ser Cys Ala Ser Ser Glu Met Thr Met Gly Gly Ser
            20                  25                  30

Ala Leu Thr Trp Val Arg Gln Pro Pro Gly Lys Ala Met Glu Trp Val
        35                  40                  45

Ala Gly Ile Ser Pro Met Phe Gly Thr Pro Asn Tyr Ser Asp Ser Val
    50                  55                  60

Lys Gly Arg Phe Thr Ile Ser Ala Asp Gln Ser Thr Arg Thr Ala Tyr
65                  70                  75                  80

Leu Gln Met Asn Thr Leu Arg Ala Glu Asp Ser Ala Met Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Thr Val Thr Val Ser
        115                 120

<210> SEQ ID NO 31
<211> LENGTH: 122
<212> TYPE: PRT
<213> ORGANISM: Artificial Sequence
<220> FEATURE:
<223> OTHER INFORMATION: Synthetic Infold Peptide

<400> SEQUENCE: 31

Glu Val Lys Leu Val Glu Ser Gly Gly Gly Leu Val Gln Pro Gly Gly
1               5                   10                  15

Ser Leu Arg Leu Ser Cys Ala Ser Ser Glu Met Thr Met Gly Gly Ser
            20                  25                  30
```

Ala Leu Thr Trp Val Arg Gln Pro Gly Lys Ala Met Glu Trp Val
            35                  40                  45

Ala Gly Ile Ser Pro Met Phe Gly Thr Pro Asn Tyr Ser Asp Ser Val
 50                  55                  60

Lys Gly Arg Phe Thr Ile Ser Ala Asp Gly Ser Ser Gly Thr Ala Tyr
 65                  70                  75                  80

Leu Gln Met Asn Thr Leu Arg Ala Glu Asp Ser Ala Met Tyr Tyr Cys
                85                  90                  95

Ala Arg Ser Pro Ser Tyr Ile Cys Ser Gly Thr Cys Val Phe Asp
                100                 105                 110

His Trp Gly Gln Gly Thr Thr Val Thr Val
            115                 120

<210> SEQ ID NO 32
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 32

Glu Val Lys Leu Val Glu Ser Gly Gly Gly Leu Val Gln Pro Gly Gly
1               5                   10                  15

Ser Leu Arg Leu Ser Cys Ala Ser Ser Glu Val Thr Phe Ser Ser Phe
                20                  25                  30

Ala Leu Thr Trp Val Arg Gln Pro Gly Lys Ala Met Glu Trp Val
            35                  40                  45

Ala Gly Ile Ser Pro Met Met Gly His Pro Asn Tyr Ser Asp Ser Val
 50                  55                  60

Lys Gly Arg Phe Thr Ile Ser Ala Asp Gln Ser Thr Arg Thr Ala Tyr
 65                  70                  75                  80

Leu Gln Met Asn Thr Leu Arg Ala Glu Asp Ser Ala Met Tyr Tyr Cys
                85                  90                  95

Ala Arg Ser Pro Ser Tyr Ile Cys Met Gln Met Thr Cys Val Phe Asp
                100                 105                 110

His Trp Gly Gln Gly Thr Thr Val Thr Val Ser
            115                 120

<210> SEQ ID NO 33
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 33

Glu Val Lys Leu Val Glu Ser Gly Gly Gly Leu Val Gln Pro Gly Gly
1               5                   10                  15

Ser Leu Arg Leu Ser Cys Ala Ser Ser Glu Val Thr Phe Ser Ser Phe
                20                  25                  30

Ala Leu Thr Trp Val Arg Gln Pro Gly Lys Ala Met Glu Trp Val
            35                  40                  45

Ala Gly Ile Ser Pro Met Phe Gly Thr Pro Asn Tyr Ser Asp Ser Val
 50                  55                  60

Lys Gly Arg Phe Thr Ile Ser Ala Asp Gly Ser Ser Gly Thr Ala Tyr
 65                  70                  75                  80

Leu Gln Met Asn Thr Leu Arg Ala Glu Asp Ser Ala Met Tyr Tyr Cys
                85                  90                  95

-continued

Ala Arg Ser Pro Ser Tyr Ile Cys Ser Gly Gly Thr Cys Val Phe Asp
            100                 105                 110

His Trp Gly Gln Gly Thr Thr Val Thr Val Ser
        115                 120

<210> SEQ ID NO 34
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 34

Glu Val Lys Leu Val Glu Ser Gly Gly Gly Leu Val Gln Pro Gly Gly
1               5                   10                  15

Ser Leu Arg Leu Ser Cys Ala Ser Ser Glu Val Thr Phe Ser Ser Phe
            20                  25                  30

Ala Leu Thr Trp Val Arg Gln Pro Pro Gly Lys Ala Met Glu Trp Val
        35                  40                  45

Ala Gly Ile Ser Pro Met Phe Gly Thr Pro Asn Tyr Ser Asp Ser Val
    50                  55                  60

Lys Gly Arg Phe Thr Ile Ser Ala Asp Gln Ser Thr Arg Thr Ala Tyr
65                  70                  75                  80

Leu Gln Met Asn Thr Leu Arg Ala Glu Asp Ser Ala Met Tyr Tyr Cys
                85                  90                  95

Ala Arg Ser Pro Ser Tyr Ile Cys Met Gln Met Thr Cys Val Phe Asp
            100                 105                 110

His Trp Gly Gln Gly Thr Thr Val Thr Val Ser
        115                 120

<210> SEQ ID NO 35
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 35

Glu Val Lys Leu Val Glu Ser Gly Gly Gly Leu Val Gln Pro Gly Gly
1               5                   10                  15

Ser Leu Arg Leu Ser Cys Ala Ser Ser Glu Val Thr Phe Ser Ser Phe
            20                  25                  30

Ala Leu Thr Trp Val Arg Gln Pro Pro Gly Lys Ala Met Glu Trp Val
        35                  40                  45

Ala Gly Ile Ser Pro Met Met Gly His Pro Asn Tyr Ser Asp Ser Val
    50                  55                  60

Lys Gly Arg Phe Thr Ile Ser Ala Asp Gln Ser Thr Arg Thr Ala Tyr
65                  70                  75                  80

Leu Gln Met Asn Thr Leu Arg Ala Glu Asp Ser Ala Met Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Thr Val Thr Val Ser
        115                 120

<210> SEQ ID NO 36
<211> LENGTH: 123
<212> TYPE: PRT

```
<213> ORGANISM: Artificial Sequence
<220> FEATURE:
<223> OTHER INFORMATION: Synthetic Infold Peptide

<400> SEQUENCE: 36

Glu Val Lys Leu Val Glu Ser Gly Gly Gly Leu Val Gln Pro Gly Gly
1               5                   10                  15

Ser Leu Arg Leu Ser Cys Ala Ser Ser Glu Met Thr Met Gly Gly Ser
            20                  25                  30

Ala Leu Thr Trp Val Arg Gln Pro Pro Gly Lys Ala Met Glu Trp Val
        35                  40                  45

Ala Gly Ile Ser Pro Met Phe Gly Thr Pro Asn Tyr Ser Asp Ser Val
    50                  55                  60

Lys Gly Arg Phe Thr Ile Ser Ala Asp Gln Ser Thr Arg Thr Ala Tyr
65                  70                  75                  80

Leu Gln Met Asn Thr Leu Arg Ala Glu Asp Ser Ala Met Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Thr Val Thr Val Ser
        115                 120

<210> SEQ ID NO 37
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 37

Glu Val Lys Leu Val Glu Ser Gly Gly Gly Leu Val Gln Pro Gly Gly
1               5                   10                  15

Ser Leu Arg Leu Ser Cys Ala Ser Ser Glu Met Thr Met Gly Gly Ser
            20                  25                  30

Ala Leu Thr Trp Val Arg Gln Pro Pro Gly Lys Ala Met Glu Trp Val
        35                  40                  45

Ala Gly Ile Ser Pro Met Phe Gly Thr Pro Asn Tyr Ser Asp Ser Val
    50                  55                  60

Lys Gly Arg Phe Thr Ile Ser Ala Asp Gly Ser Ser Gly Thr Ala Tyr
65                  70                  75                  80

Leu Gln Met Asn Thr Leu Arg Ala Glu Asp Ser Ala Met Tyr Tyr Cys
                85                  90                  95

Ala Arg Ser Pro Ser Tyr Ile Cys Ser Gly Gly Thr Cys Val Phe Asp
            100                 105                 110

His Trp Gly Gln Gly Thr Thr Val Thr Val Ser
        115                 120

<210> SEQ ID NO 38
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 38

Glu Val Lys Leu Val Glu Ser Gly Gly Gly Leu Val Gln Pro Gly Gly
1               5                   10                  15

Ser Leu Arg Leu Ser Cys Ala Ser Ser Glu Val Thr Phe Ser Ser Phe
            20                  25                  30
```

```
Ala Leu Thr Trp Val Arg Gln Pro Gly Lys Ala Met Glu Trp Val
        35                  40                  45

Ala Gly Ile Ser Pro Met Met Gly His Pro Asn Tyr Ser Asp Ser Val
    50                  55                  60

Lys Gly Arg Phe Thr Ile Ser Ala Asp Gln Ser Thr Arg Thr Ala Tyr
 65                  70                  75                  80

Leu Gln Met Asn Thr Leu Arg Ala Glu Asp Ser Ala Met Tyr Tyr Cys
                85                  90                  95

Ala Arg Ser Pro Ser Tyr Ile Cys Met Gln Met Thr Cys Val Phe Asp
                100                 105                 110

His Trp Gly Gln Gly Thr Thr Val Thr Val Ser
                115                 120

<210> SEQ ID NO 39
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 39

Glu Val Lys Leu Val Glu Ser Gly Gly Gly Leu Val Gln Pro Gly Gly
 1               5                  10                  15

Ser Leu Arg Leu Ser Cys Ala Ser Ser Glu Met Thr Met Gly Gly Ser
                20                  25                  30

Ala Leu Thr Trp Val Arg Gln Pro Gly Lys Ala Met Glu Trp Val
        35                  40                  45

Ala Gly Ile Ser Pro Met Met Gly His Pro Asn Tyr Ser Asp Ser Val
    50                  55                  60

Lys Gly Arg Phe Thr Ile Ser Ala Asp Gln Ser Thr Arg Thr Ala Tyr
 65                  70                  75                  80

Leu Gln Met Asn Thr Leu Arg Ala Glu Asp Ser Ala Met Tyr Tyr Cys
                85                  90                  95

Ala Arg Ser Pro Ser Tyr Ile Cys Ser Gly Thr Cys Val Phe Asp
                100                 105                 110

His Trp Gly Gln Gly Thr Thr Val Thr Val Ser
                115                 120

<210> SEQ ID NO 40
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 40

Glu Val Lys Leu Val Glu Ser Gly Gly Gly Leu Val Gln Pro Gly Gly
 1               5                  10                  15

Ser Leu Arg Leu Ser Cys Ala Ser Ser Glu Met Thr Met Gly Gly Ser
                20                  25                  30

Ala Leu Thr Trp Val Arg Gln Pro Gly Lys Ala Met Glu Trp Val
        35                  40                  45

Ala Gly Ile Ser Pro Met Met Gly His Pro Asn Tyr Ser Asp Ser Val
    50                  55                  60

Lys Gly Arg Phe Thr Ile Ser Ala Asp Gln Ser Thr Arg Thr Ala Tyr
 65                  70                  75                  80

Leu Gln Met Asn Thr Leu Arg Ala Glu Asp Ser Ala Met Tyr Tyr Cys
```

```
                    85                  90                  95
Ala Arg Ser Pro Ser Tyr Ile Cys Met Gln Met Thr Cys Val Phe Asp
            100                 105                 110
His Trp Gly Gln Gly Thr Thr Val Thr Val Ser
            115                 120

<210> SEQ ID NO 41
<211> LENGTH: 123
<212> TYPE: PRT
<213> ORGANISM: Artificial Sequence
<220> FEATURE:
<223> OTHER INFORMATION: Synthetic Infold Peptide

<400> SEQUENCE: 41

Glu Val Lys Leu Val Glu Ser Gly Gly Leu Val Gln Pro Gly Gly
1               5                   10                  15
Ser Leu Arg Leu Ser Cys Ala Ser Ser Glu Met Thr Met Gly Gly Ser
            20                  25                  30
Ala Leu Thr Trp Val Arg Gln Pro Pro Gly Lys Ala Met Glu Trp Val
            35                  40                  45
Ala Gly Ile Ser Pro Met Met Gly His Pro Asn Tyr Ser Asp Ser Val
        50                  55                  60
Lys Gly Arg Phe Thr Ile Ser Ala Asp Gly Ser Ser Gly Thr Ala Tyr
65                  70                  75                  80
Leu Gln Met Asn Thr Leu Arg Ala Glu Asp Ser Ala Met Tyr Tyr Cys
                85                  90                  95
Ala Arg Ser Pro Ser Tyr Ile Cys Met Gln Met Thr Cys Val Phe Asp
            100                 105                 110
His Trp Gly Gln Gly Thr Thr Val Thr Val Ser
            115                 120
```

ENGINEERED POLYPEPTIDE AGENTS FOR TARGETED BROAD SPECTRUM INFLUENZA NEUTRALIZATION

RELATED APPLICATIONS

The present application claims priority to U.S. Provisional patent application Ser. No. 61/298,776, filed on Jan. 27, 2010, the entire disclosure of which is incorporated herein by reference. In accordance with 37 CFR 1.52(e)(5), a Sequence Listing in the form of a text file (entitled "Sequence Listing.txt," created on Jan. 26, 2011, and 49 kilobytes) is incorporated herein by reference in its entirety.

GOVERNMENT SUPPORT

The invention was made with government support under Grant No. R01 GM057073 awarded by the National Institutes of Health. The government has certain rights in the invention.

BACKGROUND OF THE INVENTION

Influenza virus is a global health threat that is responsible for over 300,000 deaths annually. The virus evades immune recognition by engaging in a combination of accelerated antigenic drift, domain reassortment, genetic recombination, and glycosylation based masking of its surface glycoproteins. This rapid mutation capability of the virus is particularly exacerbated in the context of the growing threat from the present H1N1 'swine flu' pandemic as well as the alarming worldwide spate in recent infections with highly pathogenic avian H5N1 'bird flu' influenza strains. (Khanna et al., *Journal of Biosciences*, 33(4):475, 2008, Soundararajan et al., *Nature Biotechnology* 27:510, 2009). Furthermore, two of the major flu pandemics of the last century originated from avian flu viruses that changed their genetic makeup to allow for human infection.

Given the high degree of unpredictability in evolution of these influenza viruses, there is a need for the development of cross-strain effective (universal or broad spectrum) anti-influenza prophylactics and therapeutics. Such universal or broad spectrum anti-influenza agents would augment the annual flu vaccines that are designed to target specific 'seasonal' viral strains in circulation. (Ekiert et al., *Science*, 324(5924):246, 2009 and Sui et al., *Nat Struct Mol Biol.* 16(3):265, 2009). The importance of such agents is highlighted by the emerging drug resistance to antivirals oseltamivir (TAMIFLU®)/zanamivir (RELENZA®) (NA-inhibitors) and Amantadine/Rimantadine (MP-2 inhibitors) (Collins et al., *Nature* 453:1258, Stouffer et al., Nature, 451:596, 2008, Pielak et al., *Proc. Natl. Acad. Sci. USA*, 106:7379, 2009). For instance, over 98% and 100% of H1N1 strains this season are resistant to oseltamivir (TAMIFLU®) and the adamantane derivatives (Amantadine/Rimantadine), respectively. Additionally, seasonal flu vaccines are developed based on predictions of the most virulent influenza strain. In some cases, these predictions are wrong, thereby making the seasonal flu vaccines less effective. For these reasons, there is a need for the development of broad spectrum vaccines and therapeutic agents that are effective in the treatment or the delay of onset of disease caused by influenza viruses, independent of subtype or clade. Of course, there is also significant value in agents that are effective against any influenza strain, and indeed there can be profound value in agents that are specific to one or a set of strains.

SUMMARY OF THE INVENTION

The present invention provides novel agents for inhibiting influenza infection. In some embodiments, the present invention provides agents that bind to an influenza virus (e.g., to the virus' HA polypeptide) and/or that bind the HA receptor. In some embodiments, the present invention provides novel agents for broad spectrum influenza neutralization.

In particular, the present invention provides polypeptide agents, termed "infold agents", that bind to particular regions on an hemagglutinin (HA) polypeptide. For example, the present invention provides infold agents that bind the membrane proximal epitope region (MPER) region of the HA polypeptide. In some embodiments, infold agents bind to the MPER region independent of HA glycosylation. In some embodiments, infold agents interact with one or more amino acid residues in the HA polypeptide, and/or with one or more glycans bound to the HA polypeptide. In some embodiments, infold agents bind N-linked glycans on the HA polypeptide. In some embodiments, infold agents bind MPER-proximal N-glycans on the HA polypeptide.

In some embodiments, infold agents bind HA receptors. In certain embodiments, infold agents bind sialylated glycans on HA receptors. In some embodiments, infold agents bind to sialylated glycans having umbrella topology. In certain embodiments, infold agents bind with high affinity and/or specificity to umbrella-topology glycans (e.g., as compared with binding to glycans of other topologies, such as cone-topology glycans).

In some embodiments, infold agents compete with hemagglutinin for binding to an HA receptor. In some embodiments, infold agents compete with HA for binding to umbrella-topology glycans.

In some embodiments, infold agents are characterized by a backbone fold structure selected and dimensioned to fit within a predetermined three-dimensional space (e.g., binding pocket) and to display selected "interaction residues" such that they are positioned in three-dimensional space within a designated distance from identified "target residues" in the HA polypeptide and/or HA receptor. In some embodiments, an infold agent is characterized by a first backbone fold structure selected and dimensioned to fit within an HA polypeptide binding site, and a second backbone fold structure selected and dimensioned to fit within an HA receptor binding site.

The present invention further provides various reagents and methods associated with infold agents including, for example, systems for identifying them, strategies for preparing them, antibodies that bind to them, and various diagnostic and therapeutic methods relating to them. Further description of certain embodiments of these aspects, and others, of the present invention, is presented below.

BRIEF DESCRIPTION OF THE DRAWING

FIG. 1. Presents approaches for achieving targeted and full (broad) spectrum influenza neutralization using a targeted broad spectrum molecule (Infold agent). (a) Infold agents that bind to HA MPER (red circle) and to HA receptors (e.g., to sialylated glycans on the HA receptors) (green circle); (b) Infold agent that bind to HA MPER (red circle), MPER-proximal N-glycan (black circle) and sialylated glycans on HA receptors (green circle); (c) Infold agent that bind to HA MPER (red circle); (d) Infold agent that bind to HA MPER (red circle) and MPER-proximal N-glycan (black circle).

FIG. 6. (Top) Binding of Infold-3 to non-glycosylated HA MPER. (Bottom) Infold-3 (red) binds to the N-glycosylated HA MPER (gray/wheat) by accommodating the N-glycan (green carbon) owing to its smaller volume and lack of the two additional strands relative to that of antibodies as shown in FIG. 3.

FIG. 12. Illustrates exemplary umbrella topologies. (A) Certain exemplary (but not exhaustive) N- and O-linked glycan structures that can adopt umbrella topologies. (B) Certain exemplary (but not exhaustive) O-linked glycan structures that can adopt umbrella topologies.

FIG. 13. Illustrates possible sets of infold agent interaction and/or binding residues selected and designed to interact and/or bind with the indicated target residues in an HA polypeptide. As shown, the HA polypeptide is an H1 HA polypeptide.

FIG. 20. Presents exemplary assessment of neutralizing activity of a particular infold agent (Infold-28) described herein using crystal violet.

DEFINITIONS

Affinity: As is known in the art, "affinity" is a measure of the tightness with a particular ligand (e.g., an HA polypeptide or infold agent) binds to its partner (e.g., and HA receptor). Affinities can be measured in different ways.

Amino acid: As used herein, "amino acid" refers to any natural or unnatural amino acid (see definitions of "natural amino acid" and "unnatural amino acid" below).

Antibody: As used herein, the term "antibody" is intended to include immunoglobulins and fragments thereof which are specifically reactive to the designated protein or peptide, or fragments thereof. Suitable antibodies include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibodies" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. Antibodies for use herein may be of any type (e.g., IgA, IgD, IgE, IgG, IgM).

Figure 14:
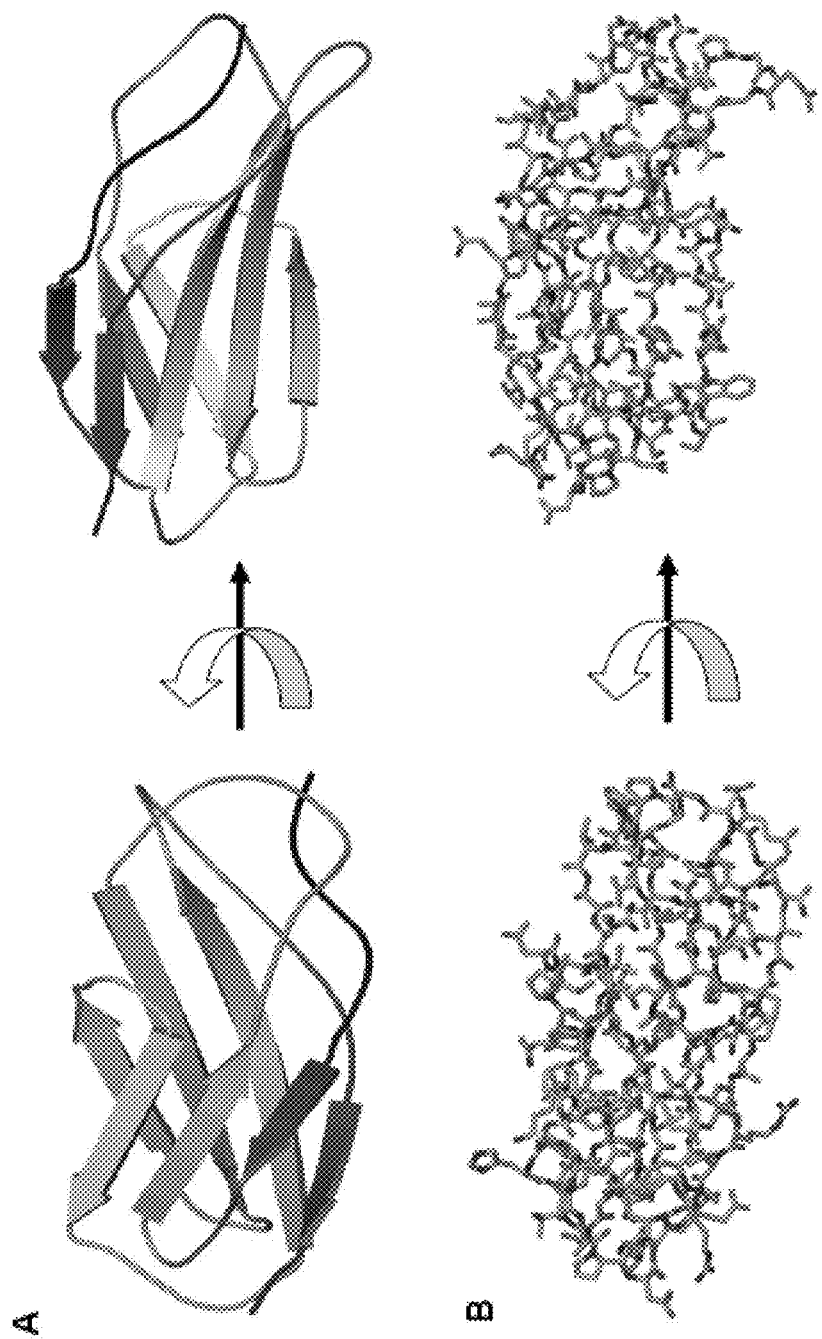
FIG. 14. Presents images of the structure of the PDB ID 2V5Y (protein data bank identification number) in ribbon and sticks representative models.

In some embodiments, an antibody is an antibody fragment. It will be appreciated that an antibody fragment may include a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. In some embodiments, an antibody fragment also includes any synthetic or genetically engineered protein that acts like an antibody by binding to a specific antigen to form a complex. For example, antibody fragments may include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region.

β-sandwich fold: A "β-sandwich fold" is a polypeptide domain that has between 5-12β-strands when its structure is determined experimentally or predicted computationally by any method, with a Cα RMSD (root mean square deviation) less than or equal to 6 angstroms upon superposition onto residues 260-355 (chain A) of the structure with the PBD ID 2V5Y (see FIG. 14). Further, such RMSD upon superposition of secondary structural regions (excluding loops) may be less than or equal to 5 Å. Infold domains constitute the "target recognition" domains of infold agents.

Binding: It will be understood that the term "binding", as used herein, typically refers to a non-covalent association between or among agents. In many embodiments herein, binding is addressed with respect to particular HA polypeptides, particular glycans (e.g., N-linked glycans, umbrella topology glycans or cone topology glycans) or particular HA receptors. It will be appreciated by those of ordinary skill in the art that such binding may be assessed in any of a variety of contexts. In some embodiments, binding is assessed with respect to the HA polypeptide. In some embodiments, binding is assessed with respect to glycans attached (e.g., covalently linked to) a carrier. In some such embodiments, the carrier is a polypeptide. In some embodiments, binding is assessed with respect to glycans attached to an HA receptor. In such embodiments, reference may be made to receptor binding or to glycan binding.

Binding site: The term "binding site", as used herein, refers to a region of a target polypeptide, formed in three-dimensional space, that includes the interaction residues of the target polypeptide. As will be understood by those of ordinary skill in the art, a binding site may include residues that are adjacent to one another on a linear chain, and/or that are distal to one another on a linear chain but near to one another in three-dimensional space when the target polypeptide is folded. A binding site may comprise amino acid residues and/or saccharide residues.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Broad spectrum: As used herein, the phrase "broad spectrum" refers to infold agents that bind a variety of HA polypeptides from different influenza virus strains. In some embodiments, broad spectrum infold agents bind to a plurality of different HA polypeptides. Exemplary such HA polypeptides include, H1, H2, H3, H4, H5, H6, H7, H8, H9, H10, H11, H12, H13, H14, H15, and/or H16 polypeptides, or combinations thereof. In some embodiments, provided infold agents are broad spectrum in that they bind to HA polypeptides from at least two different clades or clusters of virus. In some embodiments provided infold agents are broad spectrum in that they bind to HA polypeptides from all known clades of virus. In some embodiments, provided infold agents are broad spectrum in that they bind to HA polypeptides from group 1 and group 2 influenza viruses. In some embodiments, broad spectrum refers to HA polypeptides that mediate infection of particular hosts, e.g., avian, camel, canine, cat, civet, equine, human, leopard, mink, mouse, seal, stone martin, swine, tiger, whale, etc.

Candidate substrate: As used herein, the phrase "candidate substrate" refers to the substrates of one or more infold agents. In some embodiments, candidate substrates include but are not limited to polypeptides and saccharides. In some embodiments, candidate substrates include regions of HA polypeptides, the MPER region of HA-polypeptides, N-glycans on HA polypeptides, HA receptors, sialylated HA receptors, glycans on sialylated HA receptors and/or umbrella topology glycans on sialylated HA receptors.

Characteristic portion: As used herein, the phrase a "characteristic portion" of a protein or polypeptide is one that contains a continuous stretch of amino acids, or a collection of continuous stretches of amino acids, that together are characteristic of a protein or polypeptide. Each such continuous stretch generally will contain at least two amino acids. Furthermore, those of ordinary skill in the art will appreciate that typically at least 5, 10, 15, 20 or more amino acids are required to be characteristic of a protein. In general, a characteristic portion is one that, in addition to the sequence identity specified above, shares at least one functional characteristic with the relevant intact protein.

Characteristic sequence: A "characteristic sequence" is a sequence that is found in all members of a family of polypeptides or nucleic acids, and therefore can be used by those of ordinary skill in the art to define members of the family.

Combination Therapy: The term "combination therapy", as used herein, refers to those situations in which two or more different agents are administered in overlapping regimens so that the subject is simultaneously exposed to both agents.

Figure 10:
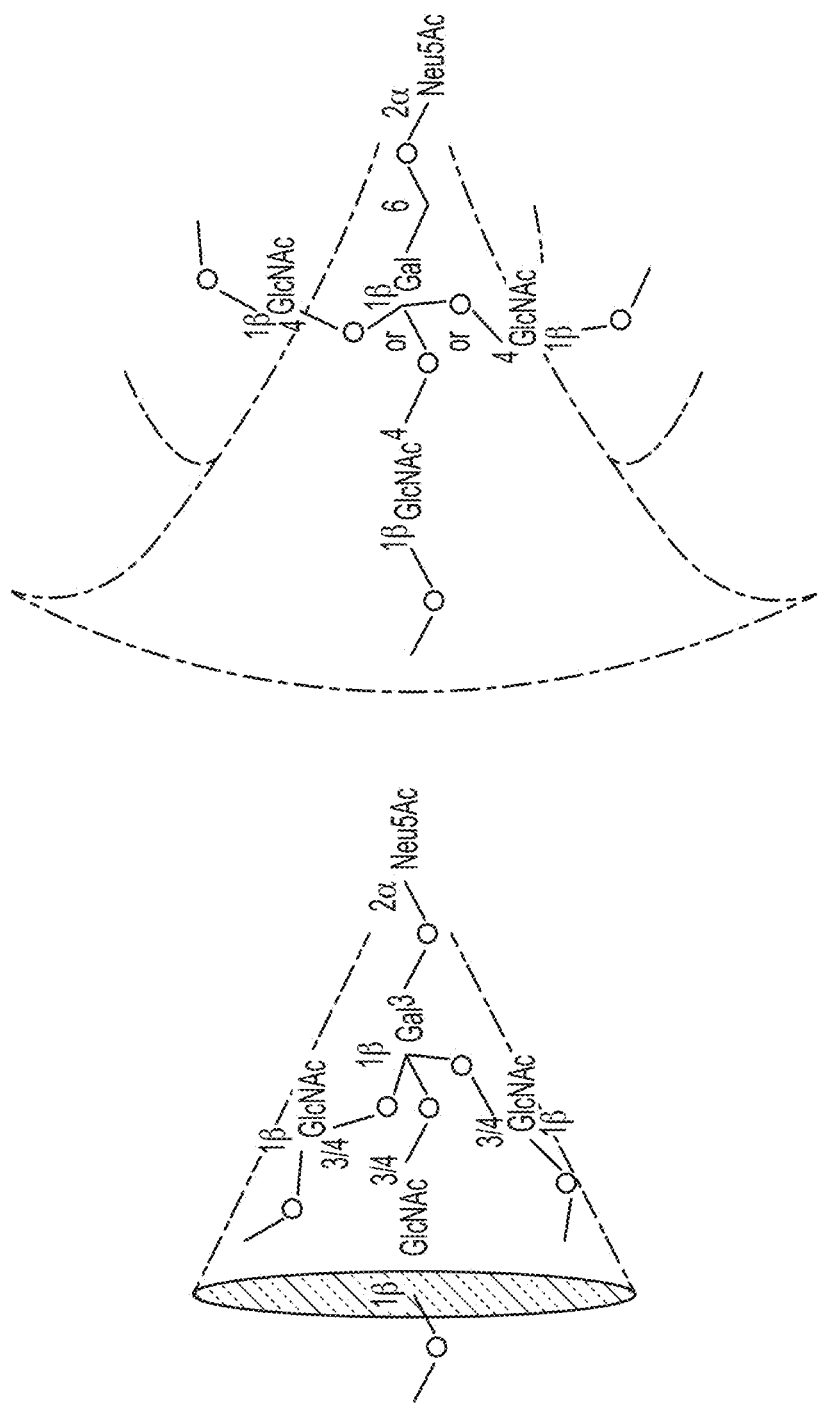
FIG. 10. Presents framework for understanding glycan receptor specificity. α2,3- and/or α2,6-linked glycans can adopt different topologies. It is believed that the ability of an HA polypeptide to bind to certain of these topologies confers upon it the ability to mediate infection of different hosts, for example in humans. The present invention refers to two particularly relevant topologies, a "cone" topology (left panel) and an "umbrella" topology (right panel). The cone topology can be adopted by α2,3- and/or α2,6-linked glycans, and is typical of short oligosaccharides or branched oligosaccharides attached to a core (although this topology can be adopted by certain long oligosaccharides). The umbrella topology can only be adopted by α2,6-linked glycans (presumably due to the increased conformational plurality afforded by the extra C5-C6 bond that is present in the α2,6 linkage), and is predominantly adopted by long oligosaccharides or branched glycans with long oligosaccharide branches, particularly containing the motif Neu5Acα2,6Galβ1-3/4GlcNAc.

Cone topology: The phrase "cone topology" is used herein to refer to a 3-dimensional arrangement adopted by certain glycans and in particular by glycans on HA receptors. As illustrated in FIG. 10, the cone topology can be adopted by α2,3 sialylated glycans or by α2,6 sialylated glycans, and is typical of short oligonucleotide chains, though some long oligonucleotides can also adopt this conformation. The cone topology is characterized by the glycosidic torsion angles of Neu5Acα2,3Gal linkage which samples three regions of minimum energy conformations given by $\phi$ (C1-C2-O-C3/C6) value of around −60, 60 or 180 and $\psi$ (C2-O-C3/C6-

Figure 11:
FIG. 11. Illustrates exemplary cone topologies. This Figure illustrates certain exemplary (but not exhaustive) glycan structures that adopt cone topologies.

H3/C5) samples −60 to 60. FIG. 11 presents certain representative (though not exhaustive) examples of glycans that adopt a cone topology.

Direct-binding amino acids: As used herein, the phrase "direct-binding amino acids" refers to amino acids residues that interact directly with a binding partner (e.g., one or more amino acids, glycans, etc.). Interaction residues are typically direct-binding amino acids.

Engineered: The term "engineered", as used herein, describes a polypeptide whose amino acid sequence has been selected by man. For example, an engineered infold agent has an amino acid sequence that was selected based on preferences for corresponding amino acids at particular sites of protein-protein interactions. In some embodiments, an engineered infold sequence has an amino acid sequence that differs from the amino acid sequence of HA polypeptides included in the NCBI database.

Hemagglutinin (HA) polypeptide: As used herein, the term "hemagglutinin polypeptide" (or "HA polypeptide") refers to a polypeptide whose amino acid sequence includes at least one characteristic sequence of HA. A wide variety of HA sequences from influenza isolates are known in the art; indeed, the National Center for Biotechnology Information (NCBI) maintains a database (ncbi.nlm.nih.gov/genomes/FLU/FLU) that, as of the filing of the present application included 9796 HA sequences. Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides; or of HA polypeptides that mediate infection of particular hosts, e.g., avian, camel, canine, cat, civet, environment, equine, human, leopard, mink, mouse, seal, stone martin, swine, tiger, whale, etc. For example, in some embodiments, an HA polypeptide includes one or more characteristic sequence elements found between about residues 97 and 185, 324 and 340, 96 and 100, and/or 130-230 of an HA protein found in a natural isolate of an influenza virus. In some embodiments the HA polypeptide is comprised of the HA-1 (head) and the HA-2 (stalk) domains of HA. In some embodiments, the HA polypeptide includes the characteristic sequence element from the membrane proximal epitope region (MPER) of HA. In some embodiments, a region of the HA polypeptide is glycosylated. In some embodiments, a region of the HA polypeptide is non-glycosylated.

In combination: The phrase "in combination", as used herein, refers to agents that are simultaneously administered to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered at the same time, or in the same composition. Rather, so long as both (or more) agents remain in the subject's body, they are considered to be administered "in combination".

Infold agent: In general, the term "infold agent" is used herein to refer to a an agent binds to a selected binding site, which agent comprises a polypeptide. In many embodiments, an infold agent has a structure characterized by a "fold" backbone populated by interaction residues selected and arranged so that, when the infold agent is in the vicinity of the binding site, individual interaction residues are positioned within a preselected distance or volume of cognate target residues. In some embodiments an infold polypeptide is an engineered or designed polypeptide. In some embodiments, infold agents provided herein bind a hemagglutinin (HA) polypeptide. In some embodiments, infold agents bind to an HA polypeptide in its MPER region. In some embodiments, infold agents bind to an HA polypeptide MPER region independent of its glycosylation. For example, in some embodiments, infold agents are designed to be of appropriate size that their binding to an MPER region is not prevented by its glycosylation. In some embodiments, an infold agent binds to a glycosylated MPER region with an affinity that is at least 5%, 10%, 15%, 20%, 25%, 30%, 35%, 40%, 45%, 50%, 55%, 60%, 65%, 70%, 75%, 80%, 85%, 90% or more of its affinity for an otherwise identical non-glycosylated MPER region. In some embodiments, infold agents have volumetric sizes between 6000-120,000 Å3. In some embodiments, provided infold agents have a volumetric size that is equal to or less than the volumetric size of an antibody. In some embodiments, an infold agent has a total target epitope surface area of approximately 20×30=600 Å2. In some embodiments, the total target epitope surface area of an infold agent is less than about 10 Å2, 20 Å2, 30 Å2, 40 Å2, 50 Å2, 60 Å2, 70 Å2, 80 Å2, 85 Å2, 90 Å2, 95 Å2, 100 Å2, 105 Å2, 110 Å2, 115 Å2, 120 Å2, 125 Å2, 130 Å2, 135 Å2, 140 Å2, 145 Å2, 150 Å2, 151 Å2, 152 Å2, 153 Å2, 154 Å2, 155 Å2, 160 Å2, 165 Å2, 170 Å2, 175 Å2, 180 Å2, 185 Å2, 190 Å2, 195 Å2, 200 Å2, 210 Å2, 220 Å2, 230 Å2, 240 Å2, 250 Å2, 260 Å2, 270 Å2, 280 Å2, 290 Å2, 300 Å2, 310 Å2, 315 Å2, 320 Å2, 325 Å2, 330 Å2 or larger. In some embodiments, total target epitope surface area is less than about 200 Å2, about 175 Å2, about 150 Å2, about 125 Å2 or smaller. In many embodiments, infold agents have a length that is less than about 1000 amino acids. In some embodiments, infold agents have a length that is less than a maximum length of about 1000, 975, 950, 925, 900, 875, 850, 825, 800, 775, 750, 725, 700, 675, 650, 625, 600, 575, 550, 525, 500, 475, 450, 425, 400, 375, 350, 325, 300, 275, 250, 240, 230, 220, 210, 200, 190, 180, 170, 160, 150, 140, 130, 125, 120, 115, 110, 105, 100, 95, 90, 85, 80, 75, 70, 65, 60, 55, 50, 45, 40, 35, 30, 25, or 20 amino acids in length. In some embodiments, infold agents have a length that is greater than a minimum length of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or more amino acids in length. In some embodiments, infold agents have a length between any one of such minimum lengths and any one of such maximum lengths, so long as the maximum length is longer than the minimum length. In some particular embodiments, an infold agent has a length between about 20 and 500, or between 30 and 400, or between 40 and 300, or between 80 and 250 amino acids. In some embodiments, an infold agent has a length of about 84, 88, 93, 95, 98, 104, 106, 110, 111, 116, 119, 123, 124, 132, 212, 215, 244, or 245. In some embodiments, infold agents are comprised of natural amino acids. In other embodiments, infold agents comprise one or more unnatural amino acids. In some embodiments, infold agents are comprised of combinations of natural and unnatural amino acids. In some embodiments, an infold agent is comprised of one, two or more polypeptide chains that are covalently (e.g., by means of a linker) or non-covalently associated. In some embodiments, an infold agent may be linked to, or part of, a longer polypeptide chain (e.g., a complete antibody, serum albumin, or other carrier protein) so long as the infold agent retains its three-dimensional structure and arrangement for interaction. In some embodiments, infold agents may be appended to the N- or C-termini of another polypeptide sequence that is or is not an infold. In some embodiments, infold agents are incorporated into the sequence of another polypeptide that is or is not an infold, thereby separating the polypeptide sequence into two or more segments. In some embodiments, appending the infold to the N or C termini or within the sequence of another polypeptide that is or is not an infold may allow for at least one or more of the following: a decrease in immunogenicity, increased circulation lifetime, slower in vivo degradation, inciting local immune response, interaction with the immune system molecules, an increase in volume, an increase in affinity for the infold target(s), an increase in specificity for the infold target(s), or the use of other commonly used therapeutic/prophylactic delivery protocols. In some embodiments, appending an infold to the N or C termini or within the sequence of another polypeptide that is or is not an infold does not have a direct effect on binding of an infold agent to a target (e.g., an HA polypeptide, the MPER region of an HA polypeptide, N-glycans on an HA polypeptide, HA receptors or sialylated glycans on HA receptors).

In some embodiments, infold agents bind to their target binding sites by interaction with one or more target residues. In some embodiments, such target residues are amino acids, saccharides, or combinations thereof. In some embodiments the present invention provides infold agents that bind to an HA polypeptide, N-linked glycans on an HA polypeptide, an HA receptor, sialylated glycans on an HA receptor or various combinations thereof. In some embodiments, the present invention provides polypeptide agents comprising a first infold agent that binds to an HA polypeptide and a second infold agent that binds to the HA receptor. In some such embodiments, the polypeptide agent comprises a single polypeptide chain that comprises the first and second infold, optionally connected to one another by way of one or more linking amino acids. In some embodiments, an infold agent that binds to an HA receptor interacts with one or more glycans on the HA receptor. In some embodiments, infold agents bind sialylated glycans. In some embodiments, infold agents bind sialylated glycans having an umbrella-like topology. In certain embodiments, infold agents bind to umbrella-topology glycans with high affinity and/or specificity. In some embodiments, infold agents show a binding preference for umbrella-topology glycans as compared with glycans of other topologies (e.g., cone-topology glycans). In some embodiments, infold agents compete with HA for binding to HA receptors. In some embodiments, infold agents compete with HA for binding such that binding between the HA polypeptide and the HA receptor is reduced at least 1.5 fold, at least 2 fold, at least 3 fold, at least 4 fold, at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 16 fold, at least 17 fold, at least 18 fold, at least 19 fold, or at least 20 fold. In some embodiments, infold agents compete with HA for binding to glycans on HA receptors. In some embodiments, infold agents compete with HA for binding to umbrella-topology glycans. In some embodiments, an infold agent provided herein is an umbrella topology blocking agent. In some embodiments, an infold agent provided herein is an umbrella topology specific blocking agent. In some embodiments, an infold agent has a backbone fold structure populated by a plurality of direct binding amino acid residues (i.e., amino acid residues that make direct contacts with HA amino acids or glycans), and/or with HA receptor amino acids or glycan as described herein.

Interaction residues: The term "interaction residues", as used herein, refers to residues in an infold agent that are designed to interact with particular target residues in a target polypeptide. Specifically, interaction residues are selected and arranged within an infold agent sequence so that they will be displayed in three dimensional space within a predetermined distance (or volume) of identified target residues (e.g., upon binding, docking or other interaction assays). In many embodiments, interaction residues are direct-binding residues.

Isolated: The term "isolated", as used herein, refers to an agent or entity that has either (i) been separated from at least some of the components with which it was associated when initially produced (whether in nature or in an experimental setting); or (ii) produced by the hand of man. Isolated agents or entities may be separated from at least about 10%, 20%, 30%, 40%, 50%, 60%, 70%, 80%, 90%, or more of the other components with which they were initially associated. In some embodiments, isolated agents are more than 90%, 91%, 92%, 93%, 94%, 95%, 96%, 97%, 98%, 99% pure.

Long oligosaccharide: For purposes of the present disclosure, an oligosaccharide is typically considered to be "long" if it includes at least one linear chain that has at least four saccharide residues.

Natural amino acid: As used herein, the term "natural amino acid" refers to one of the naturally occurring twenty amino acids. Refer to Table 1 for a list of these amino acids.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, 92%, 93%, 94%, 95%, 96%, 97%, 98%< or 99% pure.

Short oligosaccharide: For purposes of the present disclosure, an oligosaccharide is typically considered to be "short" if it has fewer than 4, or certainly fewer than 3, residues in any linear chain.

Specificity: As is known in the art, "specificity" is a measure of the ability of a particular ligand (e.g., an infold agent) to distinguish its binding partner (e.g., a human HA receptor, and particularly a human upper respiratory tract HA receptor) from other potential binding partners (e.g., an avian HA receptor).

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids., and/or as having "polar" or "non-polar" side chains Substitution of one amino acid for another of the same type may often be considered a "homologous" substitution. Typical amino acid categorizations are summarized below in Table 1:

TABLE 1

Amino Acid Categorizations

| Amino Acid | Abbreviations | | Polarity | | Charge |
|---|---|---|---|---|---|
| Alanine | Ala | A | Nonpolar | neutral | 1.8 |
| Arginine | Arg | R | Polar | positive | −4.5 |
| Asparagine | Asn | N | Polar | neutral | −3.5 |
| Aspartic acid | Asp | D | Polar | negative | −3.5 |
| Cysteine | Cys | C | Nonpolar | neutral | 2.5 |
| Glutamic acid | Glu | E | Polar | negative | −3.5 |
| Glutamine | Gln | Q | Polar | neutral | −3.5 |
| Glycine | Gly | G | Nonpolar | neutral | −0.4 |
| Histidine | His | H | Polar | positive | −3.2 |
| Isoleucine | Ile | I | Nonpolar | neutral | 4.5 |
| Leucine | Leu | L | Nonpolar | neutral | 3.8 |
| Lysine | Lys | K | Polar | positive | −3.9 |
| Methionine | Met | M | Nonpolar | neutral | 1.9 |
| Phenylalanine | Phe | F | Nonpolar | neutral | 2.8 |
| Proline | Pro | P | Nonpolar | neutral | −1.6 |
| Serine | Ser | S | Polar | neutral | −0.8 |
| Threonine | Thr | T | Polar | neutral | −0.7 |
| Tryptophan | Trp | W | Nonpolar | neutral | −0.9 |
| Tyrosine | Tyr | Y | Polar | neutral | −1.3 |
| Valine | Val | V | Nonpolar | neutral | 4.2 |

TABLE 2

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Target polypeptide: A "target polypeptide", as that term is used herein, is a polypeptide with which an infold agent interacts. In some embodiments, a target polypeptide is an HA polypeptide. In some embodiments, a target polypeptide is an HA receptor polypeptide.

Target residue: A "target residue", as that term is used herein, is a residue within a target polypeptide with which an infold agent is designed to interact. Specifically, an infold agent is typically characterized by particular interaction residues selected and arranged (by virtue of being presented on the selected "fold" backbone) to be within a certain predetermined distance (or volume) of a target residue. In some embodiments, a target residue is or comprises an amino acid residue. In some embodiments, a target residue is or comprises a saccharide residue.

Therapeutic agent: As used herein, the phrase "therapeutic agent" refers to any agent that elicits a desired biological or pharmacological effect.

Treatment: As used herein, the term "treatment" refers to any method used to alleviate, delay onset, reduce severity or incidence, or yield prophylaxis of one or more symptoms or aspects of a disease, disorder, or condition. For the purposes of the present invention, treatment can be administered before, during, and/or after the onset of symptoms.

Umbrella topology: The phrase "umbrella topology" is used herein to refer to a 3-dimensional arrangement adopted by certain glycans and in particular by glycans on HA receptors. The present invention encompasses the recognition that binding to umbrella topology glycans is characteristic of HA polypeptides that mediate infection of human hosts. As illustrated in FIGS. 10 and 12, the umbrella topology is typically adopted only by α2,6 sialylated glycans, and is typical of long (e.g., greater than tetrasaccharide) oligosaccharides. In some embodiments, umbrella-topology glycans are glycans exhibiting a three-dimensional structure substantially similar to the structure presented in FIG. 10 (right panel). In some embodiments, umbrella-topology glycans are glycans which contact HA polypeptides via the interactions with specific amino acid residues. In some embodiments, glycan structural topology is classified based on parameter θ defined as angle between $C_2$ of Sia, $C_1$ of Gal, and $C_1$ of GlcNAc. Values of θ<100° represent cone-like topology adopted by α2,3 and short α2,6 glycans. Values of θ>110° represent umbrella-like topology, such as topology adopted by long α2,6 glycans. An example of umbrella topology is given by ϕ angle of Neu5Acα2,6Gal linkage of around −60. FIG. 12 presents certain representative (though not exhaustive) examples of glycans that can adopt an umbrella topology. The long α2,6 motifs presented in FIG. 12 includes Neu5Acα2,6 linked at the non-reducing end to a long chain (e.g., at least a trisaccharide) found as a part of biological N-linked glycans, O-linked glycans, and glycolipids. The boxed inset shows examples of the umbrella-topology long α2,6 glycan moieties that are found as a part of biological glycans that bind to high affinity with HA. In some embodiments, umbrella-topology glycans (e.g., at a site) comprise a greater proportion of long (e.g. multiple lactosamine units) α2,6 oligosaccharide branches than short α2,6 (e.g. single lactosamine) branches. In some embodiments, umbrella-topology glycans (e.g., at a site) comprise about 2-fold, about 3-fold, about 4-fold, about 5-fold, about 10-fold, about 20-fold, about 50-fold, or greater than about 50-fold more long α2,6 oligosaccharide branches than short α2,6 (e.g. single lactosamine) branches. In certain embodiments, the unique characteristic of HA interactions with umbrella-topology glycans and/or glycan decoys is the HA contact with a glycan comprising sialic acid (SA) and/or SA analogs at the non-reducing end. In some embodiments, chain length of the oligosaccharide is at least a trisaccharide (excluding the SA or SA analog). In certain embodiments, umbrella topology glycans are oligosaccharides of the following form:

Neu5Acα2,6Sug1-Sug2-Sug3 where:

(a) Neu5Ac α2,6 is typically (but not essentially) at the non-reducing end;
(b) Sug1:
(i) is a hexose (frequently Gal or Glc) or hexosamine (GlcNAc or GalNAc) in α or β configuration (frequently β- for N- and O-linked extension and α- in the case of GalNAcα- that is O-linked to glycoprotein);
(ii) no sugars other than Neu5Acα2,6 are attached to any of the non-reducing positions of Sug1 (except when Sug1 is GalNAcα- that is O-linked to the glycoprotein); and/or
(iii) non-sugar moieties such as sulfate, phosphate, guanidium, amine, N-acetyl, etc. can be attached to non-reducing positions (typically 6 position) of Sug1 (e.g., to improve contacts with HA);
(c) Sug2 and/or Sug3 is/are:
(i) hexose (frequently Gal or Glc) or hexosamine (GlcNAc or GalNAc) in α or β configuration (frequently β); and/or
(ii) sugars (such as Fuc) or non-sugar moieties such as sulfate, phosphate, guanidium, amine, N-acetyl, etc. can be attached to non-reducing positions of Sug2, Sug3, and/or Sug4;
(d) Linkage between any two sugars in the oligosaccharide apart from Neu5Acα2,6 linkage can be 1-2, 1-3, 1-4, and/or 1-6 (typically 1-3 or 1-4); and/or
(e) Structure where Neu5Acα2,6 is linked GalNAcα that is O-linked to the glycoprotein and additional sugars are linked to the non-reducing end of GalNAcα for example
(i) Neu5Acα2,6(Neu5Acα2,3Galβ1-3)GalNAcα-
(ii) Neu5Acα2,6(Galβ1-3)GalNAcα-

Unnatural amino acid: As used herein, the term "unnatural amino acid" refers to any amino acid, modified amino acid, and/or amino acid analogue that is not one of the 20 naturally occurring amino acids. Refer to U.S. Pat. No. 7,045,337, U.S. Pat. No. 7,385,028, and U.S. Pat. No. 7,332,571, the entire disclosures of which are incorporated herein by reference. As used herein, "unnatural amino acid" also encompasses chemically modified amino acids, including but not limited to salts, amino acid derivatives (such as amides), and/or substitutions. Amino acids, including carboxy- and/or amino-terminal amino acids in peptides, can be modified by peglyation, methylation, amidation, acetylation, and/or substitution with other chemical groups that do not adversely affect the activity of the infold agent. Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Universal anti-influenza agent: As used herein, the term "universal anti-influenza agent" refers to an agent that has broad-spectrum neutralization across influenza virus strains, groups, clades, and clusters (see definitions of "broad spectrum" above and FIG. 19).

Vaccination: As used herein, the term "vaccination" refers to the administration of a composition intended to generate an immune response, for example to a disease-causing agent. For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

Variant: As used herein, the term "variant" is a relative term that describes the relationship between a particular polypeptide (e.g., HA polypeptide) of interest and a "parent" polypeptide to which its sequence is being compared. A polypeptide of interest is considered to be a "variant" of a parent polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, 20, 19, 18, 17, 16, 15, 14, 13, 10, 9, 8, 7, 6, and commonly are fewer than about 5, 4, 3, or 2 residues. In some embodiments, the parent polypeptide is one found in nature. For example, a parent HA polypeptide may be one found in a natural (e.g., wild type) isolate of an influenza virus (e.g., a wild type HA polypeptide).

Vector: As used herein, "vector" refers to a nucleic acid molecule capable of transporting another nucleic acid to which it has been linked. In some embodiment, vectors are capable of extra-chromosomal replication and/or expression of nucleic acids to which they are linked in a host cell such as a eukaryotic or prokaryotic cell. Vectors capable of directing the expression of operatively linked genes are referred to herein as "expression vectors."

Wild type: As is understood in the art, the phrase "wild type" generally refers to a normal form of a protein or nucleic acid, as is found in nature. For example, wild type HA polypeptides are found in natural isolates of influenza virus. A variety of different wild type HA sequences can be found in the NCBI influenza virus sequence database, ncbi.nlm.nih.gov/genomes/FLU/FLU.

DETAILED DESCRIPTION OF CERTAIN PARTICULAR EMBODIMENTS OF THE INVENTION

Hemagglutinin (HA) Polypeptide

Influenza viruses are RNA viruses which are characterized by a lipid membrane envelope containing two glycoproteins, a hemagglutinin (HA) polypeptide and a neuraminidase (NA) polypeptide, embedded in the membrane of the virus particular. There are 16 known HA polypeptide subtypes (H1, H2, H3, H4, H5, H6, H7, H8, H9, H10, H11, H12, H13, H14, H15, and H16) and 9 NA polypeptide subtypes (N1, N2, N3, N4, N5, N6, N7, N8, and N9), and different influenza strains are named based on the number of the strain's HA polypeptide and NA polypeptide subtypes, wherein there are different combinations of one HA polypeptide subtype combined with one NA polypeptide subtype (for example, H1N1, H1N2, H1N3, H1N4, H1N5, etc.).

Figure 19:
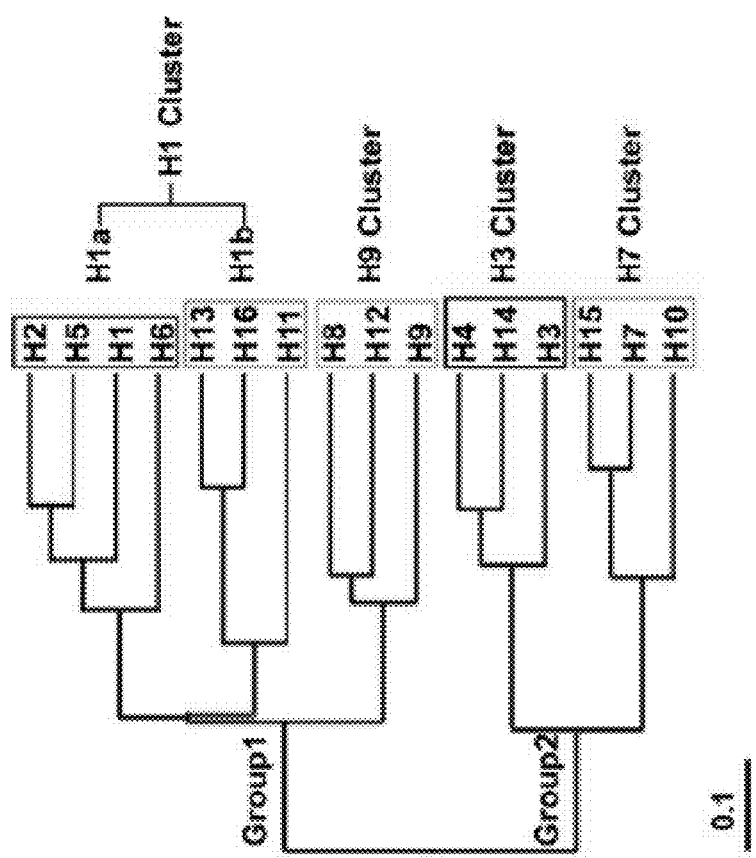
FIG. 19. Presents phylogenetic relationships among HA subtypes, showing divisions of influenza virus subtypes into groups, clades and clusters.

Based on comparisons of amino acid sequence identity and of crystal structures, the HA polypeptide subtypes have been divided into two main groups and four smaller clades, which is further divided into five clusters (FIG. 19). The different HA polypeptide subtypes do not necessarily share strong amino acid sequence identity, but the overall 3D structures of the different HA polypeptide subtypes are similar to one another, with several subtle differences that can be used for classification purposes. For example, the particular orientation of the membrane-distal subdomains in relation to a central α-helix is one structural characteristic commonly used to determine HA polypeptide subtype (Russell et al., *Virology*, 325:287, 2004).

Mature HA polypeptides are comprised of two domains, (1) a core HA-1 domain known as the sialic acid-binding domain, and (2) the transmembrane stalk of HA, known as HA-2 domain. HA-1 contains the binding site for glycans and it is thought that HA-1 is responsible for mediating binding of HA to the HA-receptor. HA-2 is responsible for presenting the HA-1 domain.

Figure 2:
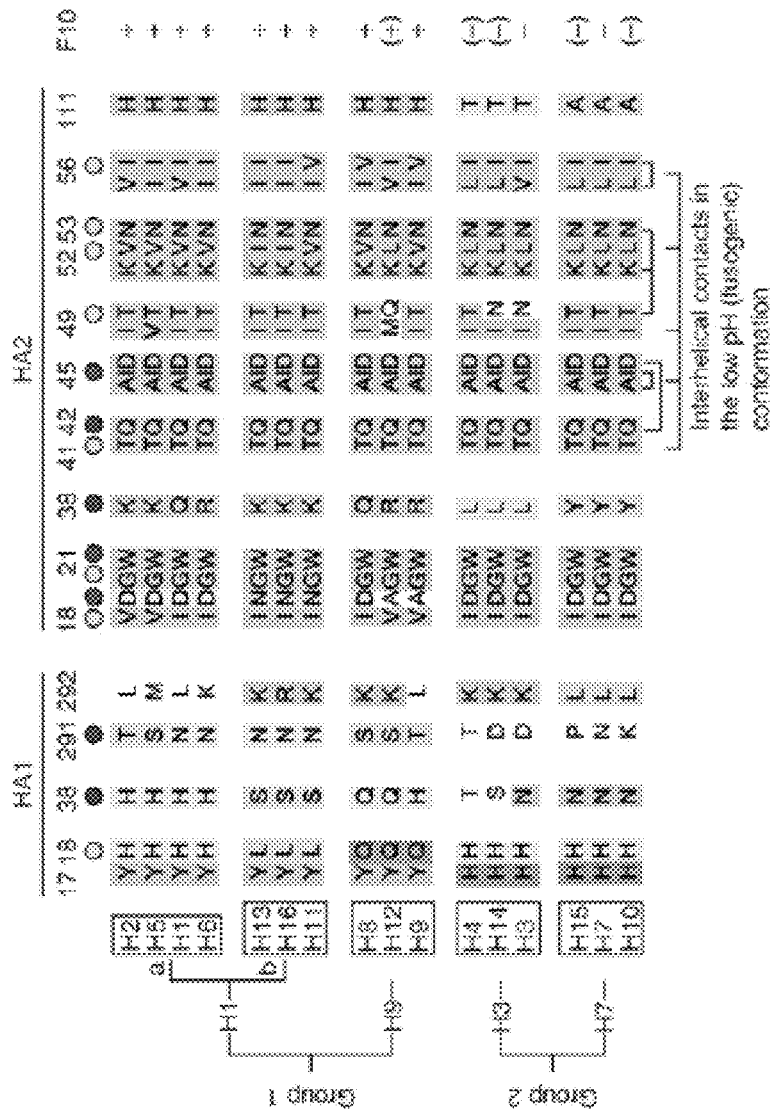
FIG. 2. Conservation of the membrane proximal epitope region (MPER) for group-1 and group-2 influenza strains (Stouffer et al., *Nature*, 451:596, 2008). The key MPER residues on HA-1 (globular head domain) and HA-2 (stalk domain) are shown and the prominent amino acids from each strain in these positions are colored according to the degree of cross-clade conservation (orange=most conserved positions).

Without wishing to be bound by any particular theory, analysis of HA sequences from all influenza subtypes showed a set of amino acids in the interface of the HA-1 (head) and HA-2 (stalk) domains that are well conserved and accessible to prospective therapeutic molecules (FIG. 13). Studies have also observed the excellent broad spectrum conservation of the HA-1/HA-2 interface membrane proximal epitope region (MPER) that includes the canonical α-helix and residues in its vicinity (Ekiert et al., *Science*, 324(5924):246, 2009; Sui et al., *Nat Struct Mol Biol.* 16(3): 265, 2009) (FIG. 2).

Figure 3:
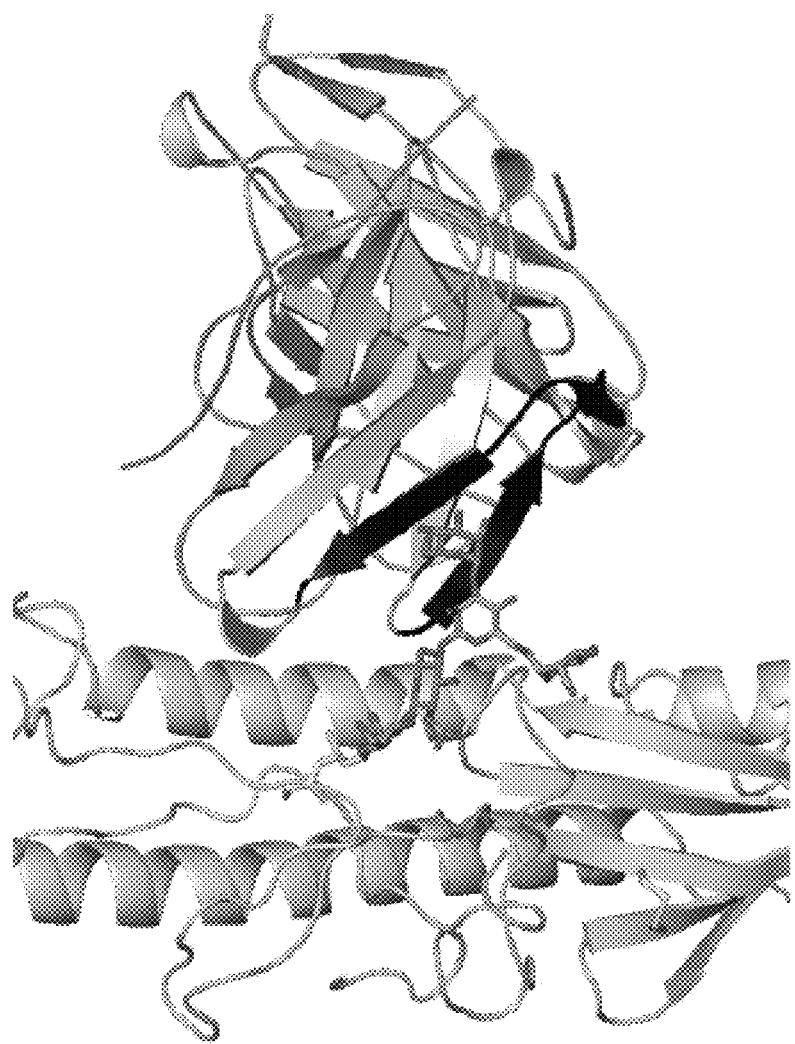
FIG. 3. Structural rationale for limitations of antibodies for N-glycosylated influenza HA MPER targeting. F10 antibody (pink) docked to H3 HA (wheat/gray) N-glycosylated at Asn-38 (green carbon) shows that the additional C' and C" beta-strands (black) that constitute two of the nine beta-strands in all antibody VH domains are responsible primarily for the steric hindrance to antibody binding.
Figure 4:
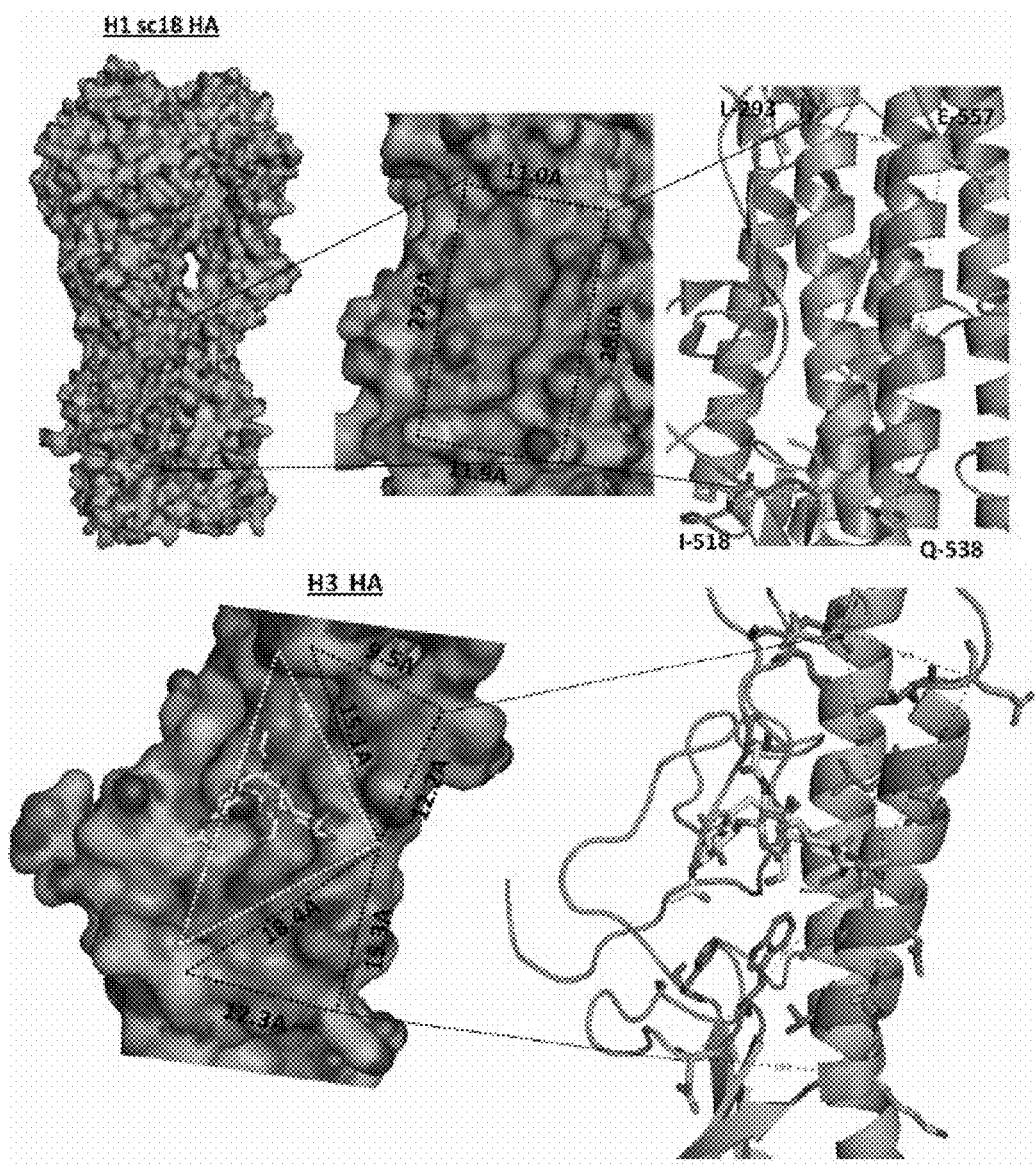
FIG. 4. Structural rationale for reduction of MPER area available for targeting on glycosylated HA. On non-glycosylated HA polypeptides (top), MPER area of $28*11.5{\sim}325$ $A^2$ is available for targeting, whereas a reduced MPER area of $0.5*(12.3*15.3+9.5*12.2){\sim}152$ $A^2$ is only available for binding on N-glycosylated HA polypeptides (bottom).

Antibodies including CR6261 FAb (Ekiert et al., *Science*, 324(5924):246, 2009), and F10 scFv (Sui et al., *Nat Struct Mol Biol.* 16(3):265, 2009) have been developed against the highly conserved membrane proximal epitope region (MPER) of the HA (FIG. 3). While these antibodies are successful in neutralization of the group-1 clade of the influenza-A strains (H1, H2, H5, H9), they are ineffective against the group-2 strains that are N-glycosylated in the proximity of their MPER (Ekiert et al., *Science*, 324(5924): 246, 2009; Sui et al., *Nat Struct Mol Biol.* 16(3):265, 2009). These group-2 strains include influenza-A H3, H7, and H10 that are glycosylated in Asn-38 of the N-terminal HA-1 domain, as well as the entire influenza-B clade of viruses that are glycosylated in Asn-238 of the C-terminal HA-1 domain. Without wishing to be bound by theory, we propose that the N-glycosylations prevent the large antibody-based molecules such as IgGs, mAbs, and scFvs from accessing the underlying epitope, thereby limiting their broad spectrum application (FIG. 4).

HA Receptors

HA polypeptides interact with the surface of cells by binding to a glycoprotein receptor, known as the HA receptor. Binding of an HA polypeptide to an HA receptor is predominantly mediated by N-linked glycans on the HA receptors. Specifically, HA polypeptides on the surface of flu virus particles recognizes sialylated glycans that are associated with HA receptors on the surface of the cellular host. After recognition and binding, the host cell engulfs the viral cell and the virus is able to replicate and produce many more virus particles to be distributed to neighboring cells.

HA polypeptides exists in the viral membrane as a homotrimer of one of 16 subtypes, termed H1-H16. Only three of these subtypes (H1, H2, and H3) have thus far become adapted for human infection. One reported characteristic of HA polypeptides that have adapted to infect humans (e.g., of HA polypeptides from the pandemic H1N1 (1918) and H3N2 (1967-68) influenza subtypes) is their ability to preferentially bind to α2,6 sialylated glycans in comparison with their avian progenitors that preferentially bind to α2,3 sialylated glycans (Skehel & Wiley, *Annu Rev Biochem*, 69:531, 2000; Rogers, & Paulson, *Virology*, 127: 361, 1983; Rogers et al., *Nature*, 304:76, 1983; Sauter et al., *Biochemistry*, 31:9609, 1992; Connor et al., *Virology*, 205: 17, 1994; Tumpey et al., *Science*, 310:77, 2005). Without wishing to be bound by any particular theory, it has been proposed that the ability to infect human hosts correlates less with binding to glycans of a particular linkage, and more with binding to glycans of a particular topology. We have specifically demonstrated that HA polypeptides that mediate infection of humans bind to umbrella topology glycans, often showing preference for umbrella topology glycans over cone topology glycans (even though cone-topology glycans may be α2,6 sialylated glycans) (See, for example, U.S. Ser. No. 12/348,266 filed Jan. 2, 2009, U.S. Ser. No. 12/301,126, filed Nov. 17, 2008, U.S. Ser. No. 61/018,783, filed Jan. 3, 2008, U.S. Ser. No. 11/969,040, filed Jan. 3, 2008, U.S. Ser. No. 11/893,171, filed Aug. 14, 2007, U.S. Ser. No. 60/837,868, filed on Aug. 14, 2006, U.S. Ser. No. 60/837,869, filed on August 14, and to PCT application PCT/US07/18160, filed Aug. 14, 2007, each of which is incorporated herein by reference).

Several crystal structures of HA polypeptides from H1 (human and swine), H3 (avian) and H5 (avian) subtypes bound to sialylated oligosaccharides (of both α2,3 and α2,6 linkages) are available and provide molecular insights into the specific amino acids that are involved in distinct interactions of the HA polypeptides with these glycans (Eisen et al., *Virology*, 232:19, 1997; Ha et al., *Proc Natl Acad Sci USA*, 98:11181, 2001; Ha et al., *Virology*, 309:209, 2003; Gamblin et al., *Science*, 303:1838, 2004; Stevens et al., *Science*, 303:1866, 2004; Russell et al., *Glycoconj J* 23:85, 2006; Stevens et al., *Science*, 312:404, 2006). Some crystal structures of exemplary HA-glycan interactions have been identified and are presented in Table 3:

TABLE 3

Crystal Structures of HA-Glycan Complexes

| Abbreviation (PDB ID) | Virus Strain | Glycan (with assigned coordinates) |
|---|---|---|
| ASI30_H1_23 (1RV0) | A/Swine/Iowa/30 (H1N1) | Neu5Ac |
| ASI30_H1_26 (1RVT) | A/Swine/Iowa/30 (H1N1) | Neu5Acα6Galβ4GlcNAcβ3Galβ4Glc |
| APR34_H1_23 (1RVX) | A/Puerto Rico/8/34 (H1N1) | Neu5Acα3Galβ4GlcNAc |
| APR34_H1_26 (1RVZ) | A/Puerto Rico/8/34 (H1N1) | Neu5Acα6Galβ4GlcNAc |
| ADU63_H3_23 (1MQM) | A/Duck/Ukraine/1/63 (H3N8) | Neu5Acα3Gal |
| ADU63_H3_26 (1MQN) | A/Duck/Ukraine/1/63 (H3N8) | Neu5Acα6Gal |
| AAI68_H3_23 (1HGG) | A/Aichi/2/68 (H3N2) | Neu5Acα3Galβ4Glc |
| ADS97_H5_23 (1JSN) | A/Duck/Singapore/3/97 (H5N3) | Neu5Acα3Galβ3GlcNAc |
| ADS97_H5_26(1JSO) | A/Duck/Singapore/3/97 (H5N3) | Neu5Ac |
| Viet04_H5 (2FK0) | A/Vietnam/1203/2004 (H5N1) | |

HA-α2,6 sialylated glycan complexes were generated by superimposition of the CA trace of the HA-1 subunit of ADU63_H3 and ADS97_H5 and Viet04_H5 on ASI30_H1_26 and APR34_H1_26 (H1). Although the structural complexes of the human A/Aichi/2/68 (H3N2) with α2,6 sialylated glycans are published (Eisen et al., 1997, *Virology*, 232: 19), their coordinates were not available in the Protein Data Bank. The SARF2 (123d.nciferf.gov/sarf2) program was used to obtain the structural alignment of the different HA-1 subunits for superimposition.

For example, the crystal structures of H5 (A/duck/Singapore/3/97) alone or bound to an α2,3 or an α2,6 sialylated oligosaccharide identifies certain amino acids that interact directly with bound glycans, and also amino acids that are one or more degree of separation removed (Stevens et al., *Proc Natl Acad Sci USA* 98:11181, 2001). In some cases, conformation of these residues is different in bound versus unbound states. For instance, Glu190, Lys193 and Gln226 all participate in direct-binding interactions and have different conformations in the bound versus the unbound state. The conformation of Asn186, which is proximal to Glu190, is also significantly different in the bound versus the unbound state.

Without wishing to be bound by any particular theory, it is thought that the HA receptors are modified by either α2,3 or α2,6 sialylated glycans near the receptor's HA polypeptide-binding site, and the type of linkage of the receptor-bound glycan can affect the conformation of the receptor's HA polypeptide-binding site, thus affecting the receptor's specificity for different HA polypeptides. For example, the glycan binding pocket of avian HA receptor is narrow. Without wishing to be bound by any particular theory, it has been proposed that this pocket binds to the trans conformation of α2,3 sialylated glycans, and/or to cone-topology glycans, whether α2,3 or α2,6 linked (FIGS. 10-12).

HA receptors in avian tissues, and also in human deep lung and gastrointestinal (GI) tract tissues are characterized by α2,3 sialylated glycan linkages, and furthermore are characterized by glycans, including α2,3 sialylated and/or α2,6 sialylated glycans, which predominantly adopt cone topologies. HA receptors having such cone-topology glycans may be referred to herein as CTHArs.

By contrast, human HA receptors in the bronchus and trachea of the upper respiratory tract are modified by α2,6 sialylated glycans. Unlike the α2,3 motif, the α2,6 motif has an additional degree of conformational freedom due to the C6-C5 bond (Russell et al., *Glycoconj J* 23:85, 2006). HA polypeptides that bind to such α2,6 sialylated glycans have a more open binding pocket to accommodate the diversity of structures arising from this conformational freedom. Moreover, according to the present invention, HA polypeptides may need to bind to glycans (e.g., α2,6 sialylated glycans) in an umbrella topology, and particularly may need to bind to such umbrella topology glycans with strong affinity and/or specificity, in order to effectively mediate infection of human upper respiratory tract tissues. HA receptors having umbrella-topology glycans may be referred to herein as UTHArs.

As a result of these spatially restricted glycosylation profiles, humans are not usually infected by viruses containing many wild type avian HA polypeptides (e.g., avian H5). Specifically, because the portions of the human respiratory tract that are most likely to encounter virus (i.e., the trachea and bronchi) lack receptors with cone glycans (e.g., α2,3 sialylated glycans, and/or short glycans) and wild type avian HA polypeptides typically bind primarily or exclusively to receptors associated with cone glycans (e.g., α2,3 sialylated glycans, and/or short glycans), humans rarely become infected with avian viruses. Only when in sufficiently close contact with virus that it can access the deep lung and/or gastrointestinal tract receptors having umbrella glycans (e.g., long α2,6 sialylated glycans) do humans become infected.

Infold Agents

Infold Agent Structure

As described herein, infold agents are, generally, polypeptide agents that bind to a selected binding site. In many embodiments, an infold agent has a structure characterized by a "fold" backbone populated by interaction residues selected and arranged so that, when the infold agent is in the vicinity of the binding site, individual interaction residues are positioned within a preselected distance or volume of cognate target residues.

A variety of polypeptide "fold" structures, appropriately utilized as infold agent backbone structures according to the present invention, are known in the art. That is, it is well known that linear chains of amino acids adopt discrete secondary and tertiary structures, so that amino acids that are proximal in space, but distal in sequence. For example, common secondary folds include α-helix, β-sheet, polyproline helix, $3_{10}$ helix and turns. Common tertiary folds include ferredoxin-like (4.45%), TIM-barrel (3.94%), P-loop containing nucleotide triphosphate hydrolase (3.71%), protein kinases (PK) catalytic domain (3.14%), NAD(P)-binding Rossmann-fold domains (2.80%), DNA: RNA-binding 3-helical bundle (2.60%), α-α superhelix (1.95%), S-adenosyl-L-methionine-dependent methyltransferase (1.92%), 7-bladed beta-propeller (1.85%), α:β-hydrolases (1.84%), PLP-dependent transferase (1.61%), adenine nucleotide α-hydrolase (1.59%), flavodoxin-like (1.49%), immunoglobulin-like β-sandwich (1.38%), and glucocorticoid receptor-like (0.97%), where the values in parentheses are the percentages of annotated proteins adopting the respective folds (see, for example, Zhang et al., Cellular and Molecular Life Sciences, 58:72, 2001).

In some embodiments, infold agents described herein have a fold backbone structure based on a protein selected from the group consisting of: the extracellular region of human tissue factor, tenascin, neuroglian, neural cell adhesion molecule 1 (NCAM), integrin beta-4 subunit, growth hormone receptor, erythropoietin (EPO) receptor, prolactin receptor, inerleukin-4 receptor alpha chain, beta-chain of GM-CSF receptors, beta-chain of IL-3 receptors, beta-chain of IL-5 receptors, granulocyte colony-stimulating factor (GC-SF) receptor, contactin 3 (KIAA1496), brother of CDO precursor (BOC), interferon-gamma receptor alpha chain, cytokine receptor gp130 cytokine-binding domains, interleukin-10 receptor 1 (IL-10R1), type 1 titin module, the p40 domain of interleukin-12 (IL-12 beta chain), interleukin-6 receptor alpha chain, interferon-alpha/beta receptor beta chain, KIAA1568 protein, KIAA0343 protein, KIAA1355 protein, ciliary neurotrophic factor receptor alpha, host cell factor 2 (HCF-2), ankyrin repeat domains 1 protein (FANK1), ephrin type B receptor 1, ephrin type A receptor 8, cytokine receptor common gamma chain, rim binding protein 2, interleukin-2 receptor beta chain, tenascin-X, receptor-type tyrosine-protein phosphatase delta (PTPRD), sidekick 2, neogenin down syndrome cell adhesion molecule-like protein 1 (DSCAML1), mysoin binding protein C (fast-type), receptor-type tyrosine-protein phosphatase F (PTPRF), hedgehog receptor iHog, ephrin type A receptor 1.

In some embodiments, infold agents described herein have an antibody fold backbone. Several infold agents exemplified herein (see, for example, Table 9, e.g., Infold-23 through Infold-40) have an antibody fold backbone. In some embodiments, infold agents described herein have a β-sandwich domain fold backbone.

Figure 9:
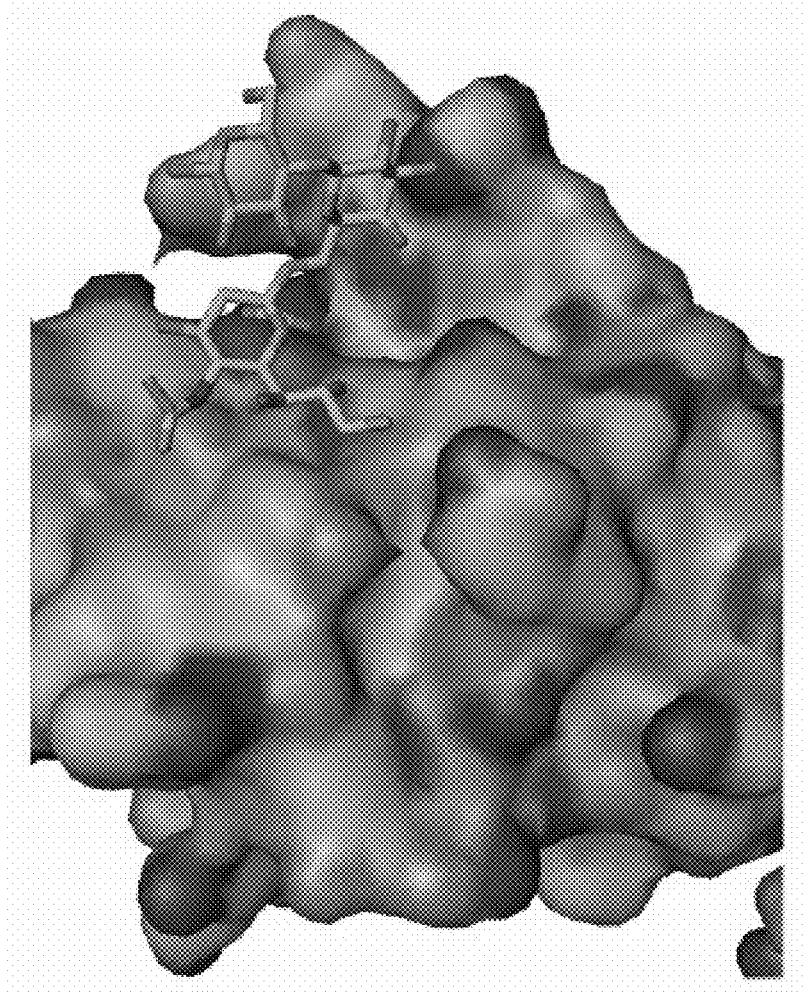
FIG. 9. Presents an example of an α2,6 sialylated glycan recognition motif, used in the design of Infold-9 and Infold-10 binding to α2,6 sialylated glycan HA receptors for targeted anti-influenza therapeutic delivery.

In some embodiments, inventive infold agents are characterized by the presence of interaction residues selected and arranged to interact with particular target residues in an HA polypeptide and/or an HA receptor. For Example, Tables 4 and 5 present certain representative target residue sets for HA polypeptides (glycosylated or nonglycosylated; Table 4) and for HA receptor (specifically HA receptor containing sialylated glycans; Table 5) also see FIGS. 5 and 9.

TABLE 4

HA Polypeptide Exemplary Target Residue Sets
(exemplified with H3 HA PBD ID 1HGG numbering)

| | |
|---|---|
| Set-T1 | Trp-21, Ile-48, Ile-45, Met-320 |
| Set-T2 | Val-20, Leu-38 |
| Set-T3 | Thr-37, Thr-41 |
| Set-T4 | His-18 |
| Set-T5 | Lys-121, Lys-39 |
| Set-T6 | Asp-19, Gln-42, Asp-46, Gln-47, Asn-49, Asn-53, Asn-38 |
| Set-T7 | Thr-318, Thr-40 |
| Set-T8 | Leu-52, Leu-42, Ile-56, Pro-293 |
| Set-T9 | His-56 |
| Set-T10 | Lys-58, Lys-292 |
| Set-T11 | Asn-290, Asp-291, Glu-57, Glu-61, Glu-280 |
| Set-T12 | Ser-279, Thr-59 |

HA Polypeptide Glycan Exemplary Target Residue Sets

| | |
|---|---|
| Set-T14 | N-glycan on HA polypeptides. In some embodiments, N-glycans on HA polypeptides are near or proximal to the MPER region |

TABLE 5

HA Receptor Exemplary Target Residue Sets

| | |
|---|---|
| Set-T13 | Sialic acid on HA receptor glycans |

In some embodiments, the present invention provides infold agents that contain interaction residues that bind to these target sets.

For example, Table 6 provides infold interaction residue sets that can be utilized in inventive infold agents designed to interact with HA polypeptides and/or with HA receptors according to the rules set forth in Table 7:

TABLE 6

Exemplary Infold Interaction Residue Sets

| | |
|---|---|
| Set-In1 | Ile, Leu, Val, Phe, Met, Trp, Tyr, Pro, His |
| Set-In2 | Val, Phe, Trp, Tyr, Asp, Arg, Lys |
| Set-In3 | Ile, Leu, Phe, Met, Trp, Tyr, His, Gln, Asp, Arg |
| Set-In4 | Asp, Glu, Phe, Met, Tyr, Trp |
| Set-In5 | Arg, Lys, His, Asn, Gln, Thr |
| Set-In6 | Tyr, Trp, Phe, His, Arg, Gln, Ser |
| Set-In7 | Tyr, Trp, Phe, Pro, Arg, Asp, His, Lys |

TABLE 7

Exemplary Infold Structures

| Target Residue Set | Infold Interaction Residues Presented within 5 Å of Target Residues During Binding or Upon Docking |
|---|---|
| Set-T1 | Set-In1 |
| Set-T2 | Set-In1 |
| Set-T3 | Set-In2 |
| Set-T4 | Set-In3 |
| Set-T5 | Set-In4 |
| Set-T6 | Set-In5 |
| Set-T7 | Set-In2 |
| Set-T8 | Set-In1 |
| Set-T9 | Set-In3 |
| Set-T10 | Set-In4 |
| Set-T11 | Set-In5 |
| Set-T12 | Set-In2 |
| Set-T13 | Set-In6 |
| Set-T14 | Set-In7 |

Figure 5:
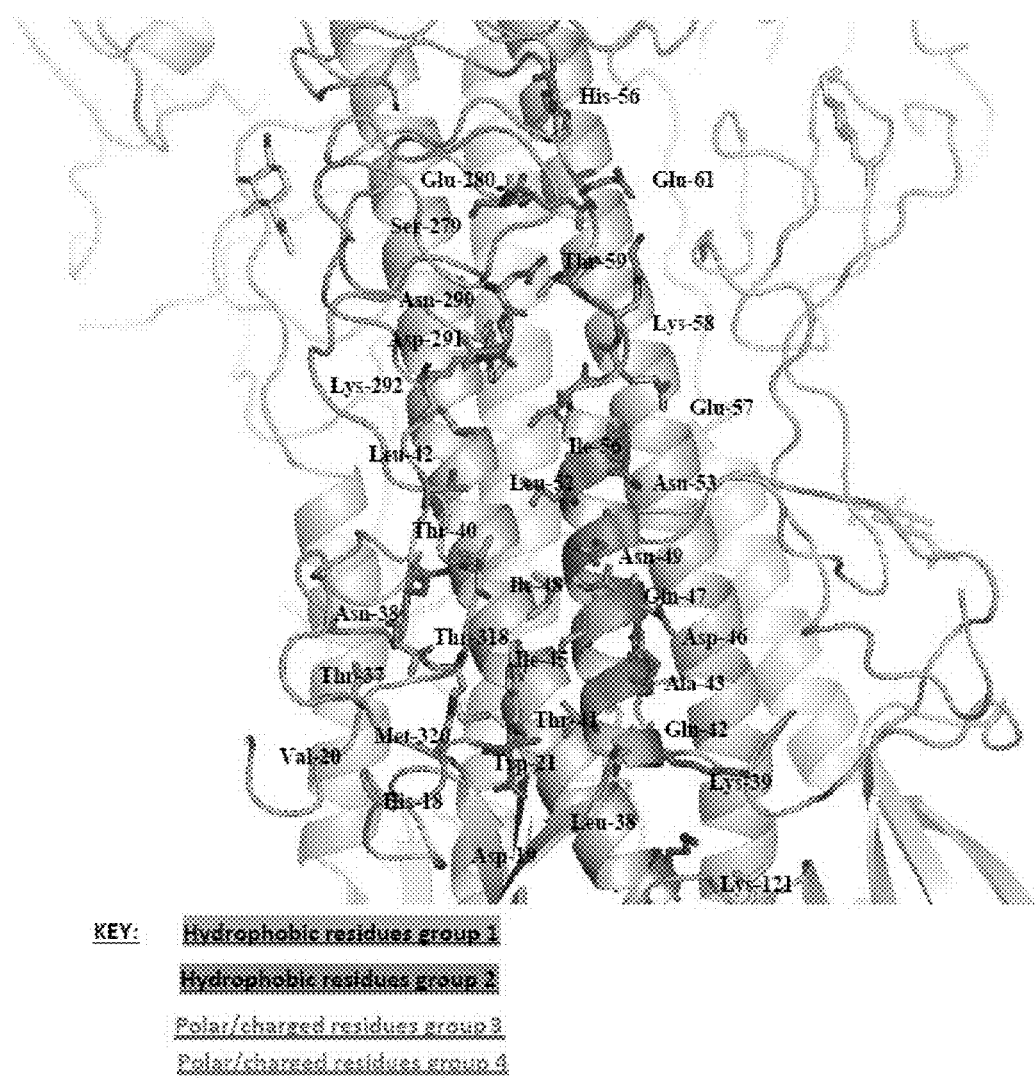
FIG. 5. Illustrates different sets of possible target residues in an HA polypeptide and specifically in and/or around the HA polypeptide MPER region. The particular HA polypeptide depicted is an H3 HA polypeptide, from Protein Data Bank ID (PDB ID) entry 1HGG.

Alternatively or additionally, infold agents are polypeptides characterized by one or more structural features set forth in Tables 4-8 and/or FIGS. 5, 13, and/or 14.

For example, in some embodiments, infold agents provided herein contain one or more of the interaction residue sequence elements defined in each box of Table 8. Each box defines one sequence element, wherein the amino acids listed in each box are interaction residues that are either adjacent to one another or separated by one or two amino acids in the infold agent polypeptide chain.

TABLE 8

Defined interaction residues for binding HA polypeptide MPER and Sialylated Glycans

| Target | Interaction Residues in Infold Agents | | | | |
|---|---|---|---|---|---|
| HA Polypeptide MPER | (I/V)& (M/C) | (F/Y)& (M/C) | (D/E) & W | (S/T)& (M/C) | (I/V/L)& N |
| | (F/Y)&N | (M/C) and N | (F/Y)& (I/V/L) | W&N | (F/Y)&W |
| | (S/T)& (I/V/L) | (D/E)& (I/V/L) | (D/E)& (M/C) | (D/E)& (F/Y) | (S/T) &W |
| | (I/V/L) & W | (S/T)& (F/Y) | (H/K/Q)& (I/V/L) | (H/K/Q)& (F/Y/P) | (H/K/Q)& (W/M) |
| N-glycosylated HA Polypeptide MPER | (Y/W/F/P) & (R/D/H/K/E/Q/N) | | | H/P/F/W/Y | |
| Sialylated Glycans (e.g., on HA receptors) | (Y/W/F) | | | H/R/Q/S | |

In some particular embodiments, provided infold agents have an amino acid sequence that is substantially homologous to that of an infold agent set forth in Table 9. In some embodiments, provided infold agents have an amino acid sequence that is substantially identical to that of an infold agent in Table 9.

An exemplary list of particular infold agents designed to bind HA MPER (e.g., broad spectrum, glycosylated and non-glycosylated) is provided in Table 9. According to the present invention, we find that fewer than 10% of the amino acids contribute towards HA binding. The present invention provides infold agents that have more than 50% pairwise sequence identity to any of the infold agent sequences listed below in Table 3. In particular, the present invention provides such infold agents whose structure additionally follows rules or parameters set forth in any one of Tables 4-8 and FIGS. 5 and 13.

TABLE 9

Amino acid sequences of infolds and their binding protein/glycan targets.

| | | BINDS TO | | |
|---|---|---|---|---|
| S.NO. | AMINO ACID SEQUENCE | HA MPER | Sialylated Glycans | MPER-proximal N-glycan |
| Infold-1 | MEHPVATLSTVERRAINLTWTKPFDGNSPLIRYILEM SENNAPWTVLLASVDPKATSVTVKGLVPARSYQFRL CAVNDVGKGQFSKDTERVSLPE (SEQ ID NO: 1) | Yes | Yes | No |
| Infold-2 | MPSVSDVPRDLEVVAATPTSLLISWDAPWTMSSRYY RITYGETGGNSPVQEFTVPGFMGGKSTATISGLKPGV DYTITVYAVYGRGDSPASSKPISINYRTEIDKPSQGGS (SEQ ID NO: 2) | Yes | No | No |
| Infold-3 | MEHPVATLSTVERRAIQLTWDAPVTTSSRRYILEMSE NNAPWTVLLTVPGFMGGKTSVTVKGLVPARSYQFR LCAVNYVGKGQFSKDTERVSLPE (SEQ ID NO: 3) | Yes | Yes | No |
| Infold-4 | MVPRDLEVVAATPTSLLISWDAPVTTSSRYYRITYGE TGGNSPVQEFTVPGFMGGKSTATIRGLKPGVDYTITV YAVYGRGDSPASSKPISINYRTEIDKPSQGGS (SEQ ID NO: 4) | Yes | No | No |
| Infold-5 | MGSLEVVAASGADSLLISWDAPFTIYSRYYRITYHVE KNGSKYGPDGLPYLQEFTVPGFMGGKSTATIRNVTE DDYTITVYAVYGRGDSPASSKPISINYRTDV (SEQ ID NO: 5) | Yes | No | No |
| Infold-6 | MSPSIDQVEPYSSTAQVQFKRPSRTVPIYHYKAEWRA VGEEVWHSKWYPFRIGGKGIVTIVGLKPETTYAVRL AAFTGSGGRSSAASEFKTQP (SEQ ID NO: 6) | Yes | No | No |
| Infold-7 | MAGSPANASTSGGDVEFTCRVFTDYPHIQWILHVEY LKVLTAAYKKRKETLYIRNVTEDAGEYTCLAGNNEG ISFHSAWLTVLP (SEQ ID NO: 7) | Yes | No | No |
| Infold-8 | MGSPLAPSSKSTSGGTAALGCLVKDPFTISFVTVSWN SGALTSGVHTPGYKKSSVVTVPSSSLGTQTYICNVNH YGKPSNTKVDKRVE (SEQ ID NO: 8) | Yes | No | No |
| Infold-9 | MVYELQVQKSVTVQEGLCVLVPCSFSSEVTFSSFYV YWFRDGGHGYYAEVVATISPMFGTPNYAPETQGRFR LLGDVQKKNCSLSIGDARMEDTGSYFFRVERGYICS GGTCRDVKYSYQQNKLNLEVTALI (SEQ ID NO: 9) | Yes | Yes | No |

TABLE 9-continued

Amino acid sequences of infolds and their binding protein/glycan targets.

| | | BINDS TO | | |
|---|---|---|---|---|
| S.NO. | AMINO ACID SEQUENCE | HA MPER | Sialylated Glycans | MPER-proximal N-glycan |
| Infold-10 | MVYELQVQKSVTVQE TABLE 9-continued Amino acid sequences of infolds and their binding protein/glycan targets.

| | | BINDS TO | | |
|---|---|---|---|---|
| S.NO. | AMINO ACID SEQUENCE | HA MPER | Sialylated Glycans | MPER-proximal N-glycan |
| | RTNQSIMIQWQPPPESHQNGILKGYIIRYNNAGNPVG YQFKNITDADVNNLLLEDLTSGTNYEIEVAAYNSAG LGVYSSKVTEWTLQ (SEQ ID NO: 22) | | | |
| Infold-23 | Chain1: EVQLVESGGGLVQPGGSLRLSCAASGFNIMD TYIHWVRQAPGKGLEWVARIFPLFGYTRYADSVKGR FTISARLWKNTAYLQMNSLRAEDTAVYYCSRWGGR KFYAMDYWGQGTLVTVSSASTKGPSVFPLAPSSKST SGGTAALGCLVKDYFPEPVTVSWNSGALTSGVHTFP AVLQSSGLYSLSSVVTVPSSSLGTQTYICNVNHKPSN TKVDKKVEP (SEQ ID NO: 23)<br>Chain2: DIQMTQSPSSLSASVGDRVTITCRASQDVNTA VAWYQQKPGKAPKLLIYSASFLYSGVPSRFSGSRSGT DFTLTISSLQPEDFATYYCQQHYTTPPTFGQGTKVEIK RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC (SEQ ID NO: 24) | Yes | No | No |
| Infold-24 | Chain 1: EVQLVESGGGLVQPGGSLRLSCASSEVTFSSFAISWV RQAPGKGLEWVAGISPMFGTPNYADSVKGRFTISAD QSTRTAYLQMNSLRAEDTAVYYCARSPSYICSGGTC VFDHWGQGTLVTVS (SEQ ID NO: 25)<br>Chain2: DIQMTQSPSSLSASVGDRVTITCRASQDVNTA VAWYQQKPGKAPKLLIYSASFLYSGVPSRFSGSRSGT DFTLTISSLQPEDFATYYCQQHYTTPPTFGQGTKVEIK RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC (SEQ ID NO: 24) | Yes | No | No |
| Infold-25 | Chain 1: EVQLVESGGGLVQPGGSLRLSCASSEMTMGGSAISW VRQAPGKGLEWVAGISPMFGTPNYADSVKGRFTISA DQSTRTAYLQMNSLRAEDTAVYYCARSPSYICSGGT CVFDHWGQGTLVTVS (SEQ ID NO: 26)<br>Chain2: DIQMTQSPSSLSASVGDRVTITCRASQDVNTA VAWYQQKPGKAPKLLIYSASFLYSGVPSRFSGSRSGT DFTLTISSLQPEDFATYYCQQHYTTPPTFGQGTKVEIK RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC (SEQ ID NO: 24) | Yes | No | No |
| Infold-26 | Chain 1: EVQLVESGGGLVQPGGSLRLSCASSEMTMGGSAISW VRQAPGKGLEWVAGISPMFGTPNYADSVKGRFTISA DGSSGTAYLQMNSLRAEDTAVYYCARSPSYICSGGT CVFDHWGQGTLVTVS (SEQ ID NO: 27)<br>Chain2: DIQMTQSPSSLSASVGDRVTITCRASQDVNTA VAWYQQKPGKAPKLLIYSASFLYSGVPSRFSGSRSGT DFTLTISSLQPEDFATYYCQQHYTTPPTFGQGTKVEIK RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC (SEQ ID NO: 24) | Yes | No | NO |
| Infold-27 | Chain 1: EVQLVESGGGLVQPGGSLRLSCASSEVTFSSFAISWV RQAPGKGLEWVAGISPMMGHPNYADSVKGRFTISA DQSTRTAYLQMNSLRAEDTAVYYCARSPSYICMQM TCVFDHWGQGTLVTVS (SEQ ID NO: 28)<br>Chain2: DIQMTQSPSSLSASVGDRVTITCRASQDVNTA VAWYQQKPGKAPKLLIYSASFLYSGVPSRFSGSRSGT DFTLTISSLQPEDFATYYCQQHYTTPPTFGQGTKVEIK RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC (SEQ ID NO: 24) | Yes | No | No |

TABLE 9-continued

Amino acid sequences of infolds and their binding protein/glycan targets.

| | | BINDS TO | | |
|---|---|---|---|---|
| S.NO. | AMINO ACID SEQUENCE | HA MPER | Sialylated Glycans | MPER-proximal N-glycan |
| Infold-28 | Chain 1:<br>EVKLVESGGG TABLE 9-continued Amino acid sequences of infolds and their binding protein/glycan targets.

| | | BINDS TO | | |
|---|---|---|---|---|
| S.NO. | AMINO ACID SEQUENCE | HA MPER | Sialylated Glycans | MPER-proximal N-glycan |
| | VAWYQQKPGKAPKLLIYSASFLYSGVPSRFSGSRSGT DFTLTISSLQPEDFATYYCQQHYTTPPTFGQGTKVEIK RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC (SEQ ID NO: 24) | | | |
| Infold-34 | Chain 1: EVKLVESGGGLVQPGGSLRLSCASSEVTFSSFALTWV RQPPGKAMEWVAGISPMMGHPNYSDSVKGRFTISAD QSTRTAYLQMNTLRAEDSAMYYCARSPSYICSGGTC VFDHWGQGTTVTVS (SEQ ID NO: 35) Chain2: DIQMTQSPSSLSASVGDRVTITCRASQDVNTA VAWYQQKPGKAPKLLIYSASFLYSGVPSRFSGSRSGT DFTLTISSLQPEDFATYYCQQHYTTPPTFGQGTKVEIK RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC (SEQ ID NO: 24) | Yes | No | No |
| Infold-35 | Chain 1: EVKLVESGGGLVQPGGSLRLSCASSEMTMGGSALT WVRQPPGKAMEWVAGISPMFGTPNYSDSVKGRFTIS ADQSTRTAYLQMNTLRAEDSAMYYCARSPSYICSGG TCVFDHWGQGTTVTVS (SEQ ID NO: 36) Chain2: DIQMTQSPSSLSASVGDRVTITCRASQDVNTA VAWYQQKPGKAPKLLIYSASFLYSGVPSRFSGSRSGT DFTLTISSLQPEDFATYYCQQHYTTPPTFGQGTKVEIK RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC (SEQ ID NO: 24) | Yes | No | No |
| Infold-36 | Chain 1: EVKLVESGGGLVQPGGSLRLSCASSEMTMGGSALT WVRQPPGKAMEWVAGISPMFGTPNYSDSVKGRFTIS ADGSSGTAYLQMNTLRAEDSAMYYCARSPSYICSGG TCVFDHWGQGTTVTVS (SEQ ID NO: 37) Chain2: DIQMTQSPSSLSASVGDRVTITCRASQDVNTA VAWYQQKPGKAPKLLIYSASFLYSGVPSRFSGSRSGT DFTLTISSLQPEDFATYYCQQHYTTPPTFGQGTKVEIK RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC (SEQ ID NO: 24) | Yes | No | No |
| Infold-37 | Chain 1: EVKLVESGGGLVQPGGSLRLSCASSEVTFSSFALTWV RQPPGKAMEWVAGISPMMGHPNYSDSVKGRFTISAD QSTRTAYLQMNTLRAEDSAMYYCARSPSYICMQMT CVFDHWGQGTTVTVS (SEQ ID NO: 38) Chain2: DIQMTQSPSSLSASVGDRVTITCRASQDVNTA VAWYQQKPGKAPKLLIYSASFLYSGVPSRFSGSRSGT DFTLTISSLQPEDFATYYCQQHYTTPPTFGQGTKVEIK RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC (SEQ ID NO: 24) | Yes | No | No |
| Infold-38 | Chain 1: EVKLVESGGGLVQPGGSLRLSCASSEMTMGGSALT WVRQPPGKAMEWVAGISPMMGHPNYSDSVKGRFTI SADQSTRTAYLQMNTLRAEDSAMYYCARSPSYICSG GTCVFDHWGQGTTVTVS (SEQ ID NO: 39) Chain2: DIQMTQSPSSLSASVGDRVTITCRASQDVNTA VAWYQQKPGKAPKLLIYSASFLYSGVPSRFSGSRSGT DFTLTISSLQPEDFATYYCQQHYTTPPTFGQGTKVEIK RTVAAPSVFIFPPSDEQLKSGTASVVCLLNNFYPREA KVQWKVDNALQSGNSQESVTEQDSKDSTYSLSSTLT LSKADYEKHKVYACEVTHQGLSSPVTKSFNRGEC (SEQ ID NO: 24) | Yes | No | No |

TABLE 9-continued

Amino acid sequences of infolds and their binding protein/glycan targets.

| | | BINDS TO | | |
|---|---|---|---|---|
| S.NO. | AMINO ACID SEQUENCE | HA MPER | Sialylated Glycans | MPER-proximal N-glycan |
| Infold-39 | Chain 1:<br>EVKLVESGGGLVQPGGSLRLSCASSEMTMGGSALT<br>WVRQPPGKAMEWVAGISPMMGHPNYSDSVKGRFTI<br>SADQSTRTAYLQMNTLRAEDSAMYYCARSPSYICM<br>QMTCVFDHWGQGTTVTVS (SEQ ID NO: 40)<br>Chain2: DIQMTQSPSSLSASVGDRVTITCRASQDVNTA<br>VAWYQQKPGKAPKLLIYSASFLYSGVPSRFSGSRSGT<br>DFTLTISSLQPEDFATYYCQQHYTTPPTFGQGTKVEIK<br>RTVAAPSVFIFPPSDEQLKSGTASVVCLLNNFYPREA<br>KVQWKVDNALQSGNSQESVTEQDSKDSTYSLSSTLT<br>LSKADYEKHKVYACEVTHQGLSSPVTKSFNRGEC<br>(SEQ ID NO: 24) | Yes | No | No |
| Infold-40 | Chain 1:<br>EVKLVESGGGLVQPGGSLRLSCASSEMTMGGSALT<br>WVRQPPGKAMEWVAGISPMMGHPNYSDSVKGRFTI<br>SADGSSGTAYLQMNTLRAEDSAMYYCARSPSYICM<br>QMTCVFDHWGQGTTVTVS (SEQ ID NO: 41)<br>Chain2: DIQMTQSPSSLSASVGDRVTITCRASQDVNTA<br>VAWYQQKPGKAPKLLIYSASFLYSGVPSRFSGSRSGT<br>DFTLTISSLQPEDFATYYCQQHYTTPPTFGQGTKVEIK<br>RTVAAPSVFIFPPSDEQLKSGTASVVCLLNNFYPREA<br>KVQWKVDNALQSGNSQESVTEQDSKDSTYSLSSTLT<br>LSKADYEKHKVYACEVTHQGLSSPVTKSFNRGEC<br>(SEQ ID NO: 24) | Yes | No | No |

In some embodiments, infold agents bind the MPER region of the HA polypeptide and are selected from the group comprising Infold-1, Infold-2, Infold-3, Infold-4, Infold-5, Infold-6, Infold-7, Infold-8, Infold-9, Infold-10, Infold-11, Infold-12, Infold-13, Infold-14, Infold-15, Infold-16, Infold-17, Infold-18, Infold-19, Infold-20, Infold-21, Infold-22, Infold-23, Infold-24, Infold-25, Infold-26, Infold-27, Infold-28, Infold-29, Infold-30, Infold-31, Infold-32, Infold-33, Infold-34, Infold-35, Infold-36, Infold-37, Infold-38, Infold-39, or Infold-40. In some embodiments, infold agents bind the MPER region of the HA polypeptide and are selected from the group comprising Infold-1, Infold-2, Infold-3, Infold-4, Infold-5, Infold-6, Infold-7, Infold-8, Infold-9, Infold-10, Infold-11, Infold-12, Infold-13, Infold-14, Infold-15, Infold-16, Infold-17, Infold-18, Infold-19, Infold-20, Infold-21, or Infold-22. In some embodiments, infold agents bind the MPER region of the HA polypeptide and are selected from the group comprising Infold-23, Infold-24, Infold-25, Infold-26, Infold-27, Infold-28, Infold-29, Infold-30, Infold-31, Infold-32, Infold-33, Infold-34, Infold-35, Infold-36, Infold-37, Infold-38, Infold-39, or Infold-40.

In some embodiments, infold agents bind the MPER region of the HA polypeptide and glycans, and are selected from the group comprising Infold-1, Infold-3, Infold-9, Infold-10, Infold-11, Infold-12, Infold-14, Infold-15, Infold-17, Infold-18, or Infold-19. In some embodiments, infold agents bind the MPER region of the HA polypeptide and glycans, and are selected from the group comprising Infold-1, Infold-3, Infold-9, Infold-10, Infold-11, Infold-12, Infold-14, Infold-15, Infold-17, Infold-18, Infold-19, or Infold-22.

In some embodiments, infold agents bind the MPER region of the HA polypeptide and the MPER-proximal N-glycans on the HA polypeptide, and are selected from the group comprising Infold-11, Infold-12, Infold-14, Infold-15, Infold-18 or Infold-19.

In some embodiments, infold agents bind the MPER region of the HA polypeptide and sialylated glycans on the HA receptor, and are selected from the group comprising Infold-1, Infold-3, Infold-9, Infold-10, Infold-17, or Infold-19. In some embodiments, infold agents bind the MPER region of the HA polypeptide and sialylated glycans on the HA receptor, and are selected from the group comprising Infold-1, Infold-3, Infold-9, Infold-10, Infold-17, Infold-19, or Infold-22.

In further embodiments, infold agents bind the MPER region of the HA polypeptide, the MPER-proximal N-glycans on the HA polypeptide and sialylated glycans on the HA receptor and is Infold-19.

In some embodiments, infold agents for use in accordance with the present invention include any of those presented in Table 9. In some embodiments, infold agents are selected from the group comprising Infold-1, Infold-3, Infold-9, Infold-10, Infold-11, Infold-12, Infold-14, Infold-15, Infold-17, Infold-18, Infold-19, Infold 22, Infold-28, and Infold-34. In some embodiments, infold agents are selected from the group comprising Infold-1, Infold-3, Infold-9, Infold-10, Infold-17, Infold-19 and Infold-28.

In some embodiments, the cognate target of infold agents in accordance with the present disclosure include at least one that corresponds to a residue found in HA at a position selected from the group consisting of: 18, 19, 20, 21, 41, 45, 49, 52, 53 and 56, and combinations thereof. In some embodiments, the cognate target residues include at least one that corresponds to a residue selected from the group consisting of Trp21, Ile45, Asp19, Asn19, Ala19, His18, Gln18, Leu18, Ile18, Val18, Gly20, Thr41, Thr49, Asn49, Gln49, Val52, Leu52, Ile52, Asn53, Ile56 and Val56.

In some embodiments, when the cognate target residues include at least one that corresponds to a residue found in HA at position 18, the infold agent is arranged and constructed such that it contains an interaction residue selected from the group consisting of His, Asp, Glu, Trp, Tyr, Asn, Lys, Arg, Gln, Met, Cys, Phe, Ile, Leu, and Val that is positioned with a 4-7 A radius of the target residue corresponding to HA position 18 when the infold agent is in the vicinity of the binding site. In some embodiments, when the cognate target residues include at least one that corresponds to a residue found in HA at position 18, the infold agent is arranged and constructed such that it contains an interaction residue selected from the group consisting of His, Asp, Glu, Trp, Tyr, Asn, Lys, Arg, Gln, Met, Cys, Phe, Ile, Leu, Val, Thr, Ser, Gly, Ala, and Pro that is positioned with a 4-7 A radius of the target residue corresponding to HA position 18 when the infold agent is in the vicinity of the binding site. In some embodiments, when the cognate target residues include at least one that corresponds to a residue found in HA at position 18, the infold agent does not contain a residue other than His, Asp, Glu, Trp, Tyr, Asn, Lys, Arg, Gln, Met, Cys, Phe, Ile, Leu, Val, Thr, Ser, Gly, Ala, or Pro when that is positioned within a 4-7 A radius when the infold agent is in the vicinity of the binding site.

In some embodiments, when the cognate target residues include at least one that corresponds to a residue found in HA at position 19, the infold agent is arranged and constructed such that it contains an interaction residue selected from the group consisting of Arg, Lys, His, Ser, Thr, Asn, Asp, Gln, Glu, Ile, Val, Ala, and Gly that is positioned with a 4-7 A radius of the target residue corresponding to HA position 19 when the infold agent is in the vicinity of the binding site. In some embodiments, when the cognate target residues include at least one that corresponds to a residue found in HA at position 19, the infold agent is arranged and constructed such that it contains an interaction residue selected from the group consisting of Arg, Lys, His, Ser, Thr, Asn, Asp, Gln, Glu, Ile, Val, Ala, Gly, Tyr, Pro, Trp, Phe, Leu, Cys, and Met that is positioned with a 4-7 A radius of the target residue corresponding to HA position 19 when the infold agent is in the vicinity of the binding site. In some embodiments, when the cognate target residues include at least one that corresponds to a residue found in HA at position 19, the infold agent does not contain a residue other than Arg, Lys, His, Ser, Thr, Asn, Asp, Gln, Glu, Ile, Val, Ala, Gly, Tyr, Pro, Trp, Phe, Leu, Cys, or Met when that is positioned within a 4-7 A radius when the infold agent is in the vicinity of the binding site.

In some embodiments, when the cognate target residues include at least one that corresponds to a residue found in HA at position 20, the infold agent is arranged and constructed such that it contains an interaction residue selected from the group consisting of Gly, Ala, Cys, Met, Ser and Pro that is positioned with a 4-7 A radius of the target residue corresponding to HA position 20 when the infold agent is in the vicinity of the binding site. In some embodiments, when the cognate target residues include at least one that corresponds to a residue found in HA at position 20, the infold agent is arranged and constructed such that it contains an interaction residue selected from the group consisting of Gly, Ala, Asn, Asp, Arg, Phe, Trp, His, Tyr, Gln, and Lys that is positioned with a 4-7 A radius of the target residue corresponding to HA position 20 when the infold agent is in the vicinity of the binding site. In some embodiments, when the cognate target residues include at least one that corresponds to a residue found in HA at position 20, the infold agent does not contain a residue other than Gly, Ala, Cys, Met, Ser, Pro, Asn, Asp, Arg, Phe, Trp, His, Tyr, Gln, or Lys when that is positioned within a 4-7 A radius when the infold agent is in the vicinity of the binding site.

In some embodiments, when the cognate target residues include at least one that corresponds to a residue found in HA at position 21, the infold agent is arranged and constructed such that it contains an interaction residue selected from the group consisting of Tyr, Ile, Met, Phe, His, Cys, and Pro that is positioned with a 4-7 A radius of the target residue corresponding to HA position 21 when the infold agent is in the vicinity of the binding site. In some embodiments, when the cognate target residues include at least one that corresponds to a residue found in HA at position 21, the infold agent is arranged and constructed such that it contains an interaction residue selected from the group consisting of Gly, Val, Arg, Ser, Thr, Trp, Leu, and Ala that is positioned with a 4-7 A radius of the target residue corresponding to HA position 21 when the infold agent is in the vicinity of the binding site. In some embodiments, when the cognate target residues include at least one that corresponds to a residue found in HA at position 21, the infold agent does not contain a residue other than Tyr, Ile, Met, Phe, His, Cys, Pro, Gly, Val, Arg, Ser, Thr, Trp, Leu, or Ala when that is positioned within a 4-7 A radius when the infold agent is in the vicinity of the binding site.

In some embodiments, when the cognate target residues include at least one that corresponds to a residue found in HA at position 41, the infold agent is arranged and constructed such that it contains an interaction residue selected from the group consisting of Ser, Thr, Asp, Asn. Glu, and Gln that is positioned with a 4-7 A radius of the target residue corresponding to HA position 41 when the infold agent is in the vicinity of the binding site. In some embodiments, when the cognate target residues include at least one that corresponds to a residue found in HA at position 41, the infold agent is arranged and constructed such that it contains an interaction residue selected from the group consisting of Met, Ile, Val, Tyr, Ala, Gly, His, Arg, Lys, and Pro that is positioned with a 4-7 A radius of the target residue corresponding to HA position 41 when the infold agent is in the vicinity of the binding site. In some embodiments, when the cognate target residues include at least one that corresponds to a residue found in HA at position 41, the infold agent does not contain a residue other than Ser, Thr, Asp, Asn. Glu, Gln, Met, Ile, Val, Tyr, Ala, Gly, His, Arg, Lys, or Pro when that is positioned within a 4-7 A radius when the infold agent is in the vicinity of the binding site.

In some embodiments, when the cognate target residues include at least one that corresponds to a residue found in HA at position 45, the infold agent is arranged and constructed such that it contains an interaction residue selected from the group consisting of Ile, Met, Phe, Leu, Val, Trp, and Cys that is positioned with a 4-7 A radius of the target residue corresponding to HA position 45 when the infold agent is in the vicinity of the binding site. In some embodiments, when the cognate target residues include at least one that corresponds to a residue found in HA at position 45, the infold agent is arranged and constructed such that it contains an interaction residue selected from the group consisting of Tyr, Pro, Ala, and Thr that is positioned with a 4-7 A radius of the target residue corresponding to HA position 45 when the infold agent is in the vicinity of the binding site. In some embodiments, when the cognate target residues include at least one that corresponds to a residue found in HA at position 45, the infold agent does not contain a residue other than Ile, Met, Phe, Leu, Val, Trp, Cys, Tyr, Pro, Ala or Thr when that is positioned within a 4-7 A radius when the infold agent is in the vicinity of the binding site.

In some embodiments, when the cognate target residues include at least one that corresponds to a residue found in HA at position 49, the infold agent is arranged and constructed such that it contains an interaction residue selected from the group consisting of Ser, Thr, Asp, Asn, Glu, Gln, Lys, and Arg that is positioned with a 4-7 A radius of the target residue corresponding to HA position 45 when the infold agent is in the vicinity of the binding site. In some embodiments, when the cognate target residues include at least one that corresponds to a residue found in HA at position 49, the infold agent is arranged and constructed such that it contains an interaction residue selected from the group consisting of Met, Ile, Val, Tyr, Ala, Gly, His, Arg, Lys, Pro, Trp, Ser and Thr that is positioned with a 4-7 A radius of the target residue corresponding to HA position 49 when the infold agent is in the vicinity of the binding site. In some embodiments, when the cognate target residues include at least one that corresponds to a residue found in HA at position 49, the infold agent does not contain a residue other than Ser, Thr, Asp, Asn, Glu, Gln, Lys, Arg, Met, Ile, Val, Tyr, Ala, Gly, His, Pro, or Trp when that is positioned within a 4-7 A radius when the infold agent is in the vicinity of the binding site.

In some embodiments, when the cognate target residues include at least one that corresponds to a residue found in HA at position 52, the infold agent is arranged and constructed such that it contains an interaction residue selected from the group consisting of Val, Leu, Ile, Phe, Met, Cys, Tyr, and Trp that is positioned with a 4-7 A radius of the target residue corresponding to HA position 52 when the infold agent is in the vicinity of the binding site. In some embodiments, when the cognate target residues include at least one that corresponds to a residue found in HA at position 52, the infold agent is arranged and constructed such that it contains an interaction residue selected from the group consisting of Cys, Met, Trp, Tyr, Ala, Gly, Thr, Pro, His, Ser, and Asp that is positioned with a 4-7 A radius of the target residue corresponding to HA position 52 when the infold agent is in the vicinity of the binding site. In some embodiments, when the cognate target residues include at least one that corresponds to a residue found in HA at position 52, the infold agent does not contain a residue other than Val, Leu, Ile, Phe, Met, Cys, Tyr, Trp, Ala, Gly, The, Pro, His or Ser when that is positioned within a 4-7 A radius when the infold agent is in the vicinity of the binding site.

In some embodiments, when the cognate target residues include at least one that corresponds to a residue found in HA at position 53, the infold agent is arranged and constructed such that it contains an interaction residue selected from the group consisting of Asn, Asp, Gln, Glu, Ser, Thr, and Lys that is positioned with a 4-7 A radius of the target residue corresponding to HA position 53 when the infold agent is in the vicinity of the binding site. In some embodiments, when the cognate target residues include at least one that corresponds to a residue found in HA at position 53, the infold agent is arranged and constructed such that it contains an interaction residue selected from the group consisting of His, Arg, Tyr, Gly, Ala, Trp, and Pro that is positioned with a 4-7 A radius of the target residue corresponding to HA position 53 when the infold agent is in the vicinity of the binding site. In some embodiments, when the cognate target residues include at least one that corresponds to a residue found in HA at position 53, the infold agent does not contain a residue other than Asn, Asp, Gln, Glu, Ser, Thr, Lys, His, Arg, Tyr, Gly, Ala, Trp or Pro when that is positioned within a 4-7 A radius when the infold agent is in the vicinity of the binding site.

In some embodiments, when the cognate target residues include at least one that corresponds to a residue found in HA at position 56, the infold agent is arranged and constructed such that it contains an interaction residue selected from the group consisting of Ile, Met, Phe, Leu, Val, Trp, and Cys that is positioned with a 4-7 A radius of the target residue corresponding to HA position 56 when the infold agent is in the vicinity of the binding site. In some embodiments, when the cognate target residues include at least one that corresponds to a residue found in HA at position 56, the infold agent is arranged and constructed such that it contains an interaction residue selected from the group consisting of Tyr, Pro, Ala, Thr, Cys, Met, Trp, and Gly that is positioned with a 4-7 A radius of the target residue corresponding to HA position 56 when the infold agent is in the vicinity of the binding site. In some embodiments, when the cognate target residues include at least one that corresponds to a residue found in HA at position 56, the infold agent does not contain a residue other than Ile, Met, Phe, Leu, Val, Trp, Cys, Tyr, Pro, Ala, Thr, Trp, or Gly when that is positioned within a 4-7 A radius when the infold agent is in the vicinity of the binding site.

As discussed further below, in some embodiments, an infold agent is a polypeptide that binds to a selected binding site. In many embodiments, an infold agent has a structure characterized by a "fold" backbone populated by interaction residues selected and arranged so that, when the infold agent is in the vicinity of the binding site, individual interaction residues are positioned within a preselected distance or volume of cognate target residues. In some embodiments, an infold agent is an engineered or designed polypeptide. In some embodiments, infold agents provided herein bind a hemagglutinin (HA) polypeptide. In some embodiments, infold agents bind to an HA polypeptide in its MPER region. In some embodiments, infold agents bind to an HA polypeptide MPER region independent of its glycosylation. For example, in some embodiments, infold agents are designed to be of appropriate size that their binding to an MPER region is not prevented by its glycosylation. In some embodiments, an infold agent binds to a glycosylated MPER region with an affinity that is at least 5%, 10%, 15%, 20%, 25%, 30%, 35%, 40%, 45%, 50%, 55%, 60%, 65%, 70%, 75%, 80%, 85%, 90% or more of its affinity for an otherwise identical non-glycosylated MPER region. In some embodiments, infold agents have volumetric sizes between 6000-1,20,000 $Å^3$. In some embodiments, provided infold agents have a volumetric size that is equal to or less than the volumetric size of an antibody. In some embodiments, an infold agent has a total target epitope surface area of approximately 20×30=600 $Å^2$. In some embodiments, the total target epitope surface area of an infold agent is less than about 10 $Å^2$, 20 $Å^2$, 30 $Å^2$, 40 $Å^2$, 50 $Å^2$, 60 $Å^2$, 70 $Å^2$, 80 $Å^2$, 85 $Å^2$, 90 $Å^2$, 95 $Å^2$, 100 $Å^2$, 105 $Å^2$, 110 $Å^2$, 115 $Å^2$, 120 $Å^2$, 125 $Å^2$, 130 $Å^2$, 135 $Å^2$, 140 $Å^2$, 145 $Å^2$, 150 $Å^2$, 151 $Å^2$, 152 $Å^2$, 153 $Å^2$, 154 $Å^2$, 155 $Å^2$, 160 $Å^2$, 165 $Å^2$, 170 $Å^2$, 175 $Å^2$, 180 $Å^2$, 185 $Å^2$, 190 $Å^2$, 195 $Å^2$, 200 $Å^2$, 210 $Å^2$, 220 $Å^2$, 230 $Å^2$, 240 $Å^2$, 250 $Å^2$, 260 $Å^2$, 270 $Å^2$, 280 $Å^2$, 290 $Å^2$, 300 $Å^2$, 310 $Å^2$, 315 $Å^2$, 320 $Å^2$, 325 $Å^2$, 330 $Å^2$ or larger. In some embodiments, total target epitope surface area is less than about 200 $Å^2$, about 175 $Å^2$, about 150 $Å^2$, about 125 $Å^2$ or smaller.

In many embodiments, infold agents have a length that is less than about 1000 amino acids. In some embodiments, infold agents have a length that is less than a maximum length of about 1000, 975, 950, 925, 900, 875, 850, 825, 800, 775, 750, 725, 700, 675, 650, 625, 600, 575, 550, 525, 500, 475, 450, 425, 400, 375, 350, 325, 300, 275, 250, 240, 230, 220, 210, 200, 190, 180, 170, 160, 150, 140, 130, 125, 120, 115, 110, 105, 100, 95, 90, 85, 80, 75, 70, 65, 60, 55, 50, 45, 40, 35, 30, 25, or 20 amino acids in length. In some embodiments, infold agents have a length that is greater than a minimum length of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or more amino acids in length. In some embodiments, infold agents have a length between any one of such minimum lengths and any one of such maximum lengths, so long as the maximum length is longer than the minimum length. In some particular embodiments, an infold agent has a length between about 20 and 500, or between 30 and 400, or between 40 and 300, or between 80 and 250 amino acids. In some embodiments, an infold agent has a length of about 84, 88, 93, 95, 98, 104, 106, 110, 111, 116, 119, 123, 124, 132, 212, 215, 244, or 245. In some embodiments, infold agents are comprised of natural amino acids. In other embodiments, infold agents are comprised of unnatural amino acids. In some embodiments, infold agents are comprised of combinations of natural and unnatural amino acids. In some embodiments, an infold agent is comprised of one, two or more polypeptide chains that are covalently (e.g., by means of a linker) or non-covalently associated. In some embodiments, an infold agent may be linked to, or part of, a longer polypeptide chain (e.g., a complete antibody, serum albumin, or other carrier protein) so long as the infold agent retains its three-dimensional structure and arrangement for interaction. In some embodiments, infold agents may be appended to the N- or C-termini of another polypeptide sequence that is or is not an infold. In some embodiments, infold agents are incorporated into the sequence of another polypeptide that is or is not an infold, thereby separating the polypeptide sequence into two or more segments. In some embodiments, appending the infold to the N or C termini or within the sequence of another polypeptide that is or is not an infold may allow for at least one or more of the following: a decrease in immunogenicity, increased circulation lifetime, slower in vivo degradation, inciting local immune response, interaction with the immune system molecules, an increase in volume, an increase in affinity for the infold target(s), an increase in specificity for the infold target(s), or the use of other commonly used therapeutic/prophylactic delivery protocols. In some embodiments, appending an infold to the N or C termini or within the sequence of another polypeptide that is or is not an infold does not have a direct effect on binding of an infold agent to a target (e.g., an HA polypeptide, the MPER region of an HA polypeptide, N-glycans on an HA polypeptide, HA receptors or sialylated glycans on HA receptors).

In some embodiments, infold agents bind to their target binding sites by interaction with one or more target residues. In some embodiments, such target residues are amino acids, saccharides, or combinations thereof. In some embodiments the present invention provides, infold agents that bind to an HA polypeptide, N-linked glycans on an HA polypeptide, an HA receptor, sialylated glycans on an HA receptor or various combinations thereof. In some embodiments, the present invention provides polypeptide agents comprising a first infold agent that binds to an HA polypeptide and a second infold agent that binds to the HA receptor. In some such embodiments, the polypeptide agent comprises a single polypeptide chain that comprises the first and second infold, optionally connected to one another by way of one or more linking amino acids. In some embodiments, an infold agent that binds to an HA receptor interacts with one or more glycans on the HA receptor. In some embodiments, infold agents bind sialylated glycans. In some embodiments, infold agents bind sialylated glycans having an umbrella-like topology. In certain embodiments, infold agents bind to umbrella-topology glycans with high affinity and/or specificity. In some embodiments, infold agents show a binding preference for umbrella-topology glycans as compared with glycans of other topologies (e.g., cone-topology glycans). In some embodiments, infold agents compete with HA for binding to HA receptors. In some embodiments, infold agents compete with HA for binding to glycans on HA receptors. In some embodiments, infold agents compete with HA for binding to umbrella-topology glycans. In some embodiments, an infold agent provided herein is an umbrella topology blocking agent. In some embodiments, an infold agent provided herein is an umbrella topology specific blocking agent. In some embodiments, an infold agent has a backbone fold structure populated by a plurality of direct binding amino acid residues (i.e., amino acid residues that make direct contacts with HA amino acids or glycans), and/or with HA receptor amino acids or glycan as described herein.

Infold Agent Activities

As discussed herein, the present invention provides infold agents that bind to HA polypeptides and/or to HA receptors. In some embodiments, provided infold agents bind to HA polypeptides independent of subtype. In some embodiments, provided infold agents that achieve universal influenza neutralization via binding to the HA polypeptide.

In some embodiments, infold agents bind to HA polypeptides of subtype H1, H2, H3, H4, H5, H6, H7, H8, H9, H10, H11, H12, H13, H14, H15, and/or H16. Specifically, in some embodiments, infold agents bind to HA polypeptides that have sequence elements characteristic of one or more of H1, H2, H3, H4, H5, H6, H7, H8, H9, H10, H11, H12, H13, H14, H15 and H16 HA polypeptides. In some embodiments, an infold agent binds to one or more of H1, H2, H3, H4, H5, H6, H7, H8, H9, H10, H11, H12, H13, H14, H15 and H16 HA polypeptides with an affinity that is at least 5%, 10%, 15%, 20%, 25%, 30%, 35%, 40%, 45%, 50%, 55%, 60%, 65%, 70%, 75%, 80%, 85%, 90% or more of its affinity for one or more of a different H1, H2, H3, H4, H5, H6, H7, H8, H9, H10, H11, H12, H13, H14, H15 and H16 HA polypeptides. In some embodiments an infold agent shows binding affinities for different HA polypeptides (e.g., HA polypeptides from different groups, clades, or clusters and/or from different strains) that are within 5 fold binding affinity of one another. In some embodiments an infold agent shows binding affinities for different HA polypeptides that are within 2 fold of one another (see for example, FIG. 7). In some embodiments an infold agent shows binding affinities for different HA polypeptides (e.g., HA polypeptides from different groups, clades, or clusters and/or from different strains) that are within 150 fold (e.g., within 100 fold, within 50 fold, within 25 fold, within 10 fold, or within 5 fold) binding affinity of one another.

In some embodiments, provided infold agents bind to at least two of H1, H3, H5, H7, and/or H9 HA polypeptides. In some embodiments, provided infold agents bind to at least three, four or five of the H1, H3, H5, H7, and/or H9 HA polypeptides.

In some embodiments, provided infold agents bind to HA polypeptides of at least one of subtypes H1, H2, H3, H4, H5, H6, H7, H8, H9, H10, H11, H12, H13, H14, H15, and/or H16, and do not bind to at least one HA polypeptide of subtypes H1, H2, H3, H4, H5, H6, H7, H8, H9, H10, H11, H12, H13, H14, H15, and/or H16. In some embodiments, infold agents bind to HA polypeptides of subtype H1. In some embodiments, infold agents bind to HA polypeptides of subtype H1 with an affinity at least 100%, at least 125%, at least 150%, at least 200% or more of that with which it binds to HA polypeptides of at least one subtype H2, H3, H4, H5, H6, H7, H8, H9, H10, H11, H12, H13, H14, H15, and/or H16. In some embodiments, infold agents bind to HA polypeptides of subtype H3. In some embodiments, infold agents bind to HA polypeptides of subtype H3 with an affinity at least 100%, at least 125%, at least 150%, at least 200% or more of that with which it binds to HA polypeptides of at least one subtype H1, H2, H4, H5, H6, H7, H8, H9, H10, H11, H12, H13, H14, H15, and/or H16.

In some embodiments, infold agents bind to a binding site that includes regions of the HA-1 and HA-2 domains in an HA polypeptide. In some embodiments, infold agents bind regions of an HA-1 domain. In some embodiments, infold agents bind regions of HA-2 domain. In some embodiments, infold agents bind both regions of the HA-1 domain and the HA-2 domain. In some embodiments, infold agents bind the MPER region of an HA polypeptide.

In some embodiments, infold agents bind a glycosylated MPER region. In some embodiments, infold agents bind a non-glycosylated MPER regions. In some embodiments, infold agents bind the MPER region of the HA polypeptide, independent of MPER glycosylation levels. In some embodiments, infold agents bind HA polypeptides independent of glycosylation levels with high affinity and/or specificity. In some embodiments, an infold agent binds to a glycosylated MPER region with an affinity that is at least 5%, 10%, 15%, 20%, 25%, 30%, 35%, 40%, 45%, 50%, 55%, 60%, 65%, 70%, 75%, 80%, 85%, 90% or more of its affinity for an otherwise identical non-glycosylated MPER region.

In some embodiments, infold agents bind the HA polypeptide. In some embodiments, infold agents bind N-linked glycans on the HA polypeptide. In some embodiments, infold agents bind the MPER-proximal N-glycans on the HA polypeptide. In some embodiments, infold agents bind N-linked glycans in the MPER proximal region of HA polypeptides with high affinity and/or specificity.

In some embodiments, infold agents bind HA receptors. In some embodiments, infold agents bind to both HA polypeptides and HA receptors. In some such embodiments, one or more provided infold agents can bind simultaneously to HA polypeptides and HA receptors. Among other things, the present invention encompasses the recognition that use of infold agents that bind to both HA polypeptides and HA receptors may permit effective inhibition of influenza infection with lower amounts of therapeutic agent (i.e., infold agent) than would be required for an agent that binds to only HA polypeptide or HA receptor but not both. Without wishing to be bound by any particular theory, we propose that ability to bind both sides of the HA polypeptide-HA receptor interaction permits increased local concentration of inhibitor (i.e., infold agent) only in those sites that are relevant; infold agent is not "wasted" on HA polypeptides or receptors that are not participating in infection.

In some embodiments, infold agents bind sialylated HA receptors. In some embodiments, infold agents bind to α2,6 sialylated glycans; in some embodiments, infold agents bind preferentially to α2,6 sialylated glycans. In certain embodiments, infold agents bind to a plurality of different α2,6 sialylated glycans. In some embodiments, infold agents are not able to bind to α2,3 sialylated glycans, and In some embodiments infold agents are able to bind to α2,3 sialylated glycans.

In some embodiments, infold agents bind to sialylated glycans having an umbrella-like topology. In some embodiments, infold agents bind to umbrella topology glycans (and/or to umbrella topology glycan mimics) more strongly than they bind to cone topology glycans. In some embodiments, infold agents show a relative affinity for umbrella glycans verses cone glycans that is about 10, 9, 8, 7, 6, 5, 4, 3, or 2.

In some embodiments, infold agents bind to umbrella topology glycans (e.g., long α2,6 sialylated glycans such as, for example, Neu5Acα2,6Galβ1-4GlcNAcβ1-3Galβ1-4GlcNAc) with high affinity. For example, in some embodiments, infold agents bind to umbrella topology glycans with an affinity comparable to that observed for a wild type HA polypeptide that mediates infection of a humans (e.g., H1N1 HA polypeptide or H3N2 HA polypeptide). In some embodiments, infold agents bind to umbrella glycans with an affinity that is at least 25%, 30%, 35%, 40%, 45%, 50%, 55%, 60%, 65%, 70%, 75%, 80%, 85%, 90%, 95%, 96%, 97%, 98%, 99%, or 100% of that observed under comparable conditions for a wild type HA polypeptide that mediates infection of humans. In some embodiments, infold agents bind to umbrella glycans with an affinity that is greater than that observed under comparable conditions for a wild type HA polypeptide that mediates infection of humans.

In some embodiments, infold agents bind to one or more of the glycans illustrated in FIG. 12. In some embodiments, infold agents bind to multiple glycans illustrated in FIG. 12. In some embodiments, infold agents bind with high affinity and/or specificity to glycans illustrated in FIG. 12. In some embodiments, infold agents bind to glycans illustrated in FIG. 12 preferentially as compared with their binding to glycans illustrated in FIG. 11. In some embodiments, infold agents bind to an oligosaccharide of the following form:

Neu5Acα2,6Sug1-Sug2-Sug3 where:
1. Neu5Ac α2,6 is always or almost always at the non-reducing end;
2. Sug1:
   a. is a hexose (frequently Gal or Glc) or hexosamine (GlcNAc or GalNAc) in α or β configuration (frequently β- for N- and O-linked extension and α- in the case of GalNAcα- that is O-linked to glycoprotein);
   b. no sugars other than Neu5Acα2,6 should be attached to any of the non-reducing positions of Sug1 (except when Sug1 is GalNAcα- that is O-linked to the glycoprotein); and/or
   c. non-sugar moieties such as sulfate, phosphate, guanidium, amine, N-acetyl, etc. can be attached to non-reducing positions (typically 6 position) of Sug1 to improve contacts with HA;
3. Sug2 and/or Sug3:
   a. hexose (frequently Gal or Glc) or hexosamine (GlcNAc or GalNAc) in α or β configuration (frequently β); and/or
   b. sugars (such as Fuc) or non-sugar moieties such as sulfate, phosphate, guanidium, amine, N-acetyl, etc. can be attached to non-reducing positions of Sug2, Sug3, and/or Sug4;
4. Linkage between any two sugars in the oligosaccharide apart from Neu5Acα2,6 linkage can be 1-2, 1-3, 1-4, and/or 1-6 (typically 1-3 or 1-4); and/or 5. Structure where Neu5Acα2,6 is linked GalNAcα that is O-linked to the glycoprotein and additional sugars are linked to the non-reducing end of GalNAcα for example
   i. Neu5Acα2,6(Neu5Acα2,3Galβ1-3)GalNAcα-
   ii. Neu5Acα2,6(Galβ1-3)GalNAcα-

In certain embodiments, infold agents bind to umbrella-topology glycans with high affinity and/or specificity. The present invention encompasses the recognition that gaining an ability to bind umbrella topology glycans (e.g., long α2,6 sialylated glycans), and particularly an ability to bind with high affinity, may confer upon an infold agent the ability to provide targeted broad spectrum neutralization against influenza virus. Without wishing to be bound by any particular theory, we propose that binding to umbrella topology glycans may be paramount, and in particular that loss of binding to other glycan types may not be required.

In some embodiments, the present invention provides infold agents that bind to umbrella topology glycans found on HA receptors of a particular target species. For example, in some embodiments, the present invention provides infold agents that bind to umbrella topology glycans found on human HA receptors, e.g., HA receptors found on human epithelial cells, and particularly infold agents that bind to umbrella topology glycans found on human HA receptors in the upper respiratory tract.

In some embodiments, infold agents bind to receptors found on human upper respiratory epithelial cells. In certain embodiments, infold agents bind to HA receptors in the bronchus and/or trachea. In some embodiments, infold agents are not able to bind receptors in the deep lung, and in some embodiments, infold agents are able to bind receptors in the deep lung.

In some embodiments, infold agents bind to at least about 10%, 15%, 20%, 25%, 30% 35%, 40%, 45%, 50%, 55%, 60%, 65%, 70%, 75%, 80%, 85%, 90% 95% or more of the glycans found on HA receptors in human upper respiratory tract tissues (e.g., epithelial cells).

In certain embodiments, binding affinity of infold agents is assessed over a range of concentrations. Such a strategy provides significantly more information, particularly in multivalent binding assays, than do single-concentration analyses. In some embodiments, for example, binding affinities of infold agents are assessed over concentrations ranging over at least 2, 3, 4, 5, 6, 7, 8, 9, 10 or more fold.

Production of Infold Agents

Infold agents, and/or characteristic portions thereof, or nucleic acids encoding them, may be produced by any available means.

Infold agents (or characteristic portions) may be produced, for example, by utilizing a host cell system engineered to express an inventive polypeptide-encoding nucleic acid. Alternatively or additionally, infold agents may be partially or fully prepared by chemical synthesis.

Where infold agents are expressed in cells (e.g., engineered cells), any expression system can be used to produce infold agents (or characteristic portions thereof). To give but a few examples, known expression systems include, for example, egg, baculovirus, plant, yeast, Madin-Darby Canine Kidney cells (MDCK), or Vero (African green monkey kidney) cells. Alternatively or additionally, infold agents (or characteristic portions) can be expressed in cells using recombinant techniques, such as through the use of an expression vector (Sambrook et al., *Molecular Cloning: A Laboratory Manual*, CSHL Press, 1989).

Alternatively or additionally, infold agents (or characteristic portions thereof), may be produced in the context of intact virus, whether otherwise wild type, attenuated, killed, etc. Infold agents, or characteristic portions thereof, may also be produced in the context of virus like particles.

Also, it will be appreciated by those of ordinary skill in the art that polypeptides, and particularly infold agents as described herein, may be generated, identified, isolated, and/or produced by culturing cells or organisms that produce infold agents (whether alone or as part of a complex, including as part of a virus particle or virus), under conditions that allow ready screening and/or selection of polypeptides capable of binding to umbrella-topology glycans. To give but one example, in some embodiments, it may be useful to produce and/or study a collection of infold agents under conditions that reveal and/or favor those variants that bind to HA polypeptides or umbrella topology glycans (e.g., with particular specificity and/or affinity). In some embodiments, such a collection of infold agents results from evolution in nature. In some embodiments, such a collection of infold agents results from engineering. In some embodiments, such a collection of infold agents results from a combination of engineering and natural evolution.

Nucleic Acids

In certain embodiments, the present invention provides nucleic acids which encode an infold agent or a characteristic or biologically active portion of an infold agent. In some embodiments, the invention provides nucleic acids which are complementary to nucleic acids which encode an infold agent or a characteristic or biologically active portion of an infold agent.

In some embodiments, the invention provides nucleic acid molecules which hybridize to nucleic acids encoding an infold agent or a characteristic or biologically active portion of an infold agent. Such nucleic acids can be used, for example, as primers or as probes. To give but a few examples, such nucleic acids can be used as primers in polymerase chain reaction (PCR), as probes for hybridization (including in situ hybridization), and/or as primers for reverse transcription-PCR (RT-PCR).

In certain embodiments, nucleic acids can be DNA or RNA, and can be single stranded or double-stranded. In some embodiments, nucleic acids may include one or more non-natural nucleotides; In some embodiments, nucleic acids include only natural nucleotides.

Antibodies to Infold Agents

The present invention provides antibodies to infold agents. These may be monoclonal or polyclonal and may be prepared by any of a variety of techniques known to those of ordinary skill in the art (e.g., see Harlow and Lane, Antibodies: A Laboratory Manual, Cold Spring Harbor Laboratory, 1988). For example, antibodies can be produced by cell culture techniques, including the generation of monoclonal antibodies, or via transfection of antibody genes into suitable bacterial or mammalian cell hosts, in order to allow for the production of recombinant antibodies.

Systems for Identifying and/or Characterizing Infold Agents

The present invention provides a variety of systems for testing, characterizing, and/or identifying infold agents.

In some embodiments, infold agents are characterized by such systems and methods that involve contacting the infold agent with one or more candidate substrates, such as regions of HA polypeptides, the MPER region of HA-polypeptides, N-glycans on HA polypeptides, HA receptors, sialylated HA receptors, glycans on sialylated HA receptors and/or umbrella topology glycans on sialylated HA receptors.

In some embodiments, an infold agent and/or candidate substrate may be free in solution, fixed to a support, and/or expressed in and/or on the surface of a cell. The candidate substrate and/or infold agent may be labeled, thereby permitting detection of binding. Either the infold agent or the candidate substrate is the labeled species. Competitive binding formats may be performed in which one of the substances is labeled, and one may measure the amount of free label versus bound label to determine the effect on binding.

In some embodiments, binding assays involve, for example, exposing a candidate substrate to an infold agent and detecting binding between the candidate substrate and the infold agent. A binding assay may be conducted in vitro (e.g., in a candidate tube, comprising substantially only the components mentioned; in cell-free extracts; and/or in substantially purified components). Alternatively or additionally, binding assays may be conducted in cyto and/or in vivo (e.g., within a cell, tissue, organ, and/or organism; described in further detail below).

In certain embodiments, at least one infold agent is contacted with at least one candidate substrate and an effect detected. In some embodiments, for example, an infold agent is contacted with a candidate substrate, and binding between the two entities is monitored. In some embodiments, an assay may involve contacting a candidate substrate with a characteristic portion of an infold agent. Binding of the infold agent to the candidate substrate is detected. It will be appreciated that fragments, portions, homologs, variants, and/or derivatives of infold agents may be employed, provided that they comprise the ability to bind one or more candidate substrates.

Binding of a infold agent to the candidate substrate may be determined by a variety of methods well-known in the art. The present invention provides assays involving solid phase-bound infold agents and detecting their interactions with one or more candidate substrates. Thus, an infold agent may comprise a detectable marker, such as a radioactive, fluorescent, and/or luminescent label. Furthermore, candidate substrate can be coupled to substances which permit indirect detection (e.g. by means of employing an enzyme which uses a chromogenic substrate and/or by means of binding a detectable antibody). Changes in the conformation of infold agents as the result of an interaction with a candidate substrate may be detected, for example, by the change in the emission of the detectable marker. Alternatively or additionally, solid phase-bound protein complexes may be analyzed by means of mass spectrometry.

In some embodiments, the infold agent can be non-immobilized. In some embodiments, the non-immobilized component may be labeled (with for example, a radioactive label, an epitope tag, an enzyme-antibody conjugate, etc.). Alternatively or additionally, binding may be determined by immunological detection techniques. For example, the reaction mixture may be subjected to Western blotting and the blot probed with an antibody that detects the non-immobilized component. Alternatively or additionally, enzyme linked immunosorbent assay (ELISA) may be utilized to assay for binding.

In certain embodiments, cells may be directly assayed for binding between infold agents and candidate substrates. Immunohistochemical techniques, confocal techniques, and/or other techniques to assess binding are well known to those of skill in the art. Various cell lines may be utilized for such screening assays, including cells specifically engineered for this purpose. Examples of cells used in the screening assays include mammalian cells, fungal cells, bacterial cells, or viral cells. A cell may be a stimulated cell, such as a cell stimulated with a growth factor. One of skill in the art would understand that the invention disclosed herein contemplates a wide variety of in cyto assays for measuring the ability of infold agents to bind to candidate substrates.

Depending on the assay, cell and/or tissue culture may be required. A cell may be examined using any of a number of different physiologic assays. Alternatively or additionally, molecular analysis may be performed, including, but not limited to, western blotting to monitor protein expression and/or test for protein-protein interactions; mass spectrometry to monitor other chemical modifications; etc.

The present invention provides methods for identifying infold agents that bind to candidate substrates and, therefore, may be involved in influenza infection. One in cyto method of identifying substances that bind to candidate substrates is the two-hybrid system assay (Fields et al., 1994, *Trends in Genetics*, 10:286; and Colas et al., 1998, *TIBTECH*, 16:355; both of which are incorporated herein by reference). In this assay, yeast cells express a first fusion protein comprising a test substance in accordance with the present invention (e.g. an infold agent, gene encoding an infold agent, and/or characteristic portions thereof) and a DNA-binding domain of a transcription factor such as Gal4 and/or LexA. The cells additionally contain a reporter gene whose promoter contains binding sites for the corresponding DNA-binding domain. By transforming the cells with a vector that expresses a second fusion protein comprising a candidate substrate fused to an activation domain (e.g. from Gal4 and/or herpes simplex virus VP16) expression of the reporter gene may be increased if the candidate substrate interacts with the infold agent. In this way, it is possible rapidly to identify novel infold agents.

In some embodiments, any of the binding assays described herein may be performed using a range of concentrations of infold agents and/or candidate substrates. In some embodiments, the binding assays described herein are used to assess the ability of a candidate substrate to bind to a infold agent over range of infold agent concentrations (e.g. greater than about 100 µg/ml, about 100 µg/ml, about 50 µg/ml, about 40 µg/ml, about 30 µg/ml, about 20 µg/ml, about 10 µg/ml, about 5 µg/ml, about 4 µg/ml, about 3 µg/ml, about 2 µg/ml, about 1.75 µg/ml, about 1.5 µg/ml, about 1.25 µg/ml, about 1.0 µg/ml, about 0.9 µg/ml, about 0.8 µg/ml, about 0.7 µg/ml, about 0.6 µg/ml, about 0.5 µg/ml, about 0.4 µg/ml, about 0.3 µg/ml, about 0.2 µg/ml, about 0.1 µg/ml, about 0.05 µg/ml, about 0.01 µg/ml, and/or less than about 0.01 µg/ml).

In some embodiments, any of the binding studies described herein can be executed in a high throughput fashion. Using high throughput assays, it is possible to screen up to several thousand infold agents in a single day. In some embodiments, each well of a microtiter plate can be used to run a separate assay against a selected candidate substrate, or, if concentration and/or incubation time effects are to be observed, every 5-10 wells can test a single candidate substrate. Thus, a single standard microtiter plate can assay up to 96 binding interactions between infold agents and candidate substrates; if 1536 well plates are used, then a single plate can assay up to 1536 binding interactions between infold agents and candidate substrates; and so forth. It is possible to assay many plates per day. For example, up to about 6,000, about 20,000, about 50,000, or more than about 100,000 assay screens can be performed on binding interactions between infold agents and candidate substrates using high throughput systems in accordance with the present invention.

In some embodiments, such methods utilize an animal host. As used herein, an "animal host" includes any animal model suitable for influenza research. For example, animal hosts suitable for the invention can be any mammalian hosts, including primates, ferrets, cats, dogs, cows, horses, rodents such as, mice, hamsters, rabbits, and rats. In certain embodiments, an animal host used for the invention is a ferret. In particular, in some embodiments, an animal host is naïve to viral exposure or infection prior to administration of an infold agent (optionally in an inventive composition). In some embodiments, the animal host is inoculated with, infected with, or otherwise exposed to virus prior to or concurrent with administration of an infold agent. An animal host used in the practice of the present invention can be inoculated with, infected with, or otherwise exposed to virus by any method known in the art. In some embodiments, an animal host may be inoculated with, infected with, or exposed to virus intranasally.

In some embodiments, a suitable animal host may have a similar distribution of umbrella vs. cone topology glycans and/or α2,6 glycans vs. α 2,3 glycans to the distribution found in the human respiratory tract. For example, it is contemplated that a ferret as an animal host may be more representative than a mouse when used as model of disease caused by influenza viruses in humans (Tumpey, et al. *Science* (2007) 315; 655-659). Without wishing to be bound any theories, the present invention encompasses the idea that ferrets may have a more similar distribution of glycans in the respiratory tract to those in the human respiratory tract than mouse does to human.

Naïve and/or inoculated animals may be used for any of a variety of studies. For example, such animal models may be used for virus transmission studies as in known in the art. It is contemplated that the use of ferrets in virus transmission studies may serve as a reliable predictor for virus transmission in humans. For example, air transmission of viral influenza from inoculated animals (e.g., ferrets) to naïve animals is known in the art (Tumpey, et al. *Science* (2007) 315; 655-659). Virus transmission studies may be used to test infold agents. For example, infold agents may be administered to a suitable animal host before, during or after virus transmission studies in order to determine the efficacy of said infold agent in blocking virus binding and/or infectivity in the animal host. Using information gathered from virus transmission studies in an animal host, one may predict the efficacy of an infold agent in blocking virus binding and/or infectivity in a human host.

Pharmaceutical Compositions and Methods of Treatment

In some embodiments, the present invention provides for pharmaceutical compositions including infold agents and/or related entities. For example, in some embodiments, infold agent polypeptides, nucleic acids encoding such polypeptides, characteristic or biologically active fragments of such polypeptides or nucleic acids, antibodies that bind to and/or compete with such polypeptides or fragments, small molecules that interact with or compete with such polypeptides or with glycans that bind to them, etc. are included in pharmaceutical compositions.

The invention encompasses treatment of influenza infection by administration of such pharmaceutical compositions. In some embodiments, pharmaceutical compositions are administered to a subject suffering from or susceptible to an influenza infection. In some embodiments, a subject is considered to be suffering from an influenza infection in the subject is displaying one or more symptoms commonly associated with influenza infection. In some embodiments, the subject is known or believed to have been exposed to the influenza virus. In some embodiments, a subject is considered to be susceptible to an influenza infection if the subject is known or believed to have been exposed to the influenza virus. In some embodiments, a subject is known or believed to have been exposed to the influenza virus if the subject has been in contact with other individuals known or suspected to have been infected with the influenza virus and/or if the subject is or has been present in a location in which influenza infection is known or thought to be prevalent.

In some embodiments, subjects suffering from or susceptible to influenza infection are tested for antibodies to infold agents prior to, during, or after administration of pharmaceutical compositions. In some embodiments, subjects having such antibodies are not administered pharmaceutical compositions comprising infold agents. In some embodiments, an appropriate dose of pharmaceutical composition and/or infold agent is selected based on detection (or lack thereof) of such antibodies.

In some embodiments, selection of a particular subject for treatment, particular infold agent or composition for administration, and/or particular dose or regimen for administration, is memorialized, for example in a written, printed, or electronic storage form.

Inventive compositions may be administered prior to or after development of one or more symptoms of influenza infection.

The invention encompasses treatment of influenza infections by administration of agents described herein.

The present invention also provides other therapeutic compositions useful in the treatment of viral infections. In some embodiments, treatment is accomplished by administration of an agent that interferes with expression or activity of an HA polypeptide.

In some embodiments, the present invention provides pharmaceutical compositions comprising antibodies or other agents related to provided infold agents. For example, the invention provides compositions containing antibodies that recognize infold agents, nucleic acids (such as nucleic acid sequences complementary to sequences of infold agents, which can be used for RNAi), or combination thereof. In some embodiments, collections of different agents, having diverse structures are utilized. In some embodiments, therapeutic compositions comprise one or more multivalent agents. In some embodiments, treatment comprises urgent administration shortly after exposure or suspicion of exposure to influenza virus.

In general, a pharmaceutical composition will include a therapeutic agent in addition to one or more inactive agents such as a sterile, biocompatible carrier including, but not limited to, sterile water, saline, buffered saline, or dextrose solution. Alternatively or additionally, the composition can contain any of a variety of additives, such as stabilizers, buffers, excipients (e.g., sugars, amino acids, etc), or preservatives.

In certain embodiments, the therapeutic agent present in an inventive pharmaceutical composition will consist of one or more infold agents as described herein. In some embodiments, an inventive pharmaceutical composition contains an infold agent that binds to HA polypeptides or umbrella topology glycans (and/or to umbrella topology glycan mimics). In some such embodiments, the inventive composition is substantially free of related agents (e.g., of other infold agents, etc.) that do not bind to umbrella-topology glycans. In some such embodiments, the pharmaceutical compositions contains not more than least 5%, 10%, 15%, 20%, 25%, 30%, 35%, 40%, 45%, 50%, 55%, 60%, 65%, 70%, 75%, 80%, 85%, 90% or more of an agent that binds to a glycosylated or non-glycosylated HA polypeptide and/or HA receptor glycans other than umbrella topology glycans.

In certain embodiments, a pharmaceutical composition will include a therapeutic agent that is encapsulated, trapped, or bound within a lipid vesicle, a bioavailable and/or biocompatible and/or biodegradable matrix, or other microparticle.

In some embodiments, a provided pharmaceutical composition will include an infold agent that is not aggregated. For example, in some embodiments, less than 1%, 2%, 5%, 10%, 20%, or 30%, by dry weight or number, of infold agents is present in an aggregate.

In some embodiments, a provided pharmaceutical composition will include an infold agent that is not denatured. For example, in some embodiments, less than 1%, 2%, 5%, 10%, 20%, or 30%, by dry weight or number, of infold agents administered is denatured.

In some embodiments, a provided pharmaceutical composition will include an infold agent that is not inactive. For example, in some embodiments, less than 1%, 2%, 5%, 10%, 20%, or 30%, by dry weight or number, of infold agents administered is inactive.

In some embodiments, pharmaceutical compositions are formulated to reduce immunogenicity of provided infold agents. For example, in some embodiments, a provided infold agent is associated with (e.g., bound to) an agent, such as polyethylene glycol and/or carboxymethyl cellulose, that masks its immunogenicity. In some embodiments, a provided binding agent has additional glycosylation that reduces immunogenicity.

Combination Therapy

Pharmaceutical compositions of the present invention may be administered either alone or in combination with one or more other therapeutic agents including, but not limited to, vaccines and/or antibodies. By "in combination with," it is not intended to imply that the agents must be administered at the same time or formulated for delivery together, although these methods of delivery are within the scope of the invention. In general, each agent will be administered at a dose and on a time schedule determined for that agent. Additionally, the invention encompasses the delivery of the pharmaceutical compositions in combination with agents that may improve their bioavailability, reduce or modify their metabolism, inhibit their excretion, or modify their distribution within the body. Although the pharmaceutical compositions of the present invention can be used for treatment of any subject (e.g., any animal) in need thereof, they are most preferably used in the treatment of humans.

In some embodiments, pharmaceutical compositions of the present invention and/or one or more infold agents are administered in combination with one or more anti-viral agents. In some embodiments, such anti-viral agents include, but are not limited to, acyclovir, ribavirin, amantadine, remantidine, zanamivir (RELENZA®), oseltamivir (TAMIFLU®), amantadine, rimantadine and/or combinations thereof.

In some embodiments, pharmaceutical compositions of the present invention and/or one or more infold agents are administered in combination with one or more antibodies. In some embodiments, the antibodies bind HA polypeptides on the virus. In some embodiments, the antibodies bind the MPER region of the HA polypeptide (e.g., H1, H2, H3, H4, H5, H6, H7, H8, H9, H10, H11, H12, H13, H14, H15, or H16 polypeptides). In some embodiments, the antibodies bind a glycosylated MPER region of the HA polypeptide. In some embodiments, the antibodies bind the HA receptor. In some embodiments, the antibodies bind to sialyated glycans on the HA receptor. In some embodiments, the antibodies are C179, F10 and CR6261.

In some embodiments, pharmaceutical compositions of the present invention and/or one or more infold agents are administered in combination with one or more anti-viral agents. In some embodiments, such anti-viral agents include, but are not limited to, acyclovir, ribavirin, amantadine, remantidine, zanamivir (Relenza), oseltamivir (Tamiflu), amantadine, rimantadine and/or combinations thereof.

In some embodiments, pharmaceutical compositions of the present invention and/or one or more infold agents are administered in combination one or more vaccines. In some embodiments, the vaccine is a anti-viral vaccine. In some embodiments, the vaccine is an anti-influenza vaccine. In some embodiments, the anti-influenza vaccine is to treat seasonal influenza (e.g., commonly referred to as the flu). In some embodiments, the anti-influenza vaccine is the flu shot and/or FluMist. In some embodiments, the anti-influenza vaccine is targeted to a specific combination of one or more HA polypeptides (e.g., H1, H2, H3, H4, H5, H6, H7, H8, H9, H10, H11, H12, H13, H14, H15, or H16 polypeptides). In some embodiments, the anti-influenza vaccine is specific for one or more combinations of H1N1, H2N2, H3N2, H5N1, H7N7, H1N2, H9N2, H7N2, H7N3, or H10N7 viruses. In some embodiments, the anti-influenza vaccine is specific to H1N1 viruses. In some embodiments, the anti-influenza vaccine is specific to H3N2 viruses. In some embodiments, the anti-influenza vaccine is specific to H1N1 and H3N2 viruses.

In some embodiments pharmaceutical compositions and/or one or more infold agents may be administered in combination with one or more other pharmaceutical agents used to treat the symptoms associated with influenza virus infection. In some embodiments, pharmaceutical agents used to treat the symptoms associated with influenza infection are pain relievers, anti-inflammatories, antibiotics and/or combinations thereof. In some embodiments, pharmaceutical agents used to treat the symptoms associated with influenza infection are acetaminophen, ibuprofen, aspirin, naproxen and/or combinations thereof.

Methods of Administration

Pharmaceutical compositions of the present invention can be administered by a variety of routes, including oral, intravenous, intramuscular, intra-arterial, subcutaneous, intraventricular, transdermal, interdermal, rectal, intravaginal, intraperitoneal, topical (as by powders, ointments, creams, or drops), mucosal, nasal, buccal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the agent (e.g., its stability in the environment of the gastrointestinal tract), the condition of the patient (e.g., whether the patient is able to tolerate oral administration), etc.

At present the oral or nasal spray or aerosol route (e.g., by inhalation) is most commonly used to deliver therapeutic agents directly to the lungs and respiratory system. However, the invention encompasses the delivery of the inventive pharmaceutical composition by any appropriate route taking into consideration likely advances in the sciences of drug delivery.

In some embodiments, preparations for inhaled or aerosol delivery comprise a plurality of particles. In some embodiments, such preparations have a mean particle size of 4, 5, 6, 7, 8, 9, 10, 11, 12, or 13 microns. In some embodiments, preparations for inhaled or aerosol delivery are formulated as a dry powder. In some embodiments, preparations for inhaled or aerosol delivery are formulated as a wet powder, for example through inclusion of a wetting agent. in some embodiments, the wetting agent is selected from the group consisting of water, saline, or other liquid of physiological pH.

In some embodiments, inventive compositions are administered as drops to the nasal or buccal cavity. In some embodiments, a dose may comprise a plurality of drops (e.g., 1-100, 1-50, 1-20, 1-10, 1-5, etc.)

In some embodiments, inventive compositions are administered using a device that delivers a metered dosage of composition (e.g., of infold agent).

Suitable devices for use in delivering intradermal pharmaceutical compositions described herein include short needle devices such as those described in U.S. Pat. No. 4,886,499, U.S. Pat. No. 5,190,521, U.S. Pat. No. 5,328,483, U.S. Pat. No. 5,527,288, U.S. Pat. No. 4,270,537, U.S. Pat. No. 5,015,235, U.S. Pat. No. 5,141,496, U.S. Pat. No. 5,417,662. Intradermal compositions may also be administered by devices which limit the effective penetration length of a needle into the skin, such as those described in WO99/34850, incorporated herein by reference, and functional equivalents thereof. Also suitable are jet injection devices which deliver liquid compositions to the dermis via a liquid jet injector or via a needle which pierces the stratum corneum and produces a jet which reaches the dermis. Jet injection devices are described for example in U.S. Pat. No. 5,480,381, U.S. Pat. No. 5,599,302, U.S. Pat. No. 5,334,144, U.S. Pat. No. 5,993,412, U.S. Pat. No. 5,649,912, U.S. Pat. No. 5,569,189, U.S. Pat. No. 5,704,911, U.S. Pat. No. 5,383,851, U.S. Pat. No. 5,893,397, U.S. Pat. No. 5,466,220, U.S. Pat. No. 5,339,163, U.S. Pat. No. 5,312,335, U.S. Pat. No. 5,503,627, U.S. Pat. No. 5,064,413, U.S. Pat. No. 5,520,639, U.S. Pat. No. 4,596,556, U.S. Pat. No. 4,790,824, U.S. Pat. No. 4,941,880, U.S. Pat. No. 4,940,460, WO 97/37705 and WO 97/13537. Also suitable are ballistic powder/particle delivery devices which use compressed gas to accelerate compositions in powder form through the outer layers of the skin to the dermis. Additionally, conventional syringes may be used in the classical mantoux method of intradermal administration.

Formulations

General considerations in the formulation and manufacture of pharmaceutical agents may be found, for example, in *Remington's Pharmaceutical Sciences*, 19$^{th}$ ed., Mack Publishing Co., Easton, Pa., 1995.

Pharmaceutical compositions may be administered in any dose appropriate to achieve a desired outcome. In some embodiments, the desired outcome is reduction in intensity, severity, and/or frequency, and/or delay of onset of one or more symptoms of influenza infection.

In some embodiments, pharmaceutical compositions are formulated to administer a dose of infold agent effective to compete with an influenza HA polypeptide for binding to umbrella topology glycans. In some embodiments, such binding by an influenza HA polypeptide is reduced after administration of one or more doses of an infold agent composition as compared with its level absent such administration. In some embodiments, pharmaceutical compositions are formulated to administer a dose of infold agent effective to saturate at least 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or more HA polypeptide binding sites (e.g., HA polypeptide binding sites containing umbrella topology glycans) present in the subject (e.g., in the respiratory tract of the subject) receiving the composition.

In some embodiments, pharmaceutical compositions are formulated to deliver a unit dose of infold agent within the range of 0.0001 to 1000 nmg/kg.

In some embodiments, pharmaceutical compositions are administered in multiple doses. In some embodiments, pharmaceutical compositions are administered in multiple doses/day. In some embodiments, pharmaceutical compositions are administered according to a continuous dosing regimen, such that the subject does not undergo periods of less than therapeutic dosing interposed between periods of therapeutic dosing. In some embodiments, pharmaceutical compositions are administered according to an intermittent dosing regimen, such that the subject undergoes at least one period of less than therapeutic dosing interposed between two periods of therapeutic dosing.

Diagnostics/Kits

In some embodiments, the present invention provides kits for detecting infold agents as described herein whether or not such polypeptides are infold agents.

In some embodiments, the present invention provides kits for detecting infold agents and particular for detecting infold agents with particular HA polypeptide and/or glycan binding characteristics (e.g., binding to umbrella glycans, to $\alpha 2,6$ sialylated glycans, to long $\alpha 2,6$ sialylated glycans, etc.) in pathological samples, including, but not limited to, blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver. The present invention also provides kits for detecting infold agents of interest in environmental samples, including, but not limited to, soil, water, and flora. Other samples that have not been listed may also be applicable.

In some embodiments, methods for detecting infold agents involve providing a pathological and/or environmental sample, contacting the sample with an infold agent, and determining whether the infold agent binds to the sample relative to a negative control binding agent. In some embodiments, such methods involve a step of processing the sample (e.g., subjecting the sample to one or more purification steps) prior to the step of contacting. In some embodiments, provided infold agents are labeled with a detectable moiety (e.g., fluorescent, radioactive, chemoluminescent label, etc.). In some embodiments, infold agents are detectable via immunological methods (e.g., western blotting, ELISA, immunofluorescence, etc.). In some embodiments, infold agents are immobilized (e.g., to a bead, to a microtiter dish, to an array, to a glycan array, etc.) prior to the step of contacting.

In certain embodiments, inventive kits may include one or more agents that specifically detect infold agents with HA polypeptide and/or particular glycan binding characteristics. Such detecting agents may include, for example, antibodies that specifically recognize certain infold agents (e.g., infold agents that bind to umbrella glycans and/or to $\alpha 2,6$ sialylated glycans and/or to long $\alpha 2,6$ sialylated glycans), which can be used to specifically detect such infold agents by ELISA, immunofluorescence, and/or immunoblotting.

Antibodies that bind to infold agents can also be used in virus neutralization tests, in which a sample is treated with antibody specific to infold agent of interest, and tested for its ability to infect cultured cells relative to untreated sample. If the virus in that sample contains such infold agents, the antibody will neutralize the virus and prevent it from infecting the cultured cells. Alternatively or additionally, such antibodies can also be used in HA-inhibition tests, in which the HA protein is isolated from a given sample, treated with antibody specific to a particular infold agents or set of infold agents, and tested for its ability to agglutinate erythrocytes relative to untreated sample. If the virus in the sample contains such an infold agent, the antibody will neutralize the activity of infold agents and prevent it from agglutinating erythrocytes (Harlow & Lane, Antibodies: A Laboratory Manual, CSHL Press, 1988; who.int/csr/resources/publications/influenza/WHO_CDS_CSR_NCS_2002_5/en/index; who.int/csr/disease/avian_influenza/guidelines/labtests/en/index). In some embodiments, such agents may include nucleic acids that specifically bind to nucleotides that encode particular infold agents and that can be used to specifically detect such infold agents by RT-PCR or in situ hybridization (who.int/csr/resources/publications/influenza/WHO_CDS_CSR_NCS_2002_5/en/index; who.int/csr/disease/avian_influenza/guidelines/labtests/en/index). In certain embodiments, nucleic acids which have been isolated from a sample are amplified prior to detection. In certain embodiments, diagnostic reagents can be detectably labeled.

The present invention also provides kits containing reagents according to the invention for the treatment of influenza virus infection. Contents of the kits include, but are not limited to, expression plasmids containing infold agent nucleotides (or characteristic or biologically active portions) encoding infold agents of interest (or characteristic or biologically active portions). Alternatively or additionally, kits may contain expression plasmids that express infold agents of interest (or characteristic or biologically active portions). Expression plasmids containing no virus genes may also be included so that users are capable of incorporating infold agent nucleotides from any influenza virus of interest. Mammalian cell lines may also be included with the kits, including but not limited to, Vero and MDCK cell lines. In certain embodiments, diagnostic reagents can be detectably labeled.

In certain embodiments, kits for use in accordance with the present invention may include, a reference sample, instructions for processing samples, performing the test, instructions for interpreting the results, buffers and/or other reagents necessary for performing the test. In certain embodiments the kit can comprise a panel of antibodies.

The present invention provides kits for administration of pharmaceutical compositions. For example, in some embodiments, the invention provides a kit comprising at least one dose of an infold agent. In some embodiments, the invention provides a kit comprising an initial unit dose and one or more subsequent unit doses of an infold agent. In some such embodiments, the initial unit dose is greater than the subsequent unit doses or wherein the all of the doses are equal.

In some embodiments, inventive kits (particularly those for administration of infold agent pharmaceutical compositions) comprise at least one component of a delivery device, e.g., an inhaler. In some such embodiments, the invention provides a kit comprising at least one component of a delivery device, e.g., an inhaler and a dose of an of an infold agent.

In some embodiments, provided kits comprise instructions for use.

EXEMPLIFICATION

Example 1

Design of Infold Agents

The present example illustrates the design of infold agents to bind to specific regions on an HA polypeptide.

One exemplary infold sequence was designed against the HA binding interface (FIG. 6). These interactions revealed several potentially stabilizing contacts with both the head (HA-1) and stalk (HA-2) domains of HA (Table 10). It is seen that one of the regions of the designed protein has the desired stabilizing hydrophobic contacts and hydrogen bonds with both HA-1 and HA-2 domains, while another prominent region has stabilizing hydrophobic interactions primarily with HA-1, while yet another region has stabilizing hydrophobic interactions primarily with HA-2. Thus, the designed infold protein under consideration is expected to bind at the stalk-head interface of the HA-1 and HA-2 domains. Furthermore, as expected, the designed proteins are seen to accommodate the N-glycosylation in the HA MPER region owing to their significantly smaller volume than antibodies (FIG. 6). Thus, supporting that the designed proteins will bind with good affinity to both MPER-glycosylated and MPER-non-glycosylated influenza strains, supporting universal influenza neutralization.

TABLE 10

Structural characterization of
Infold-2 designed protein-HA binding interface

| Stalk-protein<br>(HA-2-Infold) Interface | Head-protein<br>(HA-1-Infold) Interface |
|---|---|
| Number of interface residues (15:11) | Number of interface residues (10:9) |
| Number of interface atoms (47:43) | Number of interface atoms (34:27) |
| Solvent accessible interface area ($411.0$ $A^2$:$435.3$ $A^2$) | Solvent accessible interface area ($241.7$ $A^2$:$239.3$ $A^2$) |
| Number of Hydrogen bonds: 4<br>Gln42_OE1 - Gly78_N<br>Gln42_OE1 - Gly76_N<br>Asp19_O - Tyr75_OH<br>Thr49_OG1 - Arg26_NH2 | Number of Hydrogen bonds: 3<br>Gln34_NE2 - Thr22_O<br>Ser292_O - Thr22_OG1<br>Gln34_OE1 - Thr23_OG1 |
| Important interface residues:<br>Stalk: Val18, Asp19, Gly20, Trp21, Lys38, Thr41, Gln42, Ile45, Asp46, Val48, Thr49, Asn50, Val52, Asn53, Ile56<br>Infold: Val21, Thr23, Ser25, Arg26, Phe49, Val74, Tyr75, Gly76, Arg77, Gly78, Asp79 | Important interface residues:<br>Head: His12, Asn13, Ser16, Glu18, Thr31, His32, Gln34, Ser292, Met293, Thr319<br>Infold: Glu18, Val21, Thr22, Thr23, Ser24, Ser25, Arg26, Phe49, Met50 |

Figure 1:
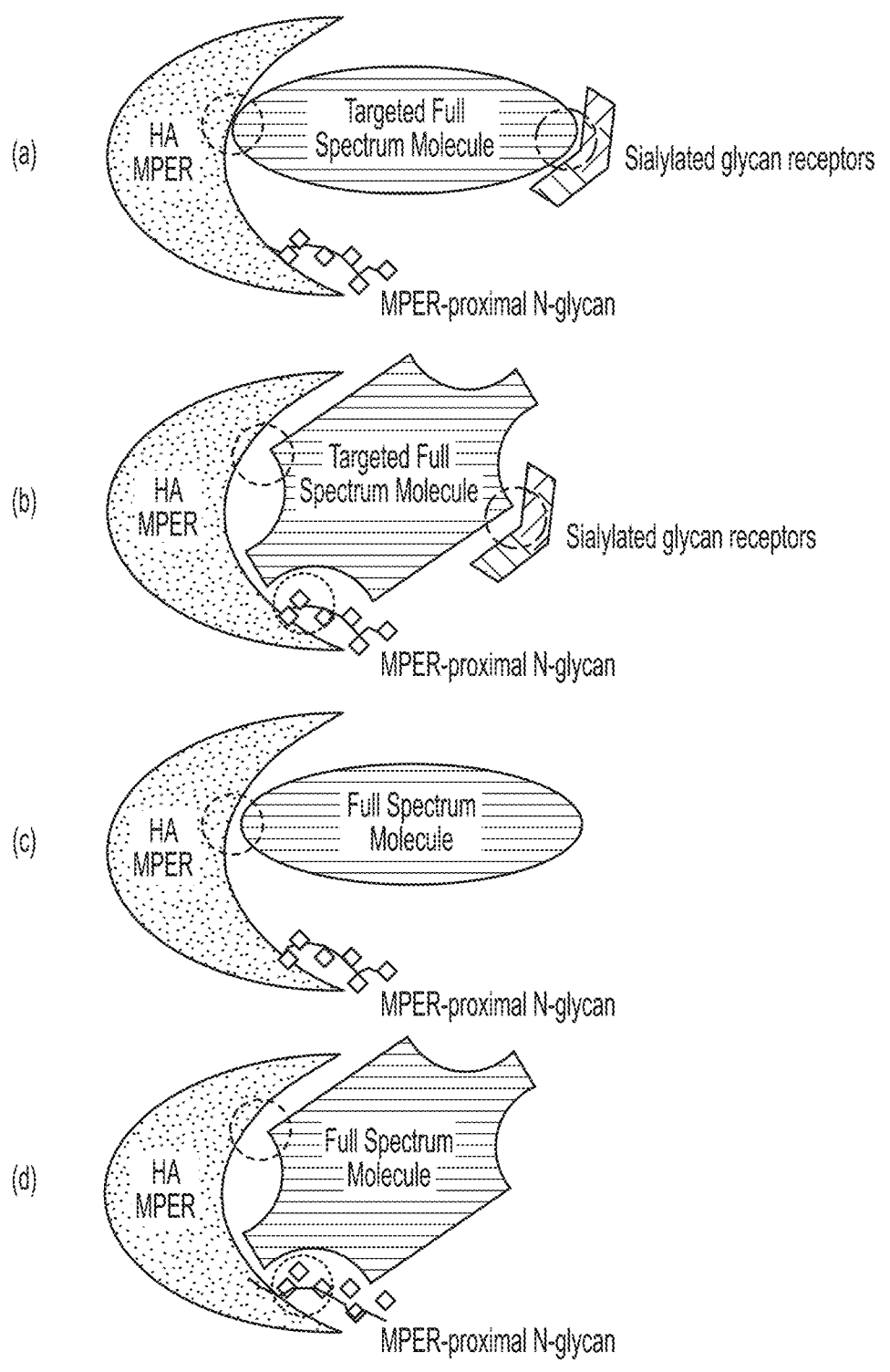

Targeting the delivery of therapeutics locally instead of globally is known to provide immensely less-toxic treatment with higher potency. In addition to the broad spectrum influenza neutralization properties, the ability to specifically bind α2,6 sialylated glycans on the HA receptor becomes an important property of the novel therapeutics for influenza. Without wishing to be bound by any theories, we propose the following strategies for targeted broad spectrum influenza neutralization as illustrated in FIG. 1. They include the ability to bind to the glycosylated/non-glycosylated conserved membrane proximal epitope region of the HA (broad spectrum neutralization) along with the ability to bind to sialylated glycan receptors in the human upper respiratory tract (targeted delivery).

Example 2

Infold Agents Bind HA Polypeptides

The present example illustrates binding of infold agents to HA polypeptide in an in vitro binding assay.

Maxisorp 96-well plate wells were coated with 0.2 µg an HA polypeptide of different subtypes (H1, H3, H5, H7 and H9) and left overnight at 4° C. The HA polypeptide coated plates were washed thrice with PBS and blocked with 1%

BSA in PBST. Different concentrations of infold agents along with C179 antibody (control) were added to HA polypeptide coated wells and the plate was incubated at RT for 2 hrs. The plate was washed thrice with PBST and the wells containing infold agents were incubated with mouse-anti-6×His antibody (1:1000 dilution) for 1 hr at RT. The plates were washed thrice with PBST and all wells were incubated with goat-anti-mouse HRP antibody for 1 hr at RT. Post-incubation the wells were washes with PBST and the bound HRP was measured using TMB substrate. TMB substrate was added to the wells, incubated for 3 minutes, followed by addition of 1 N sulphuric acid. Absorbance was measured at 450 nm.

Figure 7:
FIG. 7. Presents binding of an exemplary infold agent as compared to the binding of the C179 antibody to selected HA polypeptides, e.g., H1, H3, H5, H7 and H9.
Figure 8:
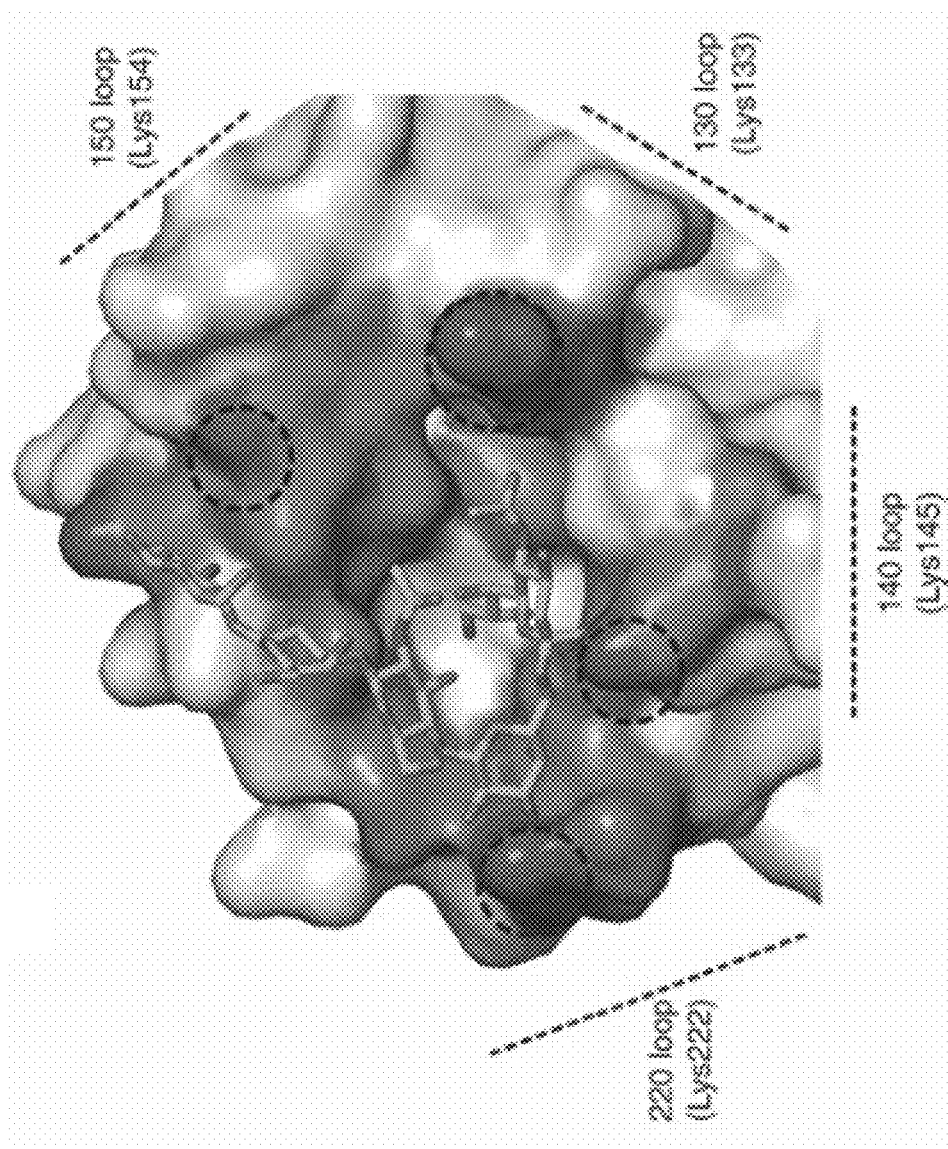
FIG. 8. Presents an α2,6-sialylated glycan (umbrella topology) HA receptor (cyan), shown here bound to the 2009 swine-origin influenza (commonly referred to as "pandemic influenza") H1N1 HA polypeptide (gray).

Our experimental results show good agreement with the predicted theoretical calculations with the designed proteins displaying high affinity towards both MPER-glycosylated and MPER-non-glycosylated strains of influenza. Our results show that an exemplary infold agent binds to various glycosylated and non-glycosylated HA polypeptides (H1, H3, H5, H7 and H9) with similar affinities (FIG. 7, left panel). These data are in comparison to the C179 antibody control (FIG. 7, right panel), which shows that the C179 antibody cannot distinguish between different HA polypeptide clades.

Example 3

Binding Affinity Between Infold Agents and the Targets of an Infold Agent

The present example shows a calculation of binding affinity, as represented as a dissociation constant ($K_d$), between an infold agent and the target of the infold agent. In this example, the infold agent is an exemplary infold agent and the target of the infold agent is an HA polypeptide.

Binding affinity between the exemplary infold agent and an HA polypeptide is a function of the concentrations of both the infold agent and the HA polypeptide. In the present example, the binding affinity is quantitatively described using dissociation constant ($K_d$). An example of how to measure the dissociation constant is described below.

HA polypeptide coated plates were used to perform ELISA assays with an exemplary infold agent as described previously. The measured absorbance at 450 nm was used to calculate the fractional saturation of the receptor. The fractional saturation was plotted as a function of molar concentration of the infold agent. The data was fit to the following equation:

$$y = \frac{I_0}{(K_d + I_0)}$$

where y is the fractional saturation, $I_0$ is the concentration of the infold agent and $K_d$ is the dissociation constant.

Using the above referenced calculation, and applying regression analysis, we have observed $K_d$ values in the range of 0.1 to 500 nM for binding of infold agents to HA polypeptides. In some embodiments, we have observed $K_d$ values in the range of 10 to 100 nM for binding of infold agents to HA polypeptides. In some embodiments, we have observed $K_d$ values in the range of 50 to 100 nM for binding of infold agents to HA polypeptides.

Example 4

Infold Agents Inhibit Virus Infectivity In Vitro

The present example illustrates the ability of infold agents to prevent virus infectivity in in vitro binding assays.

Figure 15:
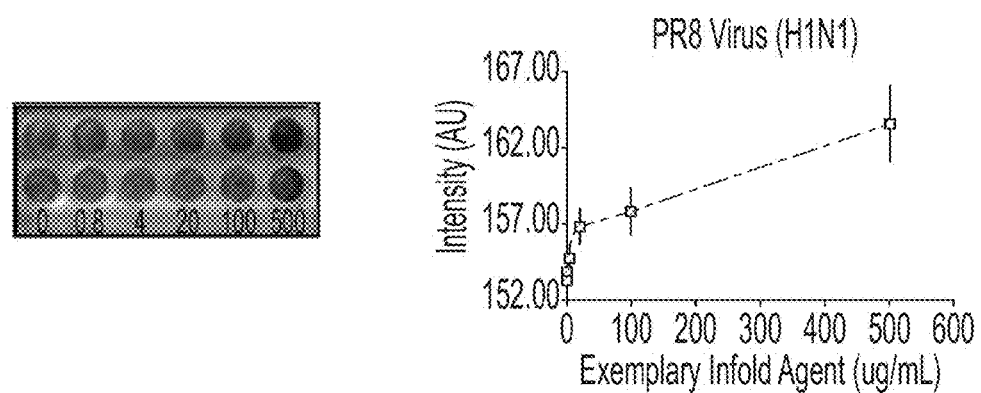
FIG. 15. Illustrates that an exemplary infold agent inhibits PR8 Virus (H1N1) influenza infectivity in vitro. The left panel highlights that the exemplary infold agent inhibits virus-induced plaque production in a dose-dependent manner for 6 different doses.
Figure 16:
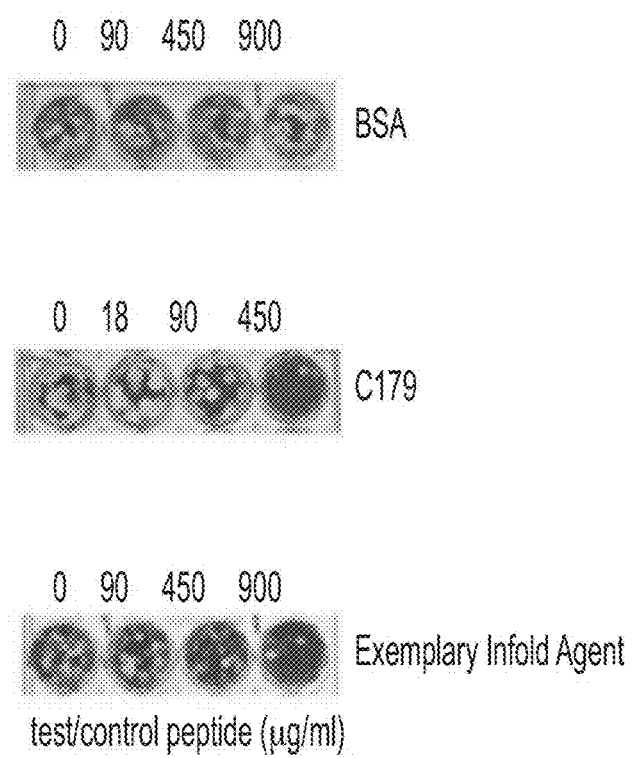
FIG. 16. Compares the activity of an exemplary infold agent to that of a control (BSA) and C179 antibody using a plaque assay with 4 doses. As shown by the plaque assay, the exemplary infold agent inhibits influenza infectivity.

The ability of an infold agent to inhibit influenza infection was evaluated in vitro using MDCK (Madin-Darby Canine Kidney) cells, an epithelial cell line commonly used for the propagation and testing of influenza virus strains. The inhibitory effects of the infold agent on infectivity were determined by measuring both viral yield and the extent of influenza-induced cytopathic effects (CPE) on the host cells. While plaque assay (FIGS. 15 and 16) and qRT-PCR were employed to quantify viral production, and a cell viability assay was used to measure CPE levels. The experiments were set up to allow for the infold agent to first bind to its viral target during a one hour pre-incubation period before introduction to the host cells. Infection was carried out in the presence of low levels of trypsin (1 µM). The plaque assay was performed by inoculating confluent monolayer of cells with serial dilutions of test samples and overlaying with a viscous suspension of the polymer Avicel (FMC Biopolymers). Plaques were allowed to develop over a period of 48 hours@ 35° C., formalin fixed, stained with crystal violet and visualized (FIGS. 15 and 16). The plaque count was used to calculate infectious viral titers in the test samples. Total viral output was also determined by quantitative RT-PCR, which measured levels of viral genome copies in the infected samples. The primers and labeled probe were designed to specifically amplify and measure a region within the viral hemagglutinin gene by the TaqMan method. The relative number of viable cells following infection was used as a measure of CPE. Sub-confluent cell cultures were exposed to a compound/virus mix (moi=1.0) for a period of one hour@ 35° C. Unbound virus and drug were then removed and replaced with virus growth medium. Cell viability was determined following 48 hours incubation using Promega's CellTiter Blue reagents (resazurin) as the extent of the metabolic conversion of the non-fluorescent resazurin to fluorescent resorufin read (555/585 nm excitation/emission; SpectraMax M2; Molecular Probes).

From these studied, we have found that infold agents inhibit virus-induced plaque production. In some embodiments, infold agents inhibit virus-induced plaque production in a dose-dependent manner.

Example 5

Infold Agents Bind HA Polypeptides In Vivo

The present example illustrates the ability of infold agents to bind HA polypeptides in in vivo.

Figure 17:
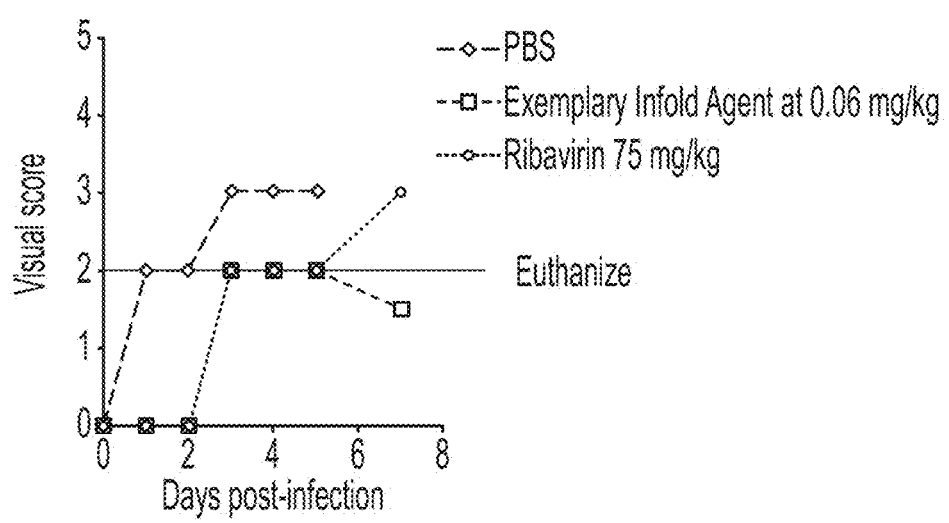
FIG. 17. Presents a H1N1 challenge in mice. In this challenge, an exemplary infold agent demonstrates delayed onset of H1N1 in mice as compared to the PBS control. The exemplary infold agent shows a similar delay of onset to that of the antiviral drug, Ribavirin, starting at around day five.
Figure 18:
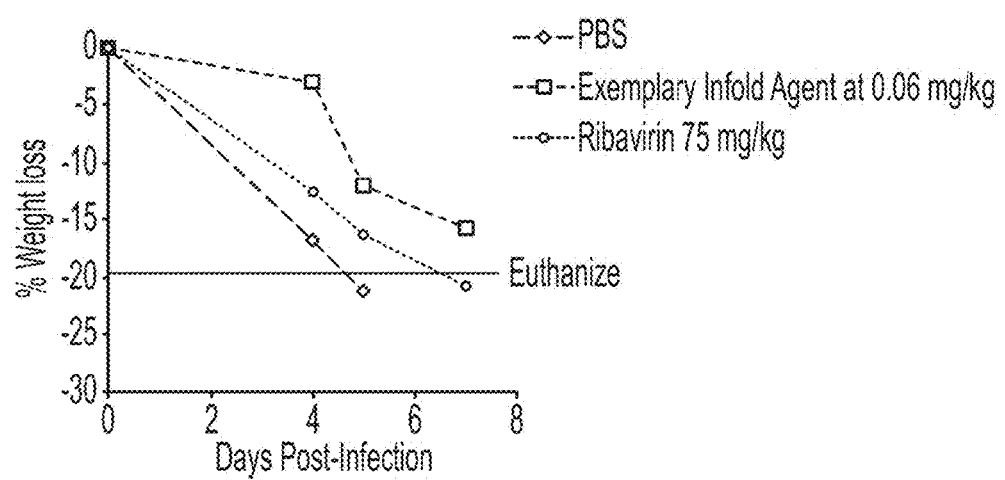
FIG. 18. Presents mice treated with an exemplary infold agent in an H1N1 challenge. In this challenge, mice treated with the exemplary infold agent have the least percent of weight loss post infection as compared to the PBS control or the antiviral drug, Ribavirin.

BALB/c mice (4-6 weeks old) were procured from Charles River Labs. The mice were weighed and divided into four groups of 6 mice each for the experiment. Each group was administered with isoflurane, dose with 0 mg/kg, 0.06 mg/kg, 0.6 mg/kg or 6 mg/kg of infold agent and allowed to recover (<2 min). They were then re-administered with isoflurane and challenged intranasally with a lethal dose of H1N1 PR8 virus. The mice were monitored daily for 14 days. The weight loss, visual score, and survival were recorded daily (FIGS. 17 and 18). Clinical signs of influenza infection in mice include hunched posture, ruffled fur, rapid breathing, loss of appetite, weight loss, and death. In addition, nasal washes were collected on day 3 from three animals each from the untreated group and group dosed with 6 mg/kg in order to demonstrate a reduction in viral replication in the nose with peak titers expected at day 3. The lungs were harvested from each mouse prior to sacrifice.

The results of these studies have shown that infold agents can successfully delay the onset of H1N1 infection in mice, with results that were comparable, or exceedingly better than an alternative anti-viral treatment, Ribavirin.

Example 6

Infold Agents in Diagnostics

The present example illustrates the ability of infold agents to provide a rapid way for (a) identifying the presence of influenza virus in a biological sample and (b) characterizing the virus, based on the subtype.

A sandwich ELISA (virus typing ELISA assay) assay is used for the purpose of identifying the presence of influenza virus and characterizing the virus subtype. For the virus typing ELISA assay, 96-well plates will be coated with 2 µg of infold agent and incubated overnight at 4° C. The plates would then be extensively washed with PBS and blocked with 1% BSA in PBST for 1 hr. Post blocking, the plates will be washed with PBST and stored at 4° C. till further use.

Biological samples suspected of containing influenza virus will be diluted in sample buffer (PBS) either directly or post processing. The diluted samples will then be applied to the infold-coated wells and incubated for 2 hrs at room temperature (RT) followed by extensive washing. Virus from the sample would thus be captured by the infold and lend itself for further analysis. Subtype specific antibody will be applied to different wells for 1 hr at RT. After further washes with PBST, HRP-conjugated secondary antibodies will be applied to the wells. Post-incubation, the wells would be washed, and treated with TMB substrate and 1 N sulphuric acid. The absorbance at 450 nm will be measured using a spectrophotometer. Appropriate negative and positive controls will be included.

The results of the virus typing ELISA assay will yield information about the presence of influenza virus in a sample and the subtype of the virus.

Example 7

Infold Agents for Influenza Virus Glycan Characterization

The present example illustrates the ability of infold agents as means to enrich and label influenza virus for glycan characterization using a glycan typing assay.

In the glycan typing assay, the infold agents would be conjugate to Qdot 525 Carboxyl Quantum Dots using EDC chemistry as per manufacturers instruction. The Qdot-infold complex will be added to processed biological samples and stirred well for 2 hrs. The sample will then be centrifuged and the Qdot-infold-InfA complex would be washed thrice with PBST. This complex would then be applied on glycan array (containing umbrella and cone topology glycans). After incubating for 2 hrs at RT, the wells would be washed thrice with PBST. The bound fluorescence would be measured using SpectraMax M2e spectrophotometer using bottom read mode.

The results of this assay will be yield information regarding the glycan characterization of influenza viruses.

Example 8

$IC_{50}$ Evaluation of Infold-28

The $IC_{50}$ of anti-influenza infold agents targeting HA have been quantified. These studies utilized the H1N1 influenza strain PR8 (A/Puerto Rico/8/34). In brief, confluent MDCK cells are infected with PR8 [4E3 PFU/mL] pre-incubated for 40 minutes with varying concentrations of anti-influenza agents. After one hour of infection, media was removed and replaced with virus-free, drug-containing media or virus-free, drug-free media depending upon the experiment. After 48 hours of incubation at 37° C., 5% $CO_2$, supernatants were collected. Viral RNA was isolated, and viral titer was quantified by real time PCR using primers specific for the virus M protein.

Figure 20:
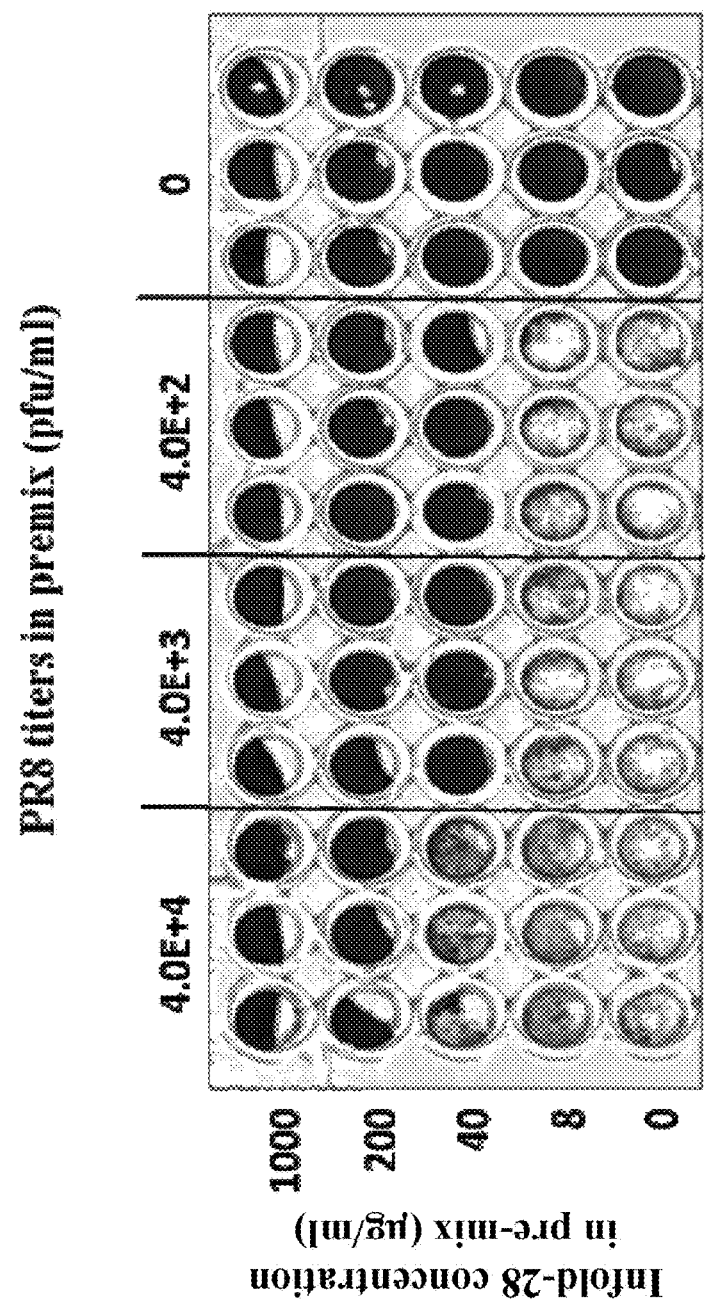

Initial assessment of the $IC_{50}$ values for Infold-28 were determined by microneutralization assay followed by quantitative PCR (qPCR). Mixtures of virus (PR8) and Infold-28 at various titers and concentrations, respectively, were pre-incubated for 1 hour at 35° C. before being applied to MDCK cell cultures in a 96-well tissue culture plate (~10,000 cells/well). After additional 48 hours of incubation, the culture medium was collected from each well for viral yield determination by qPCR. A preliminary indication of Infold-28 neutralizing activity came from staining of cells that survived infection with crystal violet (FIG. 20; stained cells are in black) which showed drug concentration-dependent and viral titer-dependent inhibition.

Figure 21:
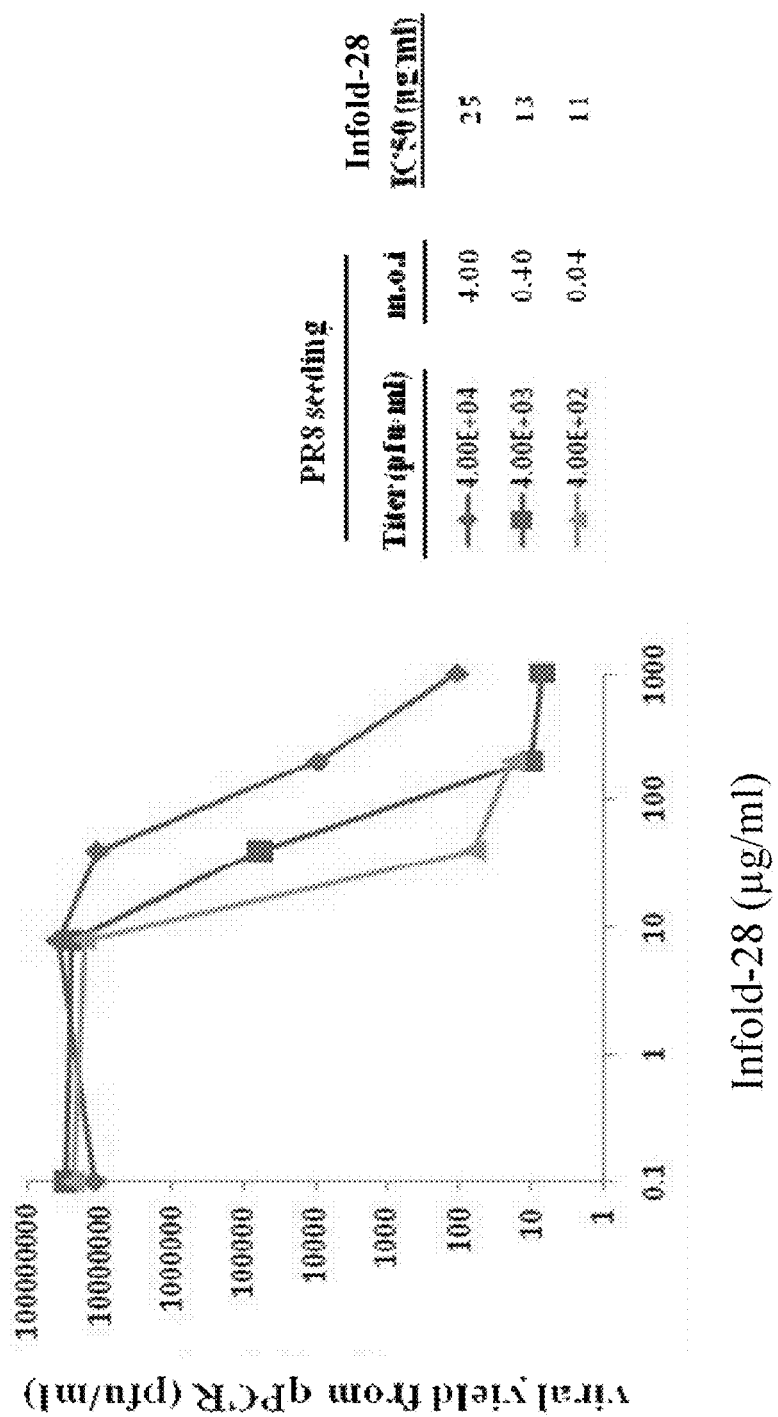
FIG. 21. Presents exemplary assessment of Infold Agent-28 activity in MDCK using RT-PCR to directly quantify viral genome amounts. Results show that the tested infold agent (Infold-28) is a potent inhibitor; $IC_{50}$ is influenced by the multiplicity of infection (moi).

Media from triplicate samples were combined and then subjected to direct quantification of viral yield by qPCR. Viral titers were calculated from the PCR Ct values with the aid of an internal standard curve, and the $IC_{50}$ values were determined by plotting the calculated titers against Infold-28 concentrations (FIG. 21). The results showed 50% inhibition ($IC_{50}$) of 200 pfu/ml (moi=0.04) of PR8 viral particles with 11 µg/ml Infold-28. As expected for an active agent, this value increased with viral titer. Results show that Infold-28 is a potent inhibitor; $IC_{50}$ is influenced by the multiplicity of infection (moi).

Figure 22:
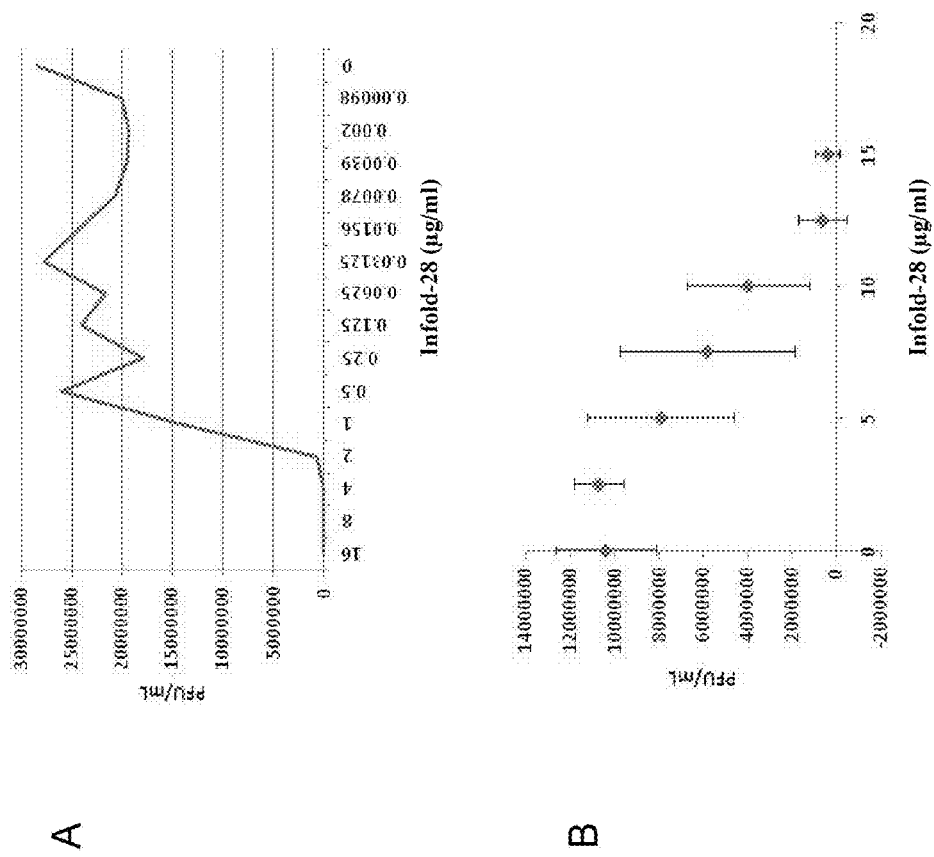
FIG. 22. Presents effects of Infold Agent-28 pre-incubation with PR8 on infectivity in MDCK cells. After infection, MDCK cells were grown in virus-free media either with (a) or without (b) Infold Agent-28 for 48 hours before viral titer was quantified by real time PCR using primers specific to the virus M protein. $=IC_{50}$ value calculated.

We also investigated how the method of addition of Infold-28 (i.e., in the overlay, etc.) influenced inhibition. The $IC_{50}$ of Infold-28 was measured to be ~1 µg/mL or ~6 nM when drug is added to the overlay after infection, and ~8 µg/mL or ~50 nM when drug is not added to the overlay after infection (FIG. 22). At least one other tested infold agent from Table 9 showed a comparable $IC_{50}$, whereas less potent activity was observed with at least one other such agent. Those of ordinary skill in the art will appreciate that the guidance provided herein permits adjustment and optimization of infold agents based on the representative agents provided in Table 9 without undue experimentation.

Example 9

Minimum Inhibitory Activity Assay

We have utilized a method to determine the minimum inhibitory concentration (MIC) of the antiviral agents against influenza A. To be active in this assay, the agent must bind to the virus and neutralize the virus' ability to form plaques. Briefly, an agent is serially diluted in two fold increments in PBS to form a concentration gradient across multiple wells. A known number of viral plaque forming units are added to each well and after 1 hour incubation, the mixture is added to an MDCK monolayer to allow viral binding. An Avicel overlay encourages plaque formation and the plaques are visualized by immunostain. The lowest concentration of agent to prevent plaque formation is reported as the MIC. These studies utilized H1N1 strain PR8 (A/Puerto Rico/8/34).

Representative infold agents, including Infold-28, from Table 9 showed activity in the assay versus H1N1, and specifically showed MIC<120, and even within a range of 15 to about 100, or about 15 to about 60, or about 15-20 to about 60-100. Infold agents tested in this assay did not show activity versus an H3N2 virus in the particular studies performed. At least in some cases where no activity was observed (whether versus H1N1, H3N2, or both) may have been issues with stability of infold agent in the assay. Those of ordinary skill in the art will appreciate that improvements to the stability of such agents (e.g., via modification of amino acid sequence or backbone), steady or repeat infusion of agent, or other experimental adjustments to agents and/or conditions of the assay may reveal activity not seen in the particular test thusfar performed.

Example 10

PEGylation of Infold-28

Various PEG were added to Infold-28 and MIC was determined. We observed a trend where PEGylation with larger PEG molecules (e.g., 20 kD) negatively impacts Infold-28's performance in MIC assays, while smaller PEG molecules (e.g., 5 kD) appear to be better tolerated.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of making a pharmaceutical composition comprising the step of:
    formulating an infold agent with one or more inactive agents or additives, wherein the infold agent comprises an infold selected from the group consisting of Infold-1, Infold-2, Infold-3, Infold-4, Infold-5, Infold-6, Infold-7, Infold-8, Infold-9, Infold-10, Infold-11, Infold-12, Infold-13, Infold-14, Infold-15, Infold-16, Infold-17, Infold-18, Infold-19, Infold-20, Infold-21, Infold-22, Infold-23, Infold-24, Infold-25, Infold-26, Infold-27, Infold-28, Infold-29, Infold-30, Infold-31, Infold-32, Infold-33, Infold-34, Infold-35, Infold-36, Infold-37, Infold-38, Infold-39, and Infold-40 to provide a pharmaceutical composition comprising at least one unit dose of the infold agent.

2. The method of claim 1, wherein the inactive agent is a sterile biocompatible carrier.

3. The method of claim 2, where the sterile biocompatible carrier is selected from one or more of sterile water, saline, buffered saline, and dextrose solution.

4. The method of claim 1, wherein the additive is selected from one or more of stabilizer, excipient, and preservatives.

5. The method of claim 4, wherein the excipient is selected from one or more of sugars and amino acids.

6. The method of claim 1, wherein the pharmaceutical composition is formulated for administration by a route selected from the group consisting of oral, intravenous, intramuscular, intra-arterial, subcutaneous, intraventricular, transdermal, interdermal, rectal, intravaginal, intraperitoneal, topical, mucosal, nasal, buccal, enteral, sublingual, intratracheal or bronchial.

7. The method of claim 6, wherein the administration is by intratracheal or bronchial instillation.

8. The method of claim 6, wherein the administration is by inhalation.

9. The method of claim 1, wherein the pharmaceutical composition is formulated as an oral spray, a nasal spray, or an aerosol.

10. The method of claim 6, wherein the administration is by oral.

11. The method of claim 1, wherein the pharmaceutical composition comprises an oral spray, a nasal spray or an aerosol.

* *